United States Patent
Anderson et al.

(10) Patent No.: US 9,969,679 B2
(45) Date of Patent: May 15, 2018

(54) ANTI-PROLIFERATIVE COMPOUNDS AND USES THEREOF

(71) Applicants: Dana-Farber Cancer Institute, Inc., Boston, MA (US); The General Hospital Corporation, Boston, MA (US)

(72) Inventors: Kenneth C. Anderson, Wellesley, MA (US); Teru Hideshima, Brookline, MA (US); Ralph Mazitschek, Belmont, MA (US); Gullu Gorgun, Chestnut Hill, MA (US)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days. days.

(21) Appl. No.: 14/413,745

(22) PCT Filed: Jul. 10, 2013

(86) PCT No.: PCT/US2013/049831
§ 371 (c)(1),
(2) Date: Jan. 9, 2015

(87) PCT Pub. No.: WO2014/011713
PCT Pub. Date: Jan. 16, 2014

(65) Prior Publication Data
US 2015/0191417 A1    Jul. 9, 2015

Related U.S. Application Data

(60) Provisional application No. 61/669,932, filed on Jul. 10, 2012.

(51) Int. Cl.
| | | |
|---|---|---|
| C07C 223/06 | (2006.01) | |
| A61K 45/06 | (2006.01) | |
| A61K 31/136 | (2006.01) | |
| A61K 31/15 | (2006.01) | |
| A61K 31/164 | (2006.01) | |
| A61K 31/165 | (2006.01) | |
| A61K 31/216 | (2006.01) | |
| A61K 31/395 | (2006.01) | |
| A61K 31/4166 | (2006.01) | |
| A61K 31/445 | (2006.01) | |
| A61K 31/655 | (2006.01) | |

(Continued)

(52) U.S. Cl.
CPC .......... *C07C 223/06* (2013.01); *A61K 31/136* (2013.01); *A61K 31/15* (2013.01); *A61K 31/164* (2013.01); *A61K 31/165* (2013.01); *A61K 31/216* (2013.01); *A61K 31/395* (2013.01); *A61K 31/4166* (2013.01); *A61K 31/445* (2013.01); *A61K 31/655* (2013.01); *A61K 31/69* (2013.01); *A61K 45/06* (2013.01); *C07C 251/48* (2013.01); *C07C 251/86* (2013.01); *C07D 211/62* (2013.01); *C07D 233/80* (2013.01)

(58) Field of Classification Search
CPC .................................................. C07C 223/06
See application file for complete search history.

(56) References Cited

U.S. PATENT DOCUMENTS

| 5,370,954 A | 12/1994 | Ohta et al. |
| 6,949,678 B2 | 9/2005 | Kunimoto et al. |

(Continued)

FOREIGN PATENT DOCUMENTS

| EP | 1 443 039 A1 | 8/2004 |
| GB | 1 258 094 A | 12/1971 |

(Continued)

OTHER PUBLICATIONS

Online "http://web.archive.org/web/20100910093620/http://ambinter.com/orderinginfo.jsp" accessed Oct. 10, 2015, Dated Sep. 9, 2010.*

(Continued)

*Primary Examiner* — David K O'Dell
(74) *Attorney, Agent, or Firm* — Wolf, Greenfield & Sacks, P.C.

(57) ABSTRACT

The present invention provides novel compounds of Formula (I), and pharmaceutically acceptable salts, tautomers, stereoisomers, solvates, hydrates, polymorphs, and compositions thereof. Also provided are methods and kits involving the inventive compounds for treating proliferative diseases (e.g., cancers (e.g., breast cancer, prostate cancer, lung cancer, and ovarian cancer), benign neoplasms, angiogenesis, inflammatory diseases, and autoimmune diseases) in a subject. Treatment of a subject with a proliferative disease using a compound of the invention may enhance the anti-tumor immune response by inhibiting or eliminating the immune suppression mediated by immune suppressor myeloid cells (MDSCs), inducing apoptosis, and/or inhibit or down-regulate proteins (e.g., epidermal growth factor receptor (EGFR), human epidermal growth factor receptor 2 (HER2), estrogen receptor (ER), X-linked inhibitor of apoptosis protein (XIAP), and heat shock protein 90 (Hsp90)) in the subject.

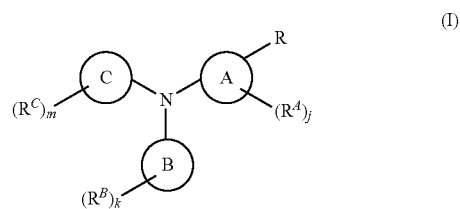

20 Claims, 19 Drawing Sheets

(51) Int. Cl.
*A61K 31/69* (2006.01)
*C07D 233/80* (2006.01)
*C07D 211/62* (2006.01)
*C07C 251/48* (2006.01)
*C07C 251/86* (2006.01)

(56) References Cited

U.S. PATENT DOCUMENTS

| | | | |
|---|---|---|---|
| 7,078,369 | B2 | 7/2006 | Dietrich et al. |
| 7,316,878 | B2 | 1/2008 | Budreckiene et al. |
| 7,351,508 | B2 | 4/2008 | Grazulevicius et al. |
| 7,414,011 | B2 | 8/2008 | Dietrich et al. |
| 8,440,716 | B2 * | 5/2013 | Tang .............. C07C 259/06 514/539 |
| 2003/0087127 | A1 | 5/2003 | Lee et al. |
| 2004/0092598 | A1 | 5/2004 | Watkins et al. |
| 2005/0051758 | A1 | 3/2005 | Yamamoto et al. |
| 2006/0079528 | A1 | 4/2006 | Finn et al. |
| 2006/0246317 | A1 | 11/2006 | Lyu et al. |
| 2007/0148185 | A1 | 6/2007 | Rathore et al. |
| 2008/0255389 | A1 | 10/2008 | Coggan et al. |
| 2011/0028716 | A1 | 2/2011 | Kay et al. |
| 2011/0172303 | A1 | 7/2011 | Tang et al. |
| 2013/0032720 | A1 | 2/2013 | Lee et al. |
| 2013/0331455 | A1 | 12/2013 | Tang et al. |

FOREIGN PATENT DOCUMENTS

| | | |
|---|---|---|
| GB | 1258094 * | 12/1971 |
| GB | 2 410 025 A | 7/2005 |
| JP | H 09-204054 A | 8/1997 |
| RU | 2006115795 A | 11/2007 |
| WO | WO 98/47869 A1 | 10/1998 |
| WO | WO 99/11262 A1 | 3/1999 |
| WO | WO 99/37603 A1 | 7/1999 |
| WO | WO 2005/037773 A | 4/2005 |
| WO | WO 2008/091349 A1 | 7/2008 |
| WO | WO 2009/141288 A2 | 11/2009 |
| WO | WO 2010/011296 A2 | 1/2010 |
| WO | WO 2014/011713 A2 | 1/2014 |

OTHER PUBLICATIONS

Singh "Targeted covalent drugs of the kinase family" Current Opinion in Chemical Biology 2010, 14:475-480.*
Martin, Yvonne C. et. al. "Do Structurally Similar Molecules Have Similar Biological Activity?" Journal of Medicinal Chemistry 2002, 45, 4350-4358.*
Dorwald F. A. Side Reactions in Organic Synthesis, 2005, Wiley: VCH, Weinheim p. IX of Preface p. 1-15, 41.*
STN Chemical Database entry RN 389611-36-3 for Benzoic acid, [[4-(diphenylamino)phenyl]methylene]hydrazide, Feb 5, 2002.*
Pozharskii et. al. Heterocycles in Life and Society Wiley, 1997, pp. 1-6.*
Pitt "Heteroaromatic Rings of the Future" J. Med. Chem. 2009, 52, 2952-2963.*
STN Chemical Database Entry for 1,4-Benzodioxin-2-carboxylic acid, 2,3-dihydro-, [[4-(diphenylamino)phenyl]methylene] hydrazide RN 475142-03-1 Supplier: Ambinter Entered STN: Dec. 5, 2002.*
Online "http://web.archive.org/web/20070630171813/http://www.enamine.net/index.php?option=com_content&task=view&id=22 &menuid=51 &PHPSESSID=64a4f248f69d671a413f487bb62c4d90" dated Jun. 30, 2007, accessed Feb. 19, 2015.*
Online "http://web.archive.org/web/20070202005900/http://www.ambinter.com/" dated Feb. 2, 2007, accessed Feb. 28, 2013.*
STN Registry Chemical Database entry for Acetic acid, (2E)-2-[[4-(diphenylamino)phenyl]methylene]hydrazide, RN 1137457-65-8, ED Entered STN: Apr. 21, 2009.*
PubChem Chemical Database PubChem SID: 47660300 External ID: Ald3-H_000110 entry for Acetic acid, (2E)-2-[[4(diphenylamino)phenyl]methylene]hydrazide, Deposit Date: Feb. 20, 2008 Online "https://pubchem.ncbi.nlm.nih.gov/substance/47660300" accessed Jun. 19, 2017.*
STN Chemical Database Entry for 3,5-Pyridinedicarboxylic acid, 1,4-dihydro-2,6-dimethyl-4-phenyl-, 3,5-bis[2-[[4-(diphenylamino)phenyl]methylene]hydrazide]RN 474673-75-1 Supplier: Ambinter Entered STN: Nov. 27, 2002.*
International Preliminary Report on Patentability for PCT/US2013/049831, dated Jan. 22, 2015.
International Search Report and Written Opinion for PCT/US2013/049831, dated Apr. 4, 2014.
Invitation to Pay Additional Fees for PCT/US2013/049831, dated Jan. 15, 2014.
Almand et al., Increased production of immature myeloid cells in cancer patients: a mechanism of immunosuppression in cancer. J Immunol. Jan. 1, 2001;166(1):678-89.
Berge et al., Pharmaceutical salts. J Pharm Sci. Jan. 1977;66(1):1-19.
Bradner et al., Chemical phylogenetics of histone deacetylases. Nat Chem Biol. Mar. 2010;6(3):238-243. Epub Feb. 7, 2010.
Bronte et al., Identification of a CD11b(+)/Gr-1(+)/CD31(+) myeloid progenitor capable of activating or suppressing CD8(+) T cells. Blood. Dec. 1, 2000;96(12):3838-46.
Budreckiene et al., Methacryloyl functionalized hydrazones as hole-transporting materials for electrophotography. Materials Science—Poland. 2009;27(1):61-72.
Diaz-Montero et al., Increased circulating myeloid-derived suppressor cells correlate with clinical cancer stage, metastatic tumor burden, and doxorubicin-cyclophosphamide chemotherapy. Cancer Immunol Immunother. Jan. 2009;58(1):49-59. doi: 10.1007/s00262-008-0523-4. Epub Apr. 30, 2008.
Herzenberg et al., The history and future of the fluorescence activated cell sorter and flow cytometry: a view from Stanford. Clin Chem. Oct. 2002;48(10):1819-27.
Hideshima et al., A proto-oncogene BCL6 is up-regulated in the bone marrow microenvironment in multiple myeloma cells. Blood. May 6, 2010;115(18):3772-5. doi: 10.1182/blood-2010-02-270082. Epub Mar. 12, 2010.
Hogenkamp et al., Synthesis and in vitro activity of 3 beta-substituted-3 alpha-hydroxypregnan-20-ones: allosteric modulators of the GABAA receptor. J Med Chem. Jan. 3, 1997;40(1):61-72.
Kusmartsev et al., Antigen-specific inhibition of CD8+ T cell response by immature myeloid cells in cancer is mediated by reactive oxygen species. J Immunol. Jan. 15, 2004;172(2):989-99.
Kusmartsev et al., Immature myeloid cells and cancer-associated immune suppression. Cancer Immunol Imm293-8unother. Aug. 2002;51(6):293-8. Epub Apr. 24, 2002.
Movahedi et al., Identification of discrete tumor-induced myeloid-derived suppressor cell subpopulations with distinct T cell-suppressive activity. Blood. Apr. 15, 2008;111(8):4233-44. doi: 10.1182/blood-2007-07-099226. Epub Feb. 13, 2008.
Perez et al., Simultaneous measurement of multiple active kinase states using polychromatic flow cytometry. Nat Biotechnol. Feb. 2002;20(2):155-62.
Santo et al., Preclinical activity, pharmacodynamic, and pharmacokinetic properties of a selective HDAC6 inhibitor, ACY-1215, in combination with bortezomib in multiple myeloma. Blood. Mar. 15, 2012;119(11):2579-89. doi: 10.1182/blood-2011-10-387365. Epub Jan. 19, 2012.
Sawanobori et al., Chemokine-mediated rapid turnover of myeloid-derived suppressor cells in tumor-bearing mice. Blood. Jun. 15, 2008;111(12):5457-66. doi: 10.1182/blood-2008-01-136895. Epub Mar. 28, 2008.
Upasani et al., 3 alpha-Hydroxy-3 beta-(phenylethynyl)-5 beta-pregnan-20-ones: synthesis and pharmacological activity of neuroactive steroids with high affinity for GABAA receptors. J Med Chem. Jan. 3, 1997;40(1):73-84.
Vegas et al., Fluorous-based small-molecule microarrays for the discovery of histone deacetylase inhibitors. Angew Chem Int Ed Engl. 2007;46(42):7960-4.

(56) References Cited

OTHER PUBLICATIONS

Youn et al., Characterization of the nature of granulocytic myeloid-derived suppressor cells in tumor-bearing mice. J Leukoc Biol. Jan. 2012;91(1):167-81. doi: 10.1189/jlb.0311177. Epub Sep. 27, 2011.
Youn et al., The biology of myeloid-derived suppressor cells: The blessing and the curse of morphological and functional heterogeneity. Eur J Immunol. 2010;40(11):2969-75.
Extended European Search Report for EP 13817396.8, dated Jan. 21, 2016.
Marks et al., Histone deacetylases and cancer: causes and therapies. *Nat Rev Cancer*. Dec. 2001;1(3):194-202.

\* cited by examiner

ANTI-PROLIFERATIVE COMPOUNDS AND USES THEREOF

RELATED APPLICATIONS

The present application is a national stage filing under 35 U.S.C. § 371 of international PCT application, PCT/US2013/049831, filed Jul. 10, 2013, which claims priority under 35 U.S.C. § 119(e) to U.S. provisional patent application, U.S. Ser. No. 61/669,932, filed Jul. 10, 2012, each of which is incorporated herein by reference.

BACKGROUND OF THE INVENTION

The interaction between tumor cells and surrounding non-malignant stromal and immune cells provides a supportive environment for tumor development, growth, invasion, and metastasis. Development of a tumor induces cellular and molecular changes to suppress anti-tumor immune responses mediated by immune effector cells. Myeloid derived suppressor cells (MDSCs) are immature myeloid progenitor cells with potent immune suppressive activities. Increased numbers of MDSCs have been found in many pathologic conditions including infections, inflammatory diseases, and cancer, and correlate with disease prognosis and clinical stage 1. MDSCs directly suppress effector T, NKT, and NK cell-mediated anti-tumor immune responses by producing arginases (ARGs), reactive species of oxygen (ROS), inducible nitric oxide synthase (iNOS), and immunosuppressive cytokines, and by depleting metabolic factors from the microenvironment required for effector cell activation (Youn et al., "The biology of myeloid-derived suppressor cells: the blessing and the curse of morphological and functional heterogeneity." *Eur. J. Immunol.* (2011) 40:2969-2975). In mice, MDSCs have been identified with low expression of MHC class II and CD80 (Movahedi et al., "Identification of discrete tumor-induced myeloid-derived suppressor cell subpopulations with distinct T cell-suppressive activity." *Blood* (2008) 111:4233-4244; Sawanobori et al., "Chemokine-mediated rapid turnover of myeloid-derived suppressor cells in tumor-bearing mice." *Blood* (2008) 111:5457-5466), to be either neutrophil like CD11b$^+$Gr1$^{high}$ (G-MDSC) or monocyte like CD11b$^+$Gr1$^{low}$ cells (M-MDSC) (Movahedi et al., "Identification of discrete tumor-induced myeloid-derived suppressor cell subpopulations with distinct T cell-suppressive activity." *Blood* (2008) 111:4233-4244; Kusmartsev et al., "Immature myeloid cells and cancer-associated immune suppression." *Cancer Immunol. Immunother.* (2002) 51:293-298; Bronte et al., "Identification of a CD11b(+)/Gr-1(+)/CD31(+) myeloid progenitor capable of activating or suppressing CD8(+) T cells." *Blood* (2000) 96:3838-3846; Kusmartsev et al., "Antigen-specific inhibition of CD8$^+$ T cell response by immature myeloid cells in cancer is mediated by reactive oxygen species." *J. Immunol.* (2004) 172:989-999). However, MDSCs in human are characterized by expression of additional phenotypic surface antigens including with high CD11b, CD33, and IL-4Rα expression, low or no CD14 and Lin expression, and variable expression of CD15 (Almand et al., "Increased production of immature myeloid cells in cancer patients: a mechanism of immunosuppression in cancer." *J. Immunol.* (2001) 166:678-689; Diaz-Montero et al., "Increased circulating myeloid-derived suppressor cells correlate with clinical cancer stage, metastatic tumor burden, and doxorubicin-cyclophosphamide chemotherapy." *Cancer Immunol. Immunother.* (2009) 58:49-59). In cancer, MDSCs are tumor supporting, immune suppressive cells and mostly accumulate with a granulocytic-MDSC (G-MDSC) phenotype (Youn et al., "Characterization of the nature of granulocytic myeloid-derived suppressor cells in tumor-bearing mice." *J. Leukoc. Biol.* (2012) 91:167-181). Alternatively, MDSC-mediated immune suppression plays an important role in autoimmunity, inflammation, and transplantation. MDSC-mediated immune suppression is a major cause for failures in anti-tumor immunotherapy, and therefore, modulation and/or elimination of MDSCs and/or MDSC-mediated immune suppression (e.g., by inhibiting HDACs) is needed for the development of novel anti-tumor therapies.

Proliferation of solid tumors (e.g., breast, lung, ovarian, and prostate cancer) can be modulated by growth factor receptor expression or activity. For example, proliferation of breast cancer cells is mediated by transmembrane growth factor receptors and intracellular hormone/steroid receptors such as epidermal growth factor receptor (EGFR), human epidermal growth factor receptor 2 (HER2), human epidermal growth factor receptor 3 (HER3), estrogen receptor (ER), and progesterone receptor (PGR). Therefore, inhibition of these receptors is a promising therapeutic strategy in the treatment of solid tumors. Indeed, small molecule inhibitors and monoclonal antibodies against these receptors have already been generated and show remarkable clinical outcome. Importantly, simultaneous inhibition of these receptors may be able to enhance activity of individual agents.

SUMMARY OF THE INVENTION

The present invention provides novel compounds of Formula (I), and pharmaceutically acceptable salts, tautomers, stereoisomers, solvates, hydrates, polymorphs, and pharmaceutical compositions thereof. Also provided are methods, uses, and kits involving the inventive compounds, or pharmaceutically acceptable salts, tautomers, stereoisomers, solvates, hydrates, polymorphs, or pharmaceutical compositions thereof, for the treatment of proliferative diseases (e.g., cancers (e.g., breast cancer, prostate cancer, lung cancer, and ovarian cancer), benign neoplasms, angiogenesis, inflammatory diseases, and autoimmune diseases) in a subject.

Without wishing to be bound by any particular theory, the compounds of the invention may enhance the anti-tumor immune response by eliminating the MDSC-mediated immune suppression in a subject. Thus, treatment with the inventive compounds may prevent tumor escape from immunosurveillance. The compounds of the invention may also be useful to prevent MDSC-promoted cancer metastasis. Moreover, manipulation of immunosuppressive cells by using the inventive compounds may be useful for the modulation of the immune response in transplantation, inflammation, and autoimmunity.

The compounds of the invention may also induce apoptosis in a subject. Inhibited apoptosis may cause uncontrolled cell proliferation and, therefore, proliferative diseases. The inventive compounds may induce apoptosis through a number of pathways, including enhancing aggresome formation and/or unfolded protein responses (UPRs).

Moreover, the inventive compounds may inhibit and/or down-regulate the expression of a variety of receptors (e.g., epidermal growth factor receptor (EGFR), human epidermal growth factor receptor 2 (HER2), estrogen receptor (ER, including ERα and ERβ), X-linked inhibitor of apoptosis protein (XIAP), and heat shock protein 90 (Hsp90)). Overexpression, overactivity, or up-regulation of these receptors has been associated with cell proliferation, inhibition of apoptosis, and/or disruption of DNA repair, and may cause proliferative diseases.

In one aspect, the present invention provides compounds of Formula (I):

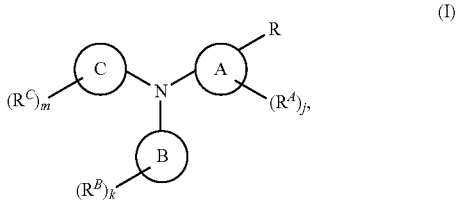

and pharmaceutically acceptable salts, tautomers, stereoisomers, solvates, hydrates, and polymorphs thereof, wherein:

Rings A, B, and C are each independently an aryl ring or heteroaryl ring;

R is a group of formula:

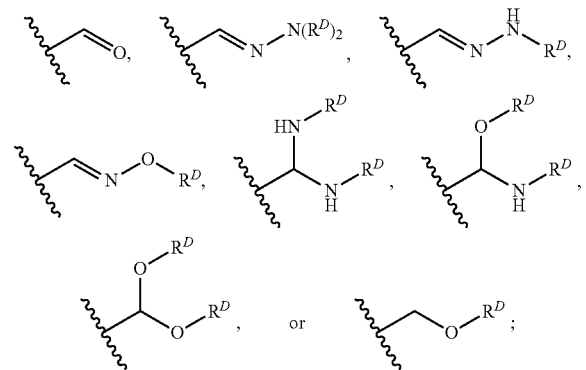

each occurrence of $R^A$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A1})_2$, —$SR^{A1}$, —CN, —$C(=NR^{A1})R^{A1}$, —$C(=NR^{A1})OR^{A1}$, —$C(=NR^{A1})SR^{A1}$, —$C(=NR^{A1})N(R^{A1})_2$, —$C(=S)R^{A1}$, —$C(=S)OR^{A1}$, —$C(=S)SR^{A1}$, —$C(=S)N(R^{A1})_2$, —$NO_2$, —$N_3$, —$N(R^{A1})_3{}^+F^-$, —$N(R^{A1})_3{}^+Cl^-$, —$N(R^{A1})_3{}^+Br^-$, —$N(R^{A1})_3{}^+I^-$, —$N(OR^{A1})R^{A1}$, —$NR^{A1}C(=O)R^{A1}$, —$NR^{A1}C(=O)OR^{A1}$, —$NR^{A1}C(=O)SR^{A1}$, —$NR^{A1}C(=O)N(R^{A1})_2$, —$NR^{A1}C(=S)R^{A1}$, —$NR^{A1}C(=S)OR^{A1}$, —$NR^{A1}C(=S)SR^{A1}$, —$NR^{A1}C(=S)N(R^{A1})_2$, —$NR^{A1}C(=NR^{A1})R^{A1}$, —$NR^{A1}C(=NR^{A1})OR^{A1}$, —$NR^{A1}C(=NR^{A1})SR^{A1}$, —$NR^{A1}C(=NR^{A1})N(R^{A1})_2$, —$NR^{A1}S(=O)_2R^{A1}$, —$NR^{A1}S(=O)_2OR^{A1}$, —$NR^{A1}S(=O)_2SR^{A1}$, —$NR^{A1}S(=O)_2N(R^{A1})_2$, —$NR^{A1}S(=O)R^{A1}$, —$NR^{A1}S(=O)OR^{A1}$, —$NR^{A1}S(=O)SR^{A1}$, —$NR^{A1}S(=O)N(R^{A1})_2$, —$NR^{A1}P(=O)$, —$NR^{A1}P(=O)_2$, —$NR^{A1}P(=O)(R^{A1})_2$, —$NR^{A1}P(=O)R^{A1}(OR^{A1})$, —$NR^{A1}P(=O)(OR^{A1})_2$, —$OC(=O)R^{A1}$, —$OC(=O)OR^{A1}$, —$OC(=O)SR^{A1}$, —$OC(=O)N(R^{A1})_2$, —$OC(=NR^{A1})R^{A1}$, $OC(=NR^{A1})OR^{A1}$, —$OC(=NR^{A1})N(R^{A1})_2$, —$OC(=S)R^{A1}$, —$OC(=S)OR^{A1}$, —$OC(=S)SR^{A1}$, —$OC(=S)N(R^{A1})_2$, —$ON(R^{A1})_2$, —$OS(=O)R^{A1}$, —$OS(=O)OR^{A1}$, —$OS(=O)SR^{A1}$, —$OS(=O)N(R^{A1})_2$, —$OS(=O)_2R^{A1}$, —$OS(=O)_2OR^{A1}$, —$OS(=O)_2SR^{A1}$, —$OS(=O)_2N(R^{A1})_2$, —$OP(=O)(R^{A1})_2$, —$OP(=O)R^{A1}(OR^{A1})$, —$OP(=O)(OR^{A1})_2$, —$S(=O)R^{A1}$, —$S(=O)OR^{A1}$, —$S(=O)N(R^{A1})_2$, —$S(=O)_2R^{A1}$, —$S(=O)_2OR^{A1}$, —$S(=O)_2N(R^{A1})_2$, —$SC(=O)R^{A1}$, —$SC(=O)OR^{A1}$, —$SC(=O)SR^{A1}$, —$SC(=O)N(R^{A1})_2$, —$SC(=S)R^{A1}$, —$SC(=S)OR^{A1}$, —$SC(=S)SR^{A1}$, —$SC(=S)N(R^{A1})_2$, —$P(=O)(OR^{A1})_2$, —$P(=O)R^{A1}(OR^{A1})$, —$P(=O)R^{A1}(OR^{A1})$, and —$P(=O)_2$, wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;

each occurrence of $R^B$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B1}$, —$N(R^{B1})_2$, —$SR^{B1}$, —CN, —$C(=NR^{B1})R^{B1}$, —$C(=NR^{B1})OR^{B1}$, —$C(=NR^{B1})SR^{B1}$, —$C(=NR^{B1})N(R^{B1})_2$, —$C(=S)R^{B1}$, —$C(=S)OR^{B1}$, —$C(=S)SR^{B1}$, —$C(=S)N(R^{B1})_2$, —$NO_2$, —$N_3$, —$N(R^{B1})_3{}^+F^-$, —$N(R^{B1})_3{}^+Cl^-$, —$N(R^{B1})_3{}^+Br^-$, —$N(R^{B1})_3{}^+I^-$, —$N(OR^{B1})R^{B1}$, —$NR^{B1}C(=O)R^{B1}$, —$R^{B1}C(=O)OR^{B1}$, —$NR^{B1}C(=O)SR^{B1}$, —$NR^{B1}C(=O)N(R^{B1})_2$, —$NR^{B1}C(=S)R^{B1}$, —$NR^{B1}C(=S)OR^{B1}$, —$NR^{B1}C(=S)SR^{B1}$, —$NR^{B1}C(=S)N(R^{B1})_2$, —$NR^{B1}C(=NR^{B1})R^{B1}$, —$NR^{B1}C(=NR^{B1})OR^{B1}$, —$NR^{B1}C(=NR^{B1})SR^{B1}$, —$NR^{B1}C(=NR^{B1})N(R^{B1})_2$, —$NR^{B1}S(=O)_2R^{B1}$, —$NR^{B1}S(=O)_2OR^{B1}$, —$NR^{B1}S(=O)_2SR^{B1}$, —$NR^{B1}S(=O)_2N(R^{B1})_2$, —$NR^{B1}S(=O)R^{B1}$, —$NR^{B1}S(=O)OR^{B1}$, —$NR^{B1}S(=O)SR^{B1}$, —$NR^{B1}S(=O)N(R^{B1})_2$, —$NR^{B1}P(=O)$, —$NR^{B1}P(=O)_2$, —$NR^{B1}P(=O)(R^{B1})_2$, —$NR^{B1}P(=O)R^{B1}(OR^{B1})$, —$NR^{B1}P(=O)(OR^{B1})_2$, —$OC(=O)R^{B1}$, —$OC(=O)OR^{B1}$, —$OC(=O)SR^{B1}$, —$OC(=O)N(R^{B1})_2$, —$OC(=NR^{B1})R^{B1}$, —$OC(=NR^{B1})OR^{B1}$, —$OC(=NR^{B1})N(R^{B1})_2$, —$OC(=S)R^{B1}$, —$OC(=S)OR^{B1}$, —$OC(=S)SR^{B1}$, —$OC(=S)N(R^{B1})_2$, —$ON(R^{B1})_2$, —$OS(=O)R^{B1}$, —$OS(=O)OR^{B1}$, —$OS(=O)SR^{B1}$, —$OS(=O)N(R^{B1})_2$, —$OS(=O)_2R^{B1}$, —$OS(=O)_2OR^{B1}$, —$OS(=O)_2SR^{B1}$, —$OS(=O)_2N(R^{B1})_2$, —$OP(=O)(R^{B1})_2$, —$OP(=O)R^{B1}(OR^{B1})$, —$OP(=O)(OR^{B1})_2$, —$S(=O)R^{B1}$, —$S(=O)OR^{B1}$, —$S(=O)N(R^{B1})_2$, —$S(=O)_2R^{B1}$, —$S(=O)_2OR^{B1}$, —$S(=O)_2N(R^{B1})_2$, —$SC(=O)R^{B1}$, —$SC(=O)OR^{B1}$, —$SC(=O)SR^{B1}$, —$SC(=O)N(R^{B1})_2$, —$SC(=S)R^{B1}$, —$SC(=S)OR^{B1}$, —$SC(=S)SR^{B1}$, —$SC(=S)N(R^{B1})_2$, —$P(=O)(R^{B1})_2$, —$P(=O)(OR^{B1})_2$, —$P(=O)R^{B1}(OR^{B1})$, and —$P(=O)_2$, wherein each occurrence of $R^{B1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B1}$ groups are joined to form an optionally substituted heterocyclic ring;

each occurrence of $R^C$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{C1}$, —N(R$^{C1}$)$_2$, —SR$^{C1}$, —CN, —C(=NR$^{C1}$)R$^{C1}$, —C(=NR$^{C1}$)OR$^{C1}$, —C(=NR$^{C1}$)SR$^{C1}$, —C(=NR$^{C1}$)N(R$^{C1}$)$_2$, —C(=S)R$^{C1}$, —C(=S)OR$^{C1}$, —C(=S)SR$^{C1}$, —C(=S)N(R$^{C1}$)$_2$, —NO$_2$, —N$_3$, —N(R$^{C1}$)$_3$$^+$F$^-$, —N(R$^{C1}$)$_3$$^+$Cl$^-$, —N(R$^{C1}$)$_3$$^+$Br$^-$, —N(R$^{C1}$)$_3$$^+$I$^-$, —N(OR$^{C1}$)R$^{C1}$, —NR$^{C1}$C(=O)R$^{C1}$, —NR$^{C1}$C(=O)OR$^{C1}$, —NR$^{C1}$C(=O)SR$^{C1}$, —NR$^{C1}$C(=O)N(R$^{C1}$)$_2$, —NR$^{C1}$C(=S)R$^{C1}$, —NR$^{C1}$C(=S)OR$^{C1}$, —NR$^{C1}$C(=S)SR$^{C1}$, —NR$^{C1}$C(=S)N(R$^{C1}$)$_2$, —NR$^{C1}$C(=NR$^{C1}$)R$^{C1}$, —NR$^{C1}$C(=NR$^{C1}$)OR$^{C1}$, —NR$^{C1}$C(=NR$^{C1}$)SR$^{C1}$, —NR$^{C1}$C(=NR$^{C1}$)N(R$^{C1}$)$_2$, —NR$^{C1}$S(=O)$_2$R$^{C1}$, —NR$^{C1}$S(=O)$_2$OR$^{C1}$, —NR$^{C1}$S(=O)$_2$SR$^{C1}$, —NR$^{C1}$S(=O)$_2$N(R$^{C1}$)$_2$, —NR$^{C1}$S(=O)R$^{C1}$, —NR$^{C1}$S(=O)OR$^{C1}$, —NR$^{C1}$S(=O)SR$^{C1}$, —NR$^{C1}$S(=O)N(R$^{C1}$)$_2$, —NR$^{C1}$P(=O), —NR$^{C1}$P(=O)$_2$, —NR$^{C1}$P(=O)(R$^{C1}$)$_2$, —NR$^{C1}$P(=O)R$^{C1}$(OR$^{C1}$), —NR$^{C1}$P(=O)(OR$^{C1}$)R$^{C1}$, —OC(=O)R$^{C1}$, —OC(=O)OR$^{C1}$, —OC(=O)SR$^{C1}$, —OC(=O)N(R$^{C1}$)$_2$, —OC(=NR$^{C1}$)R$^{C1}$, —OC(=NR$^{C1}$)OR$^{C1}$, —OC(=NR$^{C1}$)N(R$^{C1}$)$_2$, —OC(=S)R$^{C1}$, —OC(=S)OR$^{C1}$, —OC(=S)SR$^{C1}$, —OC(=S)N(R$^{C1}$)$_2$, —ON(R$^{C1}$)$_2$, —OS(=O)R$^{C1}$, —OS(=O)OR$^{C1}$, —OS(=O)SR$^{C1}$, —OS(=O)N(R$^{C1}$)$_2$, —OS(=O)$_2$R$^{C1}$, —OS(=O)$_2$OR$^{C1}$, —OS(=O)$_2$SR$^{C1}$, —OS(=O)$_2$N(R$^{C1}$)$_2$, —OP(=O)(R$^{C1}$)$_2$, —OP(=O)R$^{C1}$(OR$^{C1}$), —OP(=O)(OR$^{C1}$)$_2$, —S(=O)R$^{C1}$, —S(=O)OR$^{C1}$, —S(=O)N(R$^{C1}$)$_2$, —S(=O)$_2$R$^{C1}$, —S(=O)$_2$OR$^{C1}$, —S(=O)$_2$N(R$^{C1}$)$_2$, —SC(=O)R$^{C1}$, —SC(=O)OR$^{C1}$, —SC(=O)SR$^{C1}$, —SC(=O)N(R$^{C1}$)$_2$, —SC(=S)R$^{C1}$, —SC(=S)OR$^{C1}$, —SC(=S)SR$^{C1}$, —SC(=S)N(R$^{C1}$)$_2$, —P(=O)(R$^{C1}$)$_2$, —P(=O)(OR$^{C1}$)$_2$, —P(=O)R$^{C1}$(OR$^{C1}$), and —P(=O)$_2$, wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{C1}$ groups are joined to form an optionally substituted heterocyclic ring;

each occurrence of R$^D$ is independently selected from the group consisting of hydrogen; optionally substituted alkyl; optionally substituted alkenyl; optionally substituted alkynyl; optionally substituted carbocyclyl; optionally substituted heterocyclyl; optionally substituted aryl; optionally substituted heteroaryl; a nitrogen protecting group when attached to a nitrogen atom; an oxygen protecting group when attached to an oxygen atom; and —C(=O)R$^{D1}$, wherein R$^{D1}$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —N(R$^{D1a}$)$_2$, —OR$^{D1a}$, or —SR$^{D1a}$, wherein each occurrence of R$^{D1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{D1a}$ groups are joined to form an optionally substituted heterocyclic ring; or two R$^D$ groups are joined to form an optionally substituted heterocyclic ring;

j is 0, 1, 2, 3, or 4;
k is 0, 1, 2, 3, 4, or 5; and
m is 0, 1, 2, 3, 4, or 5.

In another aspect, the present invention provides pharmaceutical compositions including a compound of the invention, or a pharmaceutically acceptable salt, tautomer, stereoisomer, solvate, hydrate, or polymorph thereof, and optionally a pharmaceutically acceptable excipient.

In still another aspect, the present invention provides methods of inhibiting histone deacetylase. In certain embodiments, these methods include contacting the histone deacetylase with an inventive compound, or a pharmaceutically acceptable salt, tautomer, stereoisomer, solvate, hydrate, or polymorph thereof, or a pharmaceutical composition of the invention.

In yet another aspect, the present invention provides methods of treating a proliferative disease (e.g., cancer, benign neoplasm, angiogenesis, inflammatory disease, or autoimmune disease) in a subject. In certain embodiments, the methods of treating the proliferative disease include administering to the subject a therapeutically effective amount of an inventive compound, or a pharmaceutically acceptable salt, tautomer, stereoisomer, solvate, hydrate, or polymorph thereof, or a pharmaceutical composition of the invention.

In yet another aspect, the present invention provides kits for treating a proliferative disease in a subject. In certain embodiments, the kits include a first container including a therapeutically effective amount of an inventive compound, or a pharmaceutically acceptable salt, tautomer, stereoisomer, solvate, hydrate, or polymorph thereof, or a pharmaceutical composition of the invention. The kits may further include instructions for administering the compound, or the pharmaceutically acceptable salt, tautomer, stereoisomer, solvate, hydrate, or polymorph thereof, or the pharmaceutical composition, to the subject to treat the proliferative disease.

The details of various embodiments of the invention are set forth herein. Other features, objects, and advantages of the invention will be apparent from the Detailed Description, Figures, Examples, and Claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers". When a compound has an asymmetric center, for example, a carbon atom of the compound is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates plane polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGrawHill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched," as used herein, means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the depicted structures that differ only in the replacement of hydrogen by deuterium or tritium, or the replacement of a carbon by $^{13}C$ or $^{14}C$ are within the scope of this invention. Such compounds are useful, for example, as analytical tools, as probes in biological assays, or as therapeutic agents in accordance with the present invention.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The terms "purified," "substantially purified," and "isolated" as used herein refer to a compound useful in the present invention being free of other, dissimilar compounds with which the compound is normally associated in its natural state, so that the compound comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample or composition. In one embodiment, these terms refer to the compound comprising at least 95%, 98%, 99%, or 99.9% of the mass, by weight, of a given sample or composition.

The term "acyl," as used herein, refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(NR^{X1})R^{X1}$, $-C(NR^{X1})OR^{X1}$, $C(NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula ($OR^i$), wherein $R^i$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Exemplary carbon atom substituents include, but are not limited to, halogen, —CN, —NO$_2$, —N$_3$, —SO$_2$H, —SO$_3$H, —OH, —OR, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ff}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O) (OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 Ru groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of Ru is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C (=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

The term "amino," as used herein, refers to a group of the formula (—NH$_2$). A "substituted amino" refers either to a mono-substituted amine (—NHR$^h$) of a disubstituted amine (—NR$^h{}_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the disubstituted amino group (—NR$^h{}_2$) form a 5- to 6-membered heterocyclic ring.

The term "alkoxy" refers to a "substituted hydroxyl" of the formula (—OR$^i$), wherein R$^i$ is an optionally substituted alkyl group as defined herein, and the oxygen moiety is directly attached to the parent molecule.

The term "alkylthioxy" refers to a "substituted thiol" of the formula (—SR$^r$), wherein R$^r$ is an optionally substituted alkyl group as defined herein, and the sulfur moiety is directly attached to the parent molecule.

The term "alkylamino" refers to a "substituted amino" of the formula (—NR$^h{}_2$), wherein R$^h$ is, independently, a hydrogen or an optionally substituted alkyl group as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic C$_4$-C$_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. Exemplary arylalkyl groups are benzyl and phenethyl.

The term "aryloxy" refers to a "substituted hydroxyl" of the formula ($-OR^i$), wherein $R^i$ is an optionally substituted aryl group as defined herein, and the oxygen moiety is directly attached to the parent molecule.

The term "arylamino," refers to a "substituted amino" of the formula ($-NR^h_2$), wherein $R^h$ is, independently, a hydrogen or an optionally substituted aryl group as defined herein, and the nitrogen moiety is directly attached to the parent molecule.

The term "arylthioxy" refers to a "substituted thiol" of the formula ($-SR^r$), wherein $R^r$ is an optionally substituted aryl group as defined herein, and the sulfur moiety is directly attached to the parent molecule.

The term "azido," as used herein, refers to a group of the formula ($-N_3$).

The term "cyano," as used herein, refers to a group of the formula ($-CN$).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula ($-NR^h_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula ($-OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula ($-SR^r$), wherein $R^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiazolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the ($-NR^h{}_2$), wherein $R^h$ is, independently, hydrogen or an optionally substituted heteroaryl group, as defined herein, and the nitrogen moiety is directly attached to the parent molecule.

The term "heteroaryloxy" refers to a "substituted hydroxyl" of the formula ($-OR^i$), wherein $R^i$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxy," or "hydroxyl," as used herein, refers to a group of the formula (—OH). A "substituted hydroxyl" refers to a group of the formula ($-OR^i$), wherein $R^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula ($=NR^r$), wherein $R^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein $R^r$ is hydrogen.

The term "isocyano," as used herein, refers to a group of the formula (—NC).

The term "nitro," as used herein, refers to a group of the formula ($-NO_2$).

The term "oxo," as used herein, refers to a group of the formula (=O).

The term "stable moiety," as used herein, preferably refers to a moiety which possess stability sufficient to allow manufacture, and which maintains its integrity for a sufficient period of time to be useful for the purposes detailed herein.

A "protecting group," as used herein, is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference. Suitable "amino-protecting groups" (also referred to as "nitrogen protecting groups") include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10, 10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "hydroxyl protecting group" (also referred to as an "oxygen protecting group") as used herein, is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

As used herein, the term "pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., $Ca(OH)_2$), magnesium (by using, e.g., $Mg(OH)_2$ and magnesium acetate), zinc, (by using, e.g., $Zn(OH)_2$ and zinc acetate), and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids (e.g., 1-glycine and 1-arginine) and amino acids which may be zwitterionic at neutral pH (e.g., betaine (N,N,N-trimethylglycine)) are also contemplated.

The term "tautomer" refers to a particular isomer of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, lactam-lactim forms, ketene-ynol forms, enamine-enamine forms, and pyridione-hydroxypyridine forms.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

"Solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

"Hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "subject," as used herein, refers to any animal. In certain embodiments, the subject is a mammal. In certain embodiments, the subject is a human (e.g., a man, a woman, or a child). The human may be of either sex and may be at any stage of development. In certain embodiments, the subject has been diagnosed with the condition or disease to be treated. In other embodiments, the subject is at risk of developing the condition or disease. In certain embodiments, the subject is an experimental animal (e.g., mouse, rat, rabbit, dog, pig, or primate). The experimental animal may be genetically engineered. In certain embodiments, the subject is a domesticated animal (e.g., dog, cat, bird, horse, cow, goat, sheep).

The terms "administer," "administering," or "administration," as used herein refers to implanting, absorbing, ingesting, injecting, or inhaling an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, "condition," "disease," and "disorder" are used interchangeably.

An "effective amount" of a compound of the present invention or a pharmaceutical composition thereof refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutically and prophylactically effective amounts.

A "therapeutically effective amount" of a compound of the present invention or a pharmaceutical composition thereof is an amount sufficient to provide a therapeutic benefit in the treatment of a condition, e.g., a proliferative disease, or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

A "prophylactically effective amount" of a compound of the present invention is an amount sufficient to prevent a condition, e.g., a proliferative disease, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

"Angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fascilitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain Barre syndrome, Hashimoto's thyroiditis, and cardiomyopathy.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

A "protein" or "peptide" comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

DETAILED DESCRIPTION OF CERTAIN EMBODIMENTS OF THE INVENTION

Figure 1:
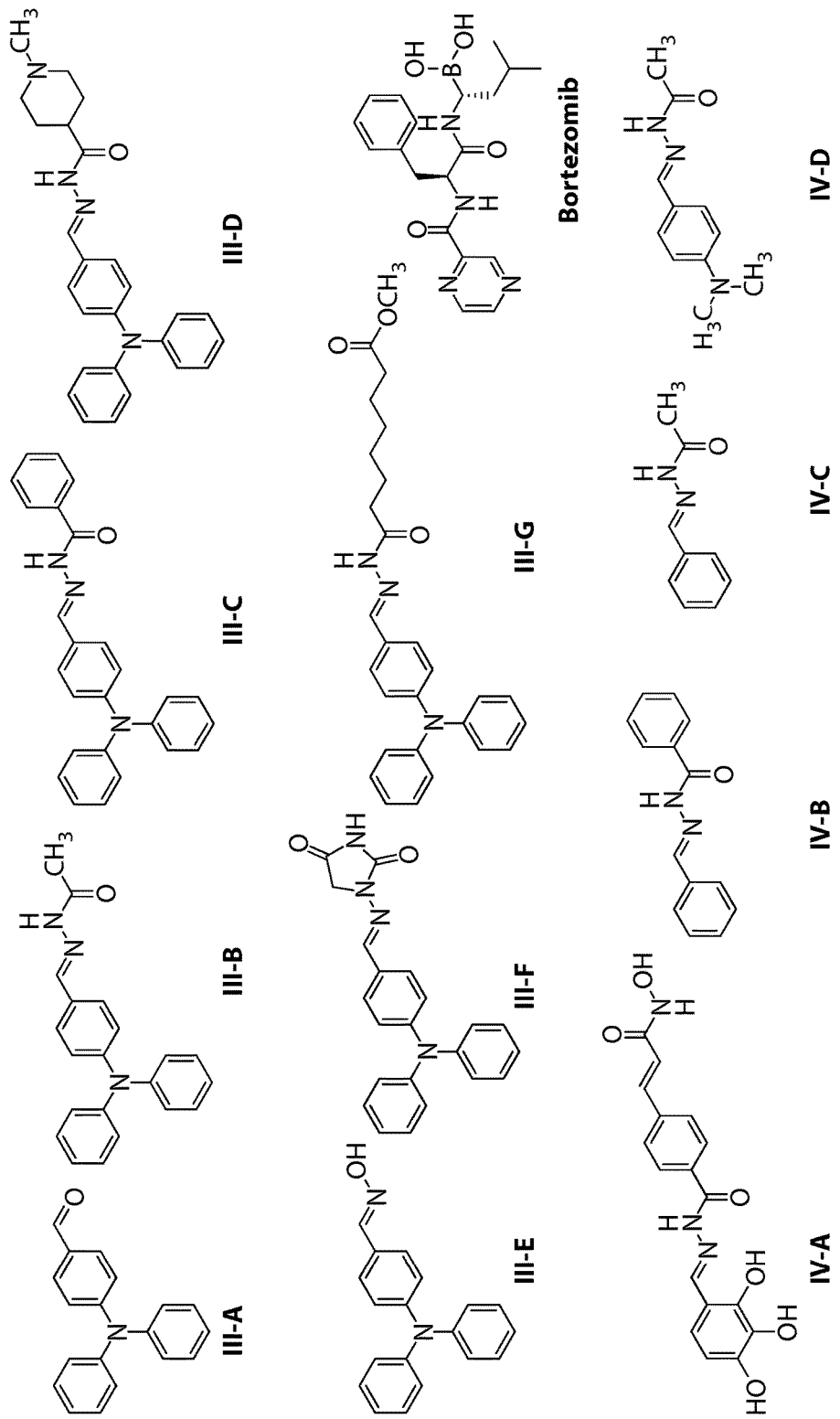
FIG. 1 shows the chemical structures of certain compounds.

As discussed above, there remains a need for the development of novel compounds that can inhibit immune suppression, induce apoptosis, and/or down-regulate certain proteins for the treatment of proliferative diseases (e.g., cancers (e.g., breast cancer, prostate cancer, lung cancer, and ovarian cancer), benign neoplasms, angiogenesis, inflammatory diseases, and autoimmune diseases) in a subject. The present invention provides novel compounds, pharmaceutical compositions, methods, uses, and kits, which are useful for treating the proliferative diseases.

Compounds

The present invention provides compounds of Formula (I):

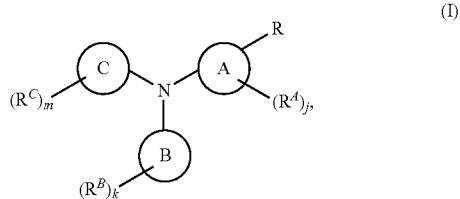

and pharmaceutically acceptable salts, tautomers, stereoisomers, solvates, hydrates, and polymorphs thereof, wherein:

Rings A, B, and C are each independently an aryl ring or heteroaryl ring;

R is a group of formula:

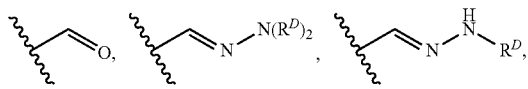

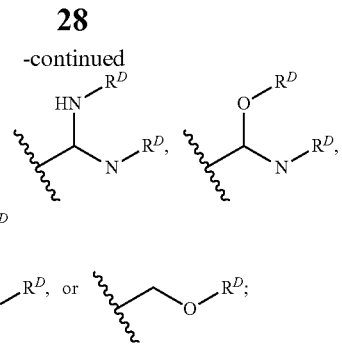

each occurrence of $R^A$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A1})_2$, $-SR^{A1}$, $-CN$, $-C(=NR^{A1})R^{A1}$, $-C(=NR^{A1})OR^{A1}$, $-C(=NR^{A1})SR^{A1}$, $-C(=NR^{A1})N(R^{A1})_2$, $-C(=S)R^{A1}$, $-C(=S)OR^{A1}$, $-C(=S)SR^{A1}$, $-C(=S)N(R^{A1})_2$, $-NO_2$, $-N_3$, $-N(R^{A1})_3{}^+F^-$, $-N(R^{A1})_3{}^+Cl^-$, $-N(R^{A1})_3{}^+Br^-$, $-N(R^{A1})_3{}^+I^-$, $-N(OR^{A1})R^{A1}$, $-NR^{A1}C(=O)R^{A1}$, $-NR^{A1}C(=O)OR^{A1}$, $-NR^{A1}C(=O)SR^{A1}$, $-NR^{A1}C(=O)N(R^{A1})_2$, $-NR^{A1}C(=S)R^{A1}$, $-NR^{A1}C(=S)OR^{A1}$, $-NR^{A1}C(=S)SR^{A1}$, $-NR^{A1}C(=S)N(R^{A1})_2$, $-NR^{A1}C(=NR^{A1})R^{A1}$, $-NR^{A1}C(=NR^{A1})OR^{A1}$, $-NR^{A1}C(=NR^{A1})SR^{A1}$, $-NR^{A1}C(=NR^{A1})N(R^{A1})_2$, $-NR^{A1}S(=O)_2R^{A1}$, $-NR^{A1}S(=O)_2OR^{A1}$, $-NR^{A1}S(=O)_2SR^{A1}$, $-NR^{A1}S(=O)_2N(R^{A1})_2$, $-NR^{A1}S(=O)R^{A1}$, $-NR^{A1}S(=O)OR^{A1}$, $-NR^{A1}S(=O)SR^{A1}$, $-NR^{A1}S(=O)N(R^{A1})_2$, $-NR^{A1}P(=O)$, $-NR^{A1}P(=O)_2$, $-NR^{A1}P(=O)(R^{A1})_2$, $-NR^{A1}P(=O)R^{A1}(OR^{A1})$, $-NR^{A1}P(=O)(OR^{A1})_2$, $-OC(=O)R^{A1}$, $-OC(=O)OR^{A1}$, $-OC(=O)SR^{A1}$, $-OC(=O)N(R^{A1})_2$, $-OC(=NR^{A1})R^{A1}$, $-OC(=NR^{A1})OR^{A1}$, $-OC(=NR^{A1})N(R^{A1})_2$, $-OC(=S)R^{A1}$, $-OC(=S)OR^{A1}$, $-OC(=S)SR^{A1}$, $-OC(=S)N(R^{A1})_2$, $-ON(R^{A1})_2$, $-OS(=O)R^{A1}$, $-OS(=O)OR^{A1}$, $-OS(=O)SR^{A1}$, $-OS(=O)N(R^{A1})_2$, $-OS(=O)_2R^{A1}$, $-OS(=O)_2OR^{A1}$, $-OS(=O)_2SR^{A1}$, $-OS(=O)_2N(R^{A1})_2$, $-OP(=O)(R^{A1})_2$, $-OP(=O)R^{A1}(OR^{A1})$, $-OP(=O)(OR^{A1})_2$, $-S(=O)R^{A1}$, $-S(=O)OR^{A1}$, $-S(=O)N(R^{A1})_2$, $-S(=O)_2R^{A1}$, $-S(=O)_2OR^{A1}$, $-S(=O)_2N(R^{A1})_2$, $-SC(=O)R^{A1}$, $-SC(=O)OR^{A1}$, $-SC(=O)SR^{A1}$, $-SC(=O)N(R^{A1})_2$, $-SC(=S)R^{A1}$, $-SC(=S)OR^{A1}$, $-SC(=S)SR^{A1}$, $-SC(=S)N(R^{A1})_2$, $-P(=O)(R^{A1})_2$, $-P(=O)(OR^{A1})_2$, $-P(=O)R^{A1}(OR^{A1})$, and $-P(=O)_2$, wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;

each occurrence of $R^B$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B1}$, $-N(R^{B1})_2$, $-SR^{B1}$, $-CN$, $-C(=NR^{B1})R^{B1}$, $-C(=NR^{B1})OR$, $-C(=NR^{B1})SR^{B1}$, $-C(=NR^{B1})N$ $(R^{B1})_2$, —C(=S)$R^{B1}$, —C(=S)O$R^{B1}$, —C(=S)S$R^{B1}$, —C(=S)N($R^{B1}$)$_2$, —NO$_2$, —N$_3$, —N($R^{B1}$)$_3^+$F$^-$, —N($R^{B1}$)$_3^+$Cl$^-$, —N($R^{B1}$)$_3^+$Br$^-$, —N($R^{B1}$)$_3^+$I$^-$, —N(O$R^{B1}$)$R^{B1}$, —N$R^{B1}$C(=O)$R^{B1}$, —N$R^{B1}$C(=O)O$R^{B1}$, —N$R^{B1}$C(=O)S$R^{B1}$, —N$R^{B1}$C(=O)N($R^{B1}$)$_2$, —N$R^{B1}$C(=S)$R^{B1}$, —N$R^{B1}$C(=S)O$R^{B1}$, —N$R^{B1}$C(=S)S$R^{B1}$, —N$R^{B1}$C(=S)N($R^{B1}$)$_2$, —N$R^{B1}$C(=N$R^{B1}$)$R^{B1}$, —N$R^{B1}$C(=N$R^{B1}$)O$R^{B1}$, —N$R^{B1}$C(=N$R^{B1}$)S$R^{B1}$, —N$R^{B1}$C(=N$R^{B1}$)N($R^{B1}$)$_2$, —N$R^{B1}$S(=O)$_2$$R^{B1}$, —N$R^{B1}$S(=O)$_2$O$R^{B1}$, —N$R^{B1}$S(=O)$_2$S$R^{B1}$, —N$R^{B1}$S(=O)$_2$N($R^{B1}$)$_2$, —N$R^{B1}$S(=O)$R^{B1}$, —N$R^{B1}$S(=O)O$R^{B1}$, —N$R^{B1}$S(=O)S$R^{B1}$, —N$R^{B1}$S(=O)N($R^{B1}$)$_2$, —N$R^{B1}$P(=O), —N$R^{B1}$P(=O)$_2$, —N$R^{B1}$P(=O)($R^{B1}$)$_2$, —N$R^{B1}$P(=O)$R^{B1}$(O$R^{B1}$), —N$R^{B1}$P(=O)(O$R^{B1}$)$_2$, —OC(=O)$R^{B1}$, —OC(=O)O$R^{B1}$, —OC(=O)S$R^{B1}$, —OC(=O)N($R^{B1}$)$_2$, —OC(=N$R^{B1}$)$R^{B1}$, —OC(=N$R^{B1}$)O$R^{B1}$, —OC(=N$R^{B1}$)N($R^{B1}$)$_2$, —OC(=S)$R^{B1}$, —OC(=S)O$R^{B1}$, —OC(=S)S$R^{B1}$, —OC(=S)N($R^{B1}$)$_2$, —ON($R^{B1}$)$_2$, —OS(=O)$R^{B1}$, —OS(=O)O$R^{B1}$, —OS(=O)S$R^{B1}$, —OS(=O)N($R^{B1}$)$_2$, —OS(=O)$_2$$R^{B1}$, —OS(=O)$_2$O$R^{B1}$, —OS(=O)$_2$S$R^{B1}$, —OS(=O)$_2$N($R^{B1}$)$_2$, —OP(=O)($R^{B1}$)$_2$, —OP(=O)$R^{B1}$(O$R^{B1}$), —OP(=O)(O$R^{B1}$)$_2$, —S(=O)$R^{B1}$, —S(=O)O$R^{B1}$, —S(=O)N($R^{B1}$)$_2$, —S(=O)$_2$$R^{B1}$, —S(=O)$_2$O$R^{B1}$, —S(=O)$_2$N($R^{B1}$)$_2$, —SC(=O)$R^{B1}$, —SC(=O)O$R^{B1}$, —SC(=O)S$R^{B1}$, —SC(=O)N($R^{B1}$)$_2$, —SC(=S)$R^{B1}$, —SC(=S)O$R^{B1}$, —SC(=S)S$R^{B1}$, —SC(=S)N($R^{B1}$)$_2$, —P(=O)($R^{B1}$)$_2$, —P(=O)(O$R^{B1}$)$_2$, —P(=O)$R^{B1}$(O$R^{B1}$), and —P(=O)$_2$, wherein each occurrence of $R^{B1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B1}$ groups are joined to form an optionally substituted heterocyclic ring;

each occurrence of $R^C$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —O$R^{C1}$, —N($R^{C1}$)$_2$, —S$R^{C1}$, —CN, —C(=N$R^{C1}$)$R^{C1}$, —C(=N$R^{C1}$)O$R^{C1}$, —C(=N$R^{C1}$)S$R^{C1}$, —C(=N$R^{C1}$)N($R^{C1}$)$_2$, —C(=S)$R^{C1}$, —C(=S)O$R^{C1}$, —C(=S)S$R^{C1}$, —C(=S)N($R^{C1}$)$_2$, —NO$_2$, —N$_3$, —N($R^{C1}$)$_3^+$F$^-$, —N($R^{C1}$)$_3^+$Cl$^-$, —N($R^{C1}$)$_3^+$Br$^-$, —N($R^{C1}$)$_3^+$I$^-$, —N(O$R^{C1}$)$R^{C1}$, —N$R^{C1}$C(=O)$R^{C1}$, —N$R^{C1}$C(=O)O$R^{C1}$, —N$R^{C1}$C(=O)S$R^{C1}$, —N$R^{C1}$C(=O)N($R^{C1}$)$_2$, —N$R^{C1}$C(=S)$R^{C1}$, —N$R^{C1}$C(=S)O$R^{C1}$, —N$R^{C1}$C(=S)S$R^{C1}$, —N$R^{C1}$C(=S)N($R^{C1}$)$_2$, —N$R^{C1}$C(=N$R^{C1}$)$R^{C1}$, —N$R^{C1}$C(=N$R^{C1}$)O$R^{C1}$, —N$R^{C1}$C(=N$R^{C1}$)S$R^{C1}$, —N$R^{C1}$C(=N$R^{C1}$)N($R^{C1}$)$_2$, —N$R^{C1}$S(=O)$_2$$R^{C1}$, —N$R^{C1}$S(=O)$_2$O$R^{C1}$, —N$R^{C1}$S(=O)$_2$S$R^{C1}$, —N$R^{C1}$S(=O)$_2$N($R^{C1}$)$_2$, —N$R^{C1}$S(=O)$R^{C1}$, —N$R^{C1}$S(=O)O$R^{C1}$, —N$R^{C1}$S(=O)S$R^{C1}$, —N$R^{C1}$S(=O)N($R^{C1}$)$_2$, —N$R^{C1}$P(=O), —N$R^{C1}$P(=O)$_2$, —N$R^{C1}$P(=O)($R^{C1}$)$_2$, —N$R^{C1}$P(=O)$R^{C1}$(O$R^{C1}$), —N$R^{C1}$P(=O)(O$R^{C1}$)$_2$, —OC(=O)$R^{C1}$, —OC(=O)O$R^{C1}$, —OC(=O)S$R^{C1}$, —OC(=O)N($R^{C1}$)$_2$, —OC(=N$R^{C1}$)$R^{C1}$, —OC(=N$R^{C1}$)O$R^{C1}$, —OC(=N$R^{C1}$)N($R^{C1}$)$_2$, —OC(=S)$R^{C1}$, —OC(=S)O$R^{C1}$, —OC(=S)S$R^{C1}$, —OC(=S)N($R^{C1}$)$_2$, —ON($R^{C1}$)$_2$, —OS(=O)$R^{C1}$, —OS(=O)O$R^{C1}$, —OS(=O)S$R^{C1}$, —OS(=O)N($R^{C1}$)$_2$, —OS(=O)$_2$$R^{C1}$, —OS(=O)$_2$O$R^{C1}$, —OS(=O)$_2$S$R^{C1}$, —OS(=O)$_2$N($R^{C1}$)$_2$, —OP(=O)($R^{C1}$)$_2$, —OP(=O)(O$R^{C1}$)$_2$, —OP(=O)$R^{C1}$(O$R^{C1}$), —OP(=O)(O$R^{C1}$)$_2$, —S(=O)$R^{C1}$, —S(=O)O$R^{C1}$, —S(=O)N($R^{C1}$)$_2$, —S(=O)$_2$$R^{C1}$, —S(=O)$_2$O$R^{C1}$, —S(=O)$_2$N($R^{C1}$)$_2$, —SC(=O)$R^{C1}$, —SC(=O)O$R^{C1}$, —SC(=O)S$R^{C1}$, —SC(=O)N($R^{C1}$)$_2$, —SC(=S)$R^{C1}$, —SC(=S)O$R^{C1}$, —SC(=S)S$R^{C1}$, —SC(=S)N($R^{C1}$)$_2$, —P(=O)($R^{C1}$)$_2$, —P(=O)(O$R^{C1}$)$_2$, —P(=O)$R^{C1}$(O$R{c1}$), and —P(=O)$_2$, wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{C1}$ groups are joined to form an optionally substituted heterocyclic ring;

each occurrence of $R^D$ is independently selected from the group consisting of hydrogen; optionally substituted alkyl; optionally substituted alkenyl; optionally substituted alkynyl; optionally substituted carbocyclyl; optionally substituted heterocyclyl; optionally substituted aryl; optionally substituted heteroaryl; a nitrogen protecting group when attached to a nitrogen atom; an oxygen protecting group when attached to an oxygen atom; and —C(=O)$R^{D1}$, wherein $R^{D1}$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —N($R^{D1a}$)$_2$, —O$R^{D1a}$, or —S$R^{D1a}$, wherein each occurrence of $R^{D1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{D1a}$ groups are joined to form an optionally substituted heterocyclic ring; or two $R^D$ groups are joined to form an optionally substituted heterocyclic ring;

j is 0, 1, 2, 3, or 4;

k is 0, 1, 2, 3, 4, or 5; and m is 0, 1, 2, 3, 4, or 5.

In compounds of Formula (I), Ring A is an aryl ring or heteroaryl ring. Ring A is substituted with an R group and may be optionally substituted with one or more substituents $R^A$. The substituent $R^A$ may be attached to a carbon atom or heteroatom of Ring A. In certain embodiments, Ring A is an aryl ring. In certain embodiments, Ring A is a monocyclic aryl ring. In certain embodiments, Ring A is a phenyl ring. In certain embodiments, Ring A is an aryl ring fused with one or more carbocyclic, heterocyclic, aryl, or heteroaryl groups. In certain embodiments, Ring A is a bicyclic aryl ring. In certain embodiments, Ring A is a naphthyl ring. In certain embodiments, Ring A is a tricyclic aryl ring. In certain embodiments, Ring A is an anthracenyl ring.

Ring A of Formula (I) may also be a heteroaryl ring. In certain embodiments, Ring A is a monocyclic heteroaryl ring. In certain embodiments, Ring A is a monocyclic heteroaryl ring having one heteroatom in the backbone of the heteroaryl ring. In certain embodiments, Ring A is a monocyclic heteroaryl ring having two heteroatoms in the backbone of the heteroaryl ring. In certain embodiments, Ring A is a monocyclic heteroaryl ring having three heteroatoms in the backbone of the heteroaryl ring. In certain embodiments, Ring A is a 5-membered heteroaryl ring. In certain embodiments, Ring A is a pyrrolyl ring. In certain embodiments, Ring A is a furanyl ring. In certain embodiments, Ring A is a thienyl ring. In certain embodiments, Ring A is an imidazolyl ring. In certain embodiments, Ring A is a pyrazolyl ring. In certain embodiments, Ring A is an oxazolyl ring. In certain embodiments, Ring A is an isoxazolyl ring. In certain embodiments, Ring A is a thiazolyl ring. In certain embodiments, Ring A is an isothiazolyl ring. In certain embodiments, Ring A is a triazolyl ring. In certain embodiments, Ring A is a furazanyl ring. In certain embodiments, Ring A is an oxadiazolyl ring. In certain embodiments, Ring A is a thiadiazolyl ring. In certain embodiments, Ring A is a tetrazolyl ring. In certain embodiments, Ring A is a 6-membered heteroaryl ring. In certain embodiments, Ring A is a pyridyl ring. In certain embodiments, Ring A is a heteroaryl ring fused with one or more carbocyclic, heterocyclic, aryl, or heteroaryl groups. In certain embodiments, Ring A is a bicyclic heteroaryl ring. In certain embodiments, Ring A is a bicyclic heteroaryl ring having one heteroatom in the backbone of the heteroaryl ring. In certain embodiments, Ring A is a bicyclic heteroaryl ring having two heteroatoms in the backbone of the heteroaryl ring. In certain embodiments, Ring A is a bicyclic heteroaryl ring having three heteroatoms in the backbone of the heteroaryl ring. In certain embodiments, Ring A is a bicyclic heteroaryl ring having four heteroatoms in the backbone of the heteroaryl ring. In certain embodiments, Ring A is a tricyclic heteroaryl ring. In certain embodiments, Ring A is a tricyclic heteroaryl ring having one heteroatom in the backbone of the heteroaryl ring. In certain embodiments, Ring A is a tricyclic heteroaryl ring having two heteroatoms in the backbone of the heteroaryl ring. In certain embodiments, Ring A is a tricyclic heteroaryl ring having three heteroatoms in the backbone of the heteroaryl ring. In certain embodiments, Ring A is a tricyclic heteroaryl ring having four heteroatoms in the backbone of the heteroaryl ring. In certain embodiments, Ring A is a tricyclic heteroaryl ring having five heteroatoms in the backbone of the heteroaryl ring.

Ring A of Formula (I) may also be a heteroaryl ring fused with a phenyl ring. In certain embodiments, Ring A is an indolyl ring. In certain embodiments, Ring A is an isoindolyl ring. In certain embodiments, Ring A is an indazolyl ring. In certain embodiments, Ring A is a benzothienyl ring. In certain embodiments, Ring A is an isobenzothienyl ring. In certain embodiments, Ring A is a benzofuranyl ring. In certain embodiments, Ring A is a benzoisofuranyl ring. In certain embodiments, Ring A is a benzimidazolyl ring. In certain embodiments, Ring A is a benzoxazolyl ring. In certain embodiments, Ring A is a benzisoxazolyl ring. In certain embodiments, Ring A is a benzothiazolyl ring. In certain embodiments, Ring A is a benzisothiazolyl ring. In certain embodiments, Ring A is a benzotriazolyl ring. In certain embodiments, Ring A is a benzoxadiazolyl ring. In certain embodiments, Ring A is a quinolinyl ring. In certain embodiments, Ring A is an isoquinolinyl ring. In certain embodiments, Ring A is a cinnolinyl ring. In certain embodiments, Ring A is a quinoxalinyl ring. In certain embodiments, Ring A is a phthalazinyl ring. In certain embodiments, Ring A is a quinazolinyl ring.

In compounds of Formula (I), Ring B is an aryl ring or heteroaryl ring. Ring B may be unsubstituted or substituted with one or more substituents $R^B$. The substituent $R^B$ may be attached to a carbon atom or heteroatom of Ring B. In certain embodiments, Ring B is an aryl ring. In certain embodiments, Ring B is a monocyclic aryl ring. In certain embodiments, Ring B is a phenyl ring. In certain embodiments, Ring B is an aryl ring fused with one or more carbocyclic, heterocyclic, aryl, or heteroaryl groups. In certain embodiments, Ring B is a bicyclic aryl ring. In certain embodiments, Ring B is a naphthyl ring. In certain embodiments, Ring B is a tricyclic aryl ring. In certain embodiments, Ring B is an anthracenyl ring.

Ring B of Formula (I) may also be a heteroaryl ring. In certain embodiments, Ring B is a monocyclic heteroaryl ring. In certain embodiments, Ring B is a monocyclic heteroaryl ring having one heteroatom in the backbone of the heteroaryl ring. In certain embodiments, Ring B is a monocyclic heteroaryl ring having two heteroatoms in the backbone of the heteroaryl ring. In certain embodiments, Ring B is a monocyclic heteroaryl ring having three heteroatoms in the backbone of the heteroaryl ring. In certain embodiments, Ring B is a 5-membered heteroaryl ring. In certain embodiments, Ring B is a pyrrolyl ring. In certain embodiments, Ring B is a furanyl ring. In certain embodiments, Ring B is a thienyl ring. In certain embodiments, Ring B is an imidazolyl ring. In certain embodiments, Ring B is a pyrazolyl ring. In certain embodiments, Ring B is an oxazolyl ring. In certain embodiments, Ring B is an isoxazolyl ring. In certain embodiments, Ring B is a thiazolyl ring. In certain embodiments, Ring B is an isothiazolyl ring. In certain embodiments, Ring B is a triazolyl ring. In certain embodiments, Ring B is a furazanyl ring. In certain embodiments, Ring B is an oxadiazolyl ring. In certain embodiments, Ring B is a thiadiazolyl ring. In certain embodiments, Ring B is a tetrazolyl ring. In certain embodiments, Ring B is a 6-membered heteroaryl ring. In certain embodiments, Ring B is a pyridyl ring. In certain embodiments, Ring B is a heteroaryl ring fused with one or more carbocyclic, heterocyclic, aryl, or heteroaryl groups. In certain embodiments, Ring B is a bicyclic heteroaryl ring. In certain embodiments, Ring B is a bicyclic heteroaryl ring having one heteroatom in the backbone of the heteroaryl ring. In certain embodiments, Ring B is a bicyclic heteroaryl ring having two heteroatoms in the backbone of the heteroaryl ring. In certain embodiments, Ring B is a bicyclic heteroaryl ring having three heteroatoms in the backbone of the heteroaryl ring. In certain embodiments, Ring B is a bicyclic heteroaryl ring having four heteroatoms in the backbone of the heteroaryl ring. In certain embodiments, Ring B is a tricyclic heteroaryl ring. In certain embodiments, Ring B is a tricyclic heteroaryl ring having one heteroatom in the backbone of the heteroaryl ring. In certain embodiments, Ring B is a tricyclic heteroaryl ring having two heteroatoms in the backbone of the heteroaryl ring. In certain embodiments, Ring B is a tricyclic heteroaryl ring having three heteroatoms in the backbone of the heteroaryl ring. In certain embodiments, Ring B is a tricyclic heteroaryl ring having four heteroatoms in the backbone of the heteroaryl ring. In certain embodiments, Ring B is a tricyclic heteroaryl ring having five heteroatoms in the backbone of the heteroaryl ring.

Ring B of Formula (I) may also be a heteroaryl ring fused with a phenyl ring. In certain embodiments, Ring B is an indolyl ring. In certain embodiments, Ring B is an isoindolyl ring. In certain embodiments, Ring B is an indazolyl ring. In certain embodiments, Ring B is a benzothienyl ring. In certain embodiments, Ring B is an isobenzothienyl ring. In certain embodiments, Ring B is a benzofuranyl ring. In certain embodiments, Ring B is a benzoisofuranyl ring. In certain embodiments, Ring B is a benzimidazolyl ring. In certain embodiments, Ring B is a benzoxazolyl ring. In certain embodiments, Ring B is a benzisoxazolyl ring. In certain embodiments, Ring B is a benzothiazolyl ring. In certain embodiments, Ring B is a benzisothiazolyl ring. In certain embodiments, Ring B is a benzotriazolyl ring. In certain embodiments, Ring B is a benzoxadiazolyl ring. In certain embodiments, Ring B is a quinolinyl ring. In certain embodiments, Ring B is an isoquinolinyl ring. In certain embodiments, Ring B is a cinnolinyl ring. In certain embodiments, Ring B is a quinoxalinyl ring. In certain embodiments, Ring B is a phthalazinyl ring. In certain embodiments, Ring B is a quinazolinyl ring.

In compounds of Formula (I), Ring C is an aryl ring or heteroaryl ring. Ring C may be unsubstituted or substituted with one or more substituents $R^C$. The substituent $R^C$ may be attached to a carbon atom or heteroatom of Ring C. In certain embodiments, Ring C is an aryl ring. In certain embodiments, Ring C is a monocyclic aryl ring. In certain embodiments, Ring C is a phenyl ring. In certain embodiments, Ring C is an aryl ring fused with one or more carbocyclic, heterocyclic, aryl, or heteroaryl groups. In certain embodiments, Ring C is a bicyclic aryl ring. In certain embodiments, Ring C is a naphthyl ring. In certain embodiments, Ring C is a tricyclic aryl ring. In certain embodiments, Ring C is an anthracenyl ring.

Ring C of Formula (I) may also be a heteroaryl ring. In certain embodiments, Ring C is a monocyclic heteroaryl ring. In certain embodiments, Ring C is a monocyclic heteroaryl ring having one heteroatom in the backbone of the heteroaryl ring. In certain embodiments, Ring C is a monocyclic heteroaryl ring having two heteroatoms in the backbone of the heteroaryl ring. In certain embodiments, Ring C is a monocyclic heteroaryl ring having three heteroatoms in the backbone of the heteroaryl ring. In certain embodiments, Ring C is a 5-membered heteroaryl ring. In certain embodiments, Ring C is a pyrrolyl ring. In certain embodiments, Ring C is a furanyl ring. In certain embodiments, Ring C is a thienyl ring. In certain embodiments, Ring C is an imidazolyl ring. In certain embodiments, Ring C is a pyrazolyl ring. In certain embodiments, Ring C is an oxazolyl ring. In certain embodiments, Ring C is an isoxazolyl ring. In certain embodiments, Ring C is a thiazolyl ring. In certain embodiments, Ring C is an isothiazolyl ring. In certain embodiments, Ring C is a triazolyl ring. In certain embodiments, Ring C is a furazanyl ring. In certain embodiments, Ring C is an oxadiazolyl ring. In certain embodiments, Ring C is a thiadiazolyl ring. In certain embodiments, Ring C is a tetrazolyl ring. In certain embodiments, Ring C is a 6-membered heteroaryl ring. In certain embodiments, Ring C is a pyridyl ring. In certain embodiments, Ring C is a heteroaryl ring fused with one or more carbocyclic, heterocyclic, aryl, or heteroaryl groups. In certain embodiments, Ring C is a bicyclic heteroaryl ring. In certain embodiments, Ring C is a bicyclic heteroaryl ring having one heteroatom in the backbone of the heteroaryl ring. In certain embodiments, Ring C is a bicyclic heteroaryl ring having two heteroatoms in the backbone of the heteroaryl ring. In certain embodiments, Ring C is a bicyclic heteroaryl ring having three heteroatoms in the backbone of the heteroaryl ring. In certain embodiments, Ring C is a bicyclic heteroaryl ring having four heteroatoms in the backbone of the heteroaryl ring. In certain embodiments, Ring C is a tricyclic heteroaryl ring. In certain embodiments, Ring C is a tricyclic heteroaryl ring having one heteroatom in the backbone of the heteroaryl ring. In certain embodiments, Ring C is a tricyclic heteroaryl ring having two heteroatoms in the backbone of the heteroaryl ring. In certain embodiments, Ring C is a tricyclic heteroaryl ring having three heteroatoms in the backbone of the heteroaryl ring. In certain embodiments, Ring C is a tricyclic heteroaryl ring having four heteroatoms in the backbone of the heteroaryl ring. In certain embodiments, Ring C is a tricyclic heteroaryl ring having five heteroatoms in the backbone of the heteroaryl ring.

Ring C of Formula (I) may also be a heteroaryl ring fused with a phenyl ring. In certain embodiments, Ring C is an indolyl ring. In certain embodiments, Ring C is an isoindolyl ring. In certain embodiments, Ring C is an indazolyl ring. In certain embodiments, Ring C is a benzothienyl ring. In certain embodiments, Ring C is an isobenzothienyl ring. In certain embodiments, Ring C is a benzofuranyl ring. In certain embodiments, Ring C is a benzoisofuranyl ring. In certain embodiments, Ring C is a benzimidazolyl ring. In certain embodiments, Ring C is a benzoxazolyl ring. In certain embodiments, Ring C is a benzisoxazolyl ring. In certain embodiments, Ring C is a benzothiazolyl ring. In certain embodiments, Ring C is a benzisothiazolyl ring. In certain embodiments, Ring C is a benzotriazolyl ring. In certain embodiments, Ring C is a benzoxadiazolyl ring. In certain embodiments, Ring C is a quinolinyl ring. In certain embodiments, Ring C is an isoquinolinyl ring. In certain embodiments, Ring C is a cinnolinyl ring. In certain embodiments, Ring C is a quinoxalinyl ring. In certain embodiments, Ring C is a phthalazinyl ring. In certain embodiments, Ring C is a quinazolinyl ring.

In certain embodiments, Rings A and B are each an aryl ring. In certain embodiments, Rings A and B are each a monocyclic aryl ring. In certain embodiments, Rings A and B are each a phenyl ring. In certain embodiments, Rings A and B are each an aryl ring fused with one or more carbocyclic, heterocyclic, aryl, or heteroaryl groups. In certain embodiments, Rings A and B are each a bicyclic aryl ring. In certain embodiments, Rings A and B are each a naphthyl ring.

In certain embodiments, Rings A and C are each an aryl ring. In certain embodiments, Rings A and C are each a monocyclic aryl ring. In certain embodiments, Rings A and C are each a phenyl ring. In certain embodiments, Rings A and C are each an aryl ring fused with one or more carbocyclic, heterocyclic, aryl, or heteroaryl groups. In certain embodiments, Rings A and C are each a bicyclic aryl ring. In certain embodiments, Rings A and C are each a naphthyl ring.

In certain embodiments, Rings B and C are each an aryl ring. In certain embodiments, Rings B and C are each a monocyclic aryl ring. In certain embodiments, Rings B and C are each a phenyl ring. In certain embodiments, Rings B and C are each an aryl ring fused with one or more carbocyclic, heterocyclic, aryl, or heteroaryl groups. In certain embodiments, Rings B and C are each a bicyclic aryl ring. In certain embodiments, Rings B and C are each a naphthyl ring.

In certain embodiments, Rings A, B, and C are each an aryl ring. In certain embodiments, Rings A, B, and C are each a monocyclic aryl ring. In certain embodiments, Rings A, B, and C are each a phenyl ring. In certain embodiments, Rings A, B, and C are each an aryl ring fused with one or more carbocyclic, heterocyclic, aryl, or heteroaryl groups. In certain embodiments, Rings A, B, and C are each a bicyclic aryl ring. In certain embodiments, Rings A, B, and C are each a naphthyl ring.

Ring A of Formula (I) is at least substituted with group R. R is a group of formula:

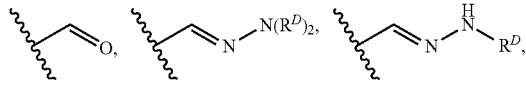

-continued

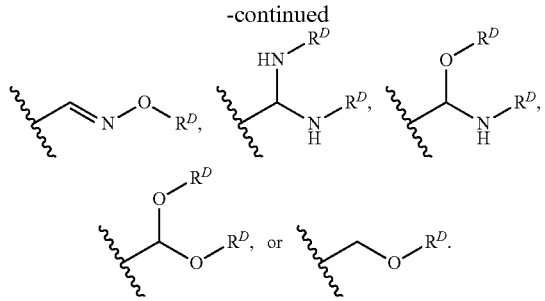

In certain embodiments, R is

In certain embodiments, R is

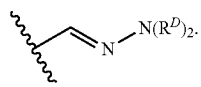

In certain embodiments, R is

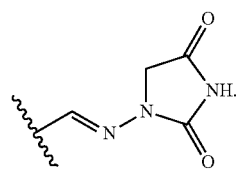 [SMILES: */C=N/N1CC(=O)NC1=O]

In certain embodiments, R is

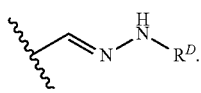

In certain embodiments, R is

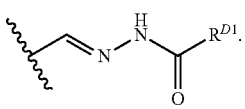

In certain embodiments, R is

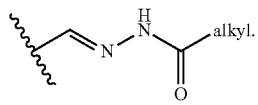

In certain embodiments, R is

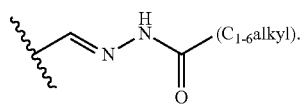

In certain embodiments, R is

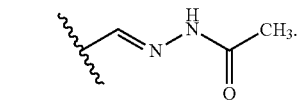 [SMILES: */C=N/NC(C)=O]

In certain embodiments, R is

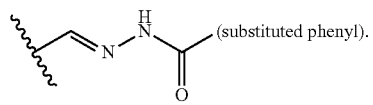

In certain embodiments, R is

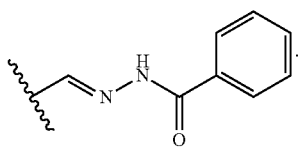 [SMILES: */C=N/NC(=O)c1ccccc1]

In certain embodiments, R is

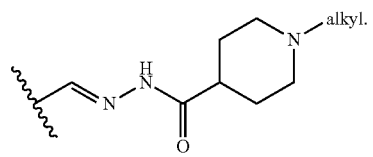

In certain embodiments, R is

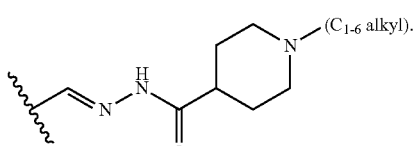

In certain embodiments, R is

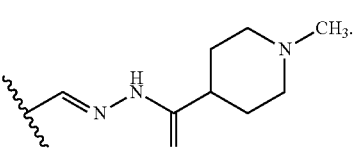

In certain embodiments, R is

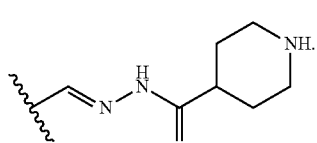

In certain embodiments, R is

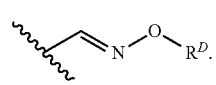

In certain embodiments, R is

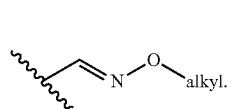alkyl.

In certain embodiments, R is

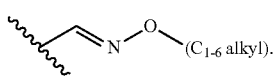(C$_{1-6}$ alkyl).

In certain embodiments, R is

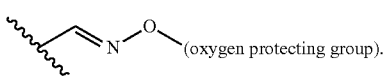(oxygen protecting group).

In certain embodiments, R is

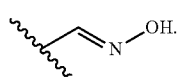

In certain embodiments, R is

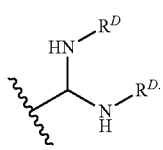

In certain embodiments, R is

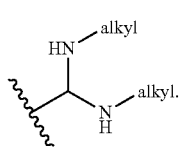

In certain embodiments, R is

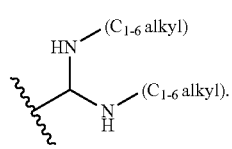

In certain embodiments, R is

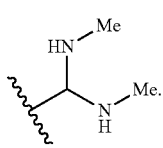

In certain embodiments, R is

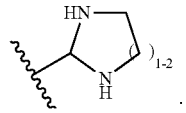

In certain embodiments, R is

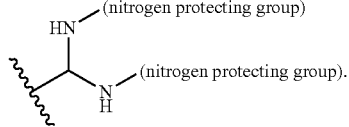

In certain embodiments, R is

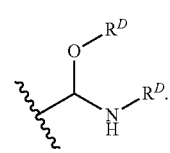

In certain embodiments, R is

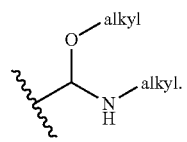

In certain embodiments, R is

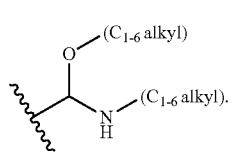

In certain embodiments, R is

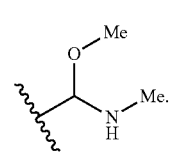 [SMILES: *C(NC)OC]

In certain embodiments, R is

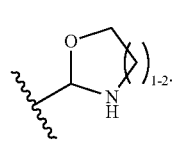

In certain embodiments, R is

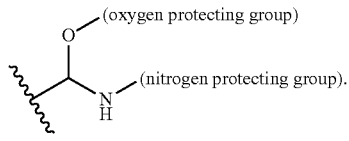

In certain embodiments, R is

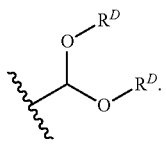

In certain embodiments, R is

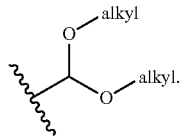

In certain embodiments, R is

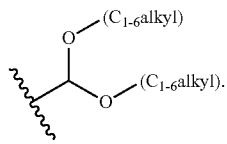

In certain embodiments, R is

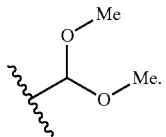

In certain embodiments, R is

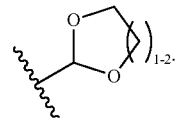

In certain embodiments, R is

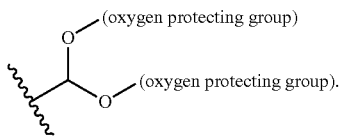

In certain embodiments, R is

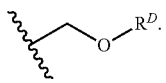

In certain embodiments, R is

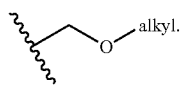

In certain embodiments, R is

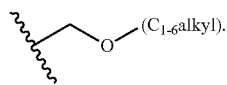

In certain embodiments, R is

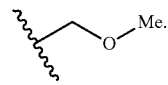

Group R of Formula (I) is substituted with one or more $R^D$ group(s). In certain embodiments, at least one $R^D$ is hydrogen. In certain embodiments, at least one $R^D$ is optionally substituted alkyl. In certain embodiments, at least one $R^D$ is alkyl. In certain embodiments, at least one $R^D$ is optionally substituted $C_{1-6}$ alkyl. In certain embodiments, at least one $R^D$ is $C_{1-6}$ alkyl. In certain embodiments, at least one $R^D$ is methyl. In certain embodiments, at least one $R^D$ is ethyl. In certain embodiments, at least one $R^D$ is propyl. In certain embodiments, at least one $R^D$ is butyl. In certain embodiments, at least one $R^D$ is optionally substituted alkenyl. In certain embodiments, at least one $R^D$ is alkenyl. In certain embodiments, at least one $R^D$ is optionally substituted $C_{1-6}$ alkenyl. In certain embodiments, at least one $R^D$ is $C_{1-6}$ alkenyl. In certain embodiments, at least one $R^D$ is optionally substituted alkynyl. In certain embodiments, at least one $R^D$ is alkynyl. In certain embodiments, at least one $R^D$ is optionally substituted $C_{1-6}$ alkynyl. In certain embodiments, at least one $R^D$ is $C_{1-6}$ alkynyl.

In certain embodiments, at least one $R^D$ is optionally substituted carbocyclyl. In certain embodiments, at least one $R^D$ is carbocyclyl. In certain embodiments, at least one $R^D$ is saturated carbocyclyl. In certain embodiments, at least one $R^D$ is unsaturated carbocyclyl. In certain embodiments, at least one $R^D$ is monocyclic carbocyclyl. In certain embodiments, at least one $R^D$ is 3-membered carbocyclyl. In certain embodiments, at least one $R^D$ is cyclopropyl. In certain embodiments, at least one $R^D$ is 4-membered carbocyclyl. In certain embodiments, at least one $R^D$ is cyclobutyl. In certain embodiments, at least one $R^D$ is 5-membered carbocyclyl. In certain embodiments, at least one $R^D$ is cyclopentyl. In certain embodiments, at least one $R^D$ is 6-membered carbocyclyl. In certain embodiments, at least one $R^D$ is cyclohexyl. In certain embodiments, at least one $R^D$ is 7-membered carbocyclyl. In certain embodiments, at least one $R^D$ is cycloheptyl. In certain embodiments, at least one $R^D$ is 8-membered carbocyclyl. In certain embodiments, at least one $R^D$ is cyclooctyl. In certain embodiments, at least one $R^D$ is bicyclic carbocyclyl. In certain embodiments, at least one $R^D$ is tricyclic carbocyclyl.

In certain embodiments, at least one $R^D$ is optionally substituted heterocyclyl. In certain embodiments, at least one $R^D$ is heterocyclyl. In certain embodiments, at least one $R^D$ is saturated heterocyclyl. In certain embodiments, at least one $R^D$ is unsaturated heterocyclyl. In certain embodiments, at least one $R^D$ is monocyclic heterocyclyl. In certain embodiments, at least one $R^D$ is 3-membered heterocyclyl. In certain embodiments, at least one $R^D$ is 4-membered heterocyclyl. In certain embodiments, at least one $R^D$ is 5-membered heterocyclyl. In certain embodiments, at least one $R^D$ is 6-membered heterocyclyl. In certain embodiments, at least one $R^D$ is 7-membered heterocyclyl. In certain embodiments, at least one $R^D$ is 8-membered heterocyclyl. In certain embodiments, at least one $R^D$ is bicyclic heterocyclyl. In certain embodiments, at least one $R^D$ is tricyclic heterocyclyl.

In certain embodiments, at least one $R^D$ is optionally substituted aryl. In certain embodiments, at least one $R^D$ is aryl. In certain embodiments, at least one $R^D$ is optionally substituted monocyclic aryl. In certain embodiments, at least one $R^D$ is substituted phenyl. In certain embodiments, at least one $R^D$ is unsubstituted phenyl. In certain embodiments, at least one $R^D$ is optionally substituted aryl fused with one or more optionally substituted carbocyclic, heterocyclic, aryl, or heteroaryl groups. In certain embodiments, at least one $R^D$ is optionally substituted bicyclic aryl. In certain embodiments, at least one $R^D$ is optionally substituted naphthyl. In certain embodiments, at least one $R^D$ is an optionally substituted tricyclic aryl ring. In certain embodiments, at least one $R^D$ is optionally substituted anthracenyl.

In certain embodiments, at least one $R^D$ is optionally substituted heteroaryl. In certain embodiments, at least one $R^D$ is optionally substituted monocyclic heteroaryl. In certain embodiments, at least one $R^D$ is optionally substituted 5-membered heteroaryl. In certain embodiments, at least one $R^D$ is optionally substituted pyrrolyl, optionally substituted furanyl, optionally substituted thienyl, optionally substituted imidazolyl, optionally substituted pyrazolyl, optionally substituted oxazolyl, optionally substituted isoxazolyl, optionally substituted thiazolyl, optionally substituted isothiazolyl, optionally substituted triazolyl, optionally substituted furazanyl, optionally substituted oxadiazolyl, optionally substituted thiadiazolyl, or optionally substituted tetrazolyl. In certain embodiments, at least one $R^D$ is optionally substituted 6-membered heteroaryl. In certain embodiments, at least one $R^D$ is substituted pyridyl. In certain embodiments, at least one $R^D$ is unsubstituted pyridyl. In certain embodiments, at least one $R^D$ is optionally substituted heteroaryl fused with one or more optionally substituted carbocyclic, heterocyclic, aryl, or heteroaryl groups. In certain embodiments, at least one $R^D$ is optionally substituted bicyclic heteroaryl. In certain embodiments, at least one $R^D$ is optionally substituted tricyclic heteroaryl. In certain embodiments, at least one $R^D$ is optionally substituted heteroaryl fused with optionally substituted phenyl. In certain embodiments, at least one $R^D$ is optionally substituted indolyl. In certain embodiments, at least one $R^D$ is optionally substituted isoindolyl, optionally substituted indazolyl, optionally substituted benzothienyl, optionally substituted isobenzothienyl, optionally substituted benzofuranyl, optionally substituted benzoisofuranyl, optionally substituted benzimidazolyl, optionally substituted benzoxazolyl, optionally substituted benzisoxazolyl, optionally substituted benzothiazolyl, optionally substituted benzisothiazolyl, optionally substituted benzotriazolyl, optionally substituted benzoxadiazolyl, optionally substituted quinolinyl, optionally substituted isoquinolinyl, optionally substituted cinnolinyl, optionally substituted quinoxalinyl, optionally substituted phthalazinyl, or optionally substituted quinazolinyl.

In certain embodiments, at least one $R^D$ is a nitrogen protecting group when attached to a nitrogen atom. In certain embodiments, at least one $R^D$ is Boc, Fmoc, Cbz, Bz, Bn, Ts, acetyl, p-methoxybenzyl carbonyl, p-methoxyphenyl, or nosyl. In certain embodiments, at least one $R^D$ is an oxygen protecting group when attached to an oxygen atom. In certain embodiments, at least one $R^D$ is silyl when attached to an oxygen atom. In certain embodiments, at least one $R^D$ is TBDPS, TBDMS, TIPS, TES, or TMS, when attached to an oxygen atom. In certain embodiments, at least one $R^D$ is MOM, THP, t-Bu, Bn, allyl, acetyl, pivaloyl, or Bz, when attached to an oxygen atom.

In certain embodiments, at least one $R^D$ is —C(=O)$R^{D1}$. In certain embodiments, at least one $R^D$ is —C(=O)-alkyl. In certain embodiments, at least one $R^D$ is —C(=O)—(C$_{1-6}$ alkyl). In certain embodiments, at least one $R^D$ is —C(=O)Me. In certain embodiments, at least one $R^D$ is —C(=O)Et. In certain embodiments, at least one $R^D$ is —C(=O)Pr. In certain embodiments, at least one $R^D$ is —C(=O)Bu. In certain embodiments, at least one $R^D$ is —C(=O)-heterocyclyl. In certain embodiments, at least one $R^D$ is

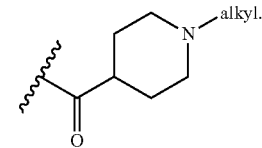

In certain embodiments, at least one $R^D$ is

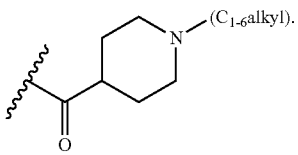

In certain embodiments, at least one $R^D$ is

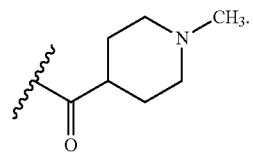 [SMILES: *C(=O)C1CCN(C)CC1]

In certain embodiments, at least one $R^D$ is

In certain embodiments, at least one $R^D$ is —C(=O)-aryl. In certain embodiments, at least one $R^D$ is —C(=O)Ph.

In certain embodiments, two $R^D$ groups are joined to form an optionally substituted heterocyclic ring. In certain embodiments, two $R^D$ groups are joined to form a heterocyclic ring. In certain embodiments, two $R^D$ groups are joined to form an optionally substituted saturated heterocyclic ring. In certain embodiments, two $R^D$ groups are joined to form an optionally substituted unsaturated heterocyclic ring. In certain embodiments, two $R^D$ groups are joined to form an optionally substituted monocyclic heterocyclic ring. In certain embodiments, two $R^D$ groups are joined to form an optionally substituted 3-membered heterocyclic ring. In certain embodiments, two $R^D$ groups are joined to form an optionally substituted 4-membered heterocyclic ring. In certain embodiments, two $R^D$ groups are joined to form an optionally substituted 5-membered heterocyclic ring. In certain embodiments, two $R^D$ groups are joined to form an optionally substituted 6-membered heterocyclic ring. In certain embodiments, two $R^D$ groups are joined to form an optionally substituted 7-membered heterocyclic ring. In certain embodiments, two $R^D$ groups are joined to form an optionally substituted 8-membered heterocyclic ring. In certain embodiments, two $R^D$ groups are joined to form an optionally substituted bicyclic heterocyclic ring. In certain embodiments, two $R^D$ groups are joined to form an optionally substituted tricyclic heterocyclic ring.

Group $R^D$ of Formula (I) has a substituent $R^{D1}$ when $R^D$ is $C(=O)R^{D1}$. In certain embodiments, $R^{D1}$ is optionally substituted alkyl. In certain embodiments, $R^{D1}$ is alkyl. In certain embodiments, $R^{D1}$ is optionally substituted $C_{1-6}$ alkyl. In certain embodiments, $R^{D1}$ is $C_{1-6}$ alkyl. In certain embodiments, $R^{D1}$ is methyl. In certain embodiments, $R^{D1}$ is ethyl. In certain embodiments, $R^{D1}$ is propyl. In certain embodiments, $R^{D1}$ is butyl. In certain embodiments, $R^{D1}$ is optionally substituted alkenyl. In certain embodiments, $R^{D1}$ is alkenyl. In certain embodiments, $R^{D1}$ is optionally substituted $C_{1-6}$ alkenyl. In certain embodiments, $R^{D1}$ is $C_{1-6}$ alkenyl. In certain embodiments, $R^{D1}$ is optionally substituted alkynyl. In certain embodiments, $R^{D1}$ is alkynyl. In certain embodiments, $R^{D1}$ is optionally substituted $C_{1-6}$ alkynyl. In certain embodiments, $R^{D1}$ is $C_{1-6}$ alkynyl.

In certain embodiments, $R^{D1}$ is optionally substituted carbocyclyl. In certain embodiments, $R^{D1}$ is carbocyclyl. In certain embodiments, $R^{D1}$ is saturated carbocyclyl. In certain embodiments, $R^{D1}$ is unsaturated carbocyclyl. In certain embodiments, $R^{D1l}$ is monocyclic carbocyclyl. In certain embodiments, $R^{D1}$ is 3-membered carbocyclyl. In certain embodiments, $R^{D1}$ is cyclopropyl. In certain embodiments, $R^{D1}$ is 4-membered carbocyclyl. In certain embodiments, $R^{D1}$ is cyclobutyl. In certain embodiments, $R^{D1}$ is 5-membered carbocyclyl. In certain embodiments, $R^{D1}$ is cyclopentyl. In certain embodiments, $R^{D1}$ is 6-membered carbocyclyl. In certain embodiments, $R^{D1}$ is cyclohexyl. In certain embodiments, $R^{D1}$ is 7-membered carbocyclyl. In certain embodiments, $R^{D1}$ is cycloheptyl. In certain embodiments, $R^{D1}$ is 8-membered carbocyclyl. In certain embodiments, $R^{D1}$ is cyclooctyl. In certain embodiments, $R^{D1}$ is bicyclic carbocyclyl. In certain embodiments, $R^{D1}$ is tricyclic carbocyclyl.

In certain embodiments, $R^{D1}$ is optionally substituted heterocyclyl. In certain embodiments, $R^{D1}$ is heterocyclyl. In certain embodiments, $R^{D1}$ is saturated heterocyclyl. In certain embodiments, $R^{D1}$ is unsaturated heterocyclyl. In certain embodiments, $R^{D1}$ is monocyclic heterocyclyl. In certain embodiments, $R^{D1}$ is 3-membered heterocyclyl. In certain embodiments, $R^{D1}$ is 4-membered heterocyclyl. In certain embodiments, $R^{D1}$ is 5-membered heterocyclyl. In certain embodiments, $R^{D1}$ is 6-membered heterocyclyl. In certain embodiments, $R^{D1}$ is 7-membered heterocyclyl. In certain embodiments, $R^{D1}$ is 8-membered heterocyclyl. In certain embodiments, $R^{D1}$ is bicyclic heterocyclyl. In certain embodiments, $R^{D1}$ is tricyclic heterocyclyl.

In certain embodiments, $R^{D1}$ is optionally substituted aryl. In certain embodiments, $R^{D1}$ is aryl. In certain embodiments, $R^{D1}$ is optionally substituted monocyclic aryl. In certain embodiments, $R^{D1}$ is substituted phenyl. In certain embodiments, $R^{D1}$ is unsubstituted phenyl. In certain embodiments, $R^{D1}$ is optionally substituted aryl fused with one or more optionally substituted carbocyclic, heterocyclic, aryl, or heteroaryl groups. In certain embodiments, $R^{D1}$ is optionally substituted bicyclic aryl. In certain embodiments, $R^{D1}$ is optionally substituted naphthyl. In certain embodiments, $R^{D1}$ is an optionally substituted tricyclic aryl ring. In certain embodiments, $R^{D1}$ is optionally substituted anthracenyl.

In certain embodiments, $R^{D1}$ is $-N(R^{D1a})_2$. In certain embodiments, $R^{D1}$ is $-N(alkyl)_2$. In certain embodiments, $R^{D1}$ is $-N(C_{1-6}$ alkyl$)_2$. In certain embodiments, $R^{D1}$ is $-N(Me)_2$, $-N(Et)_2$, $-N(Pr)_2$, or $-N(Bu)_2$. In certain embodiments, $R^{D1}$ is $-NH_2$. In certain embodiments, $R^{D1}$ is $-N(nitrogen$ protecting group$)_2$. In certain embodiments, $R^{D1}$ is $-OR^{D1a}$. In certain embodiments, $R^{D1}$ is $-O-(alkyl)$. In certain embodiments, $R^{D1}$ is $-O-(C_{1-6}$ alkyl$)$. In certain embodiments, $R^{D1}$ is $-OMe$, $-OEt$, $-OPr$, or $-OBu$. In certain embodiments, $R^{D1}$ is $-OH$. In certain embodiments, $R^{D1}$ is $-O-$ (oxygen protecting group). In certain embodiments, $R^{D1}$ is $-SR^{D1a}$. In certain embodiments, $R^D$ is $-S$-(alkyl). In certain embodiments, $R^{D1}$ is $-S-(C_{1-6}$ alkyl$)$. In certain embodiments, $R^{D1}$ is $-SMe$, $-SEt$, $-SPr$, or $-SBu$. In certain embodiments, $R^{D1}$ is $-SH$. In certain embodiments, $R^{D1}$ is $-S-$ (sulfur protecting group).

Group $R^{D1}$ of Formula (I) has one or two substituent(s) $R^{D1a}$ when $R^{D1}$ is $-N(R^{D1a})$, $-OR^{D1a}$, or $-SR^{D1a}$. In certain embodiments, at least one $R^{D1a}$ is hydrogen. In certain embodiments, at least one $R^{D1a}$ is optionally substituted alkyl. In certain embodiments, at least one $R^{D1a}$ is alkyl. In certain embodiments, at least one $R^{D1a}$ is optionally substituted $C_{1-6}$ alkyl. In certain embodiments, at least one $R^{D1a}$ is $C_{1-6}$ alkyl. In certain embodiments, at least one $R^{D1a}$ is methyl. In certain embodiments, at least one $R^{D1a}$ is ethyl. In certain embodiments, at least one $R^{D1a}$ is propyl. In certain embodiments, at least one $R^{D1a}$ is butyl. In certain embodiments, at least one $R^{D1a}$ is optionally substituted alkenyl. In certain embodiments, at least one $R^{D1a}$ is alkenyl. In certain embodiments, at least one $R^{D1a}$ is optionally substituted $C_{1-6}$ alkenyl. In certain embodiments, at least one $R^{D1a}$ is $C_{1-6}$ alkenyl. In certain embodiments, at least one $R^{D1a}$ is optionally substituted alkynyl. In certain embodiments, at least one $R^{D1a}$ is alkynyl. In certain embodiments, at least one $R^{D1a}$ is optionally substituted $C_{1-6}$ alkynyl. In certain embodiments, at least one $R^{D1a}$ is $C_{1-6}$ alkynyl.

In certain embodiments, at least one $R^{D1a}$ is optionally substituted carbocyclyl. In certain embodiments, at least one $R^{D1a}$ is carbocyclyl. In certain embodiments, at least one $R^{D1a}$ is saturated carbocyclyl. In certain embodiments, at least one $R^{D1a}$ is unsaturated carbocyclyl. In certain embodiments, at least one $R^{D1a}$ is monocyclic carbocyclyl. In certain embodiments, at least one $R^{D1a}$ is 3-membered carbocyclyl. In certain embodiments, at least one $R^{D1a}$ is cyclopropyl. In certain embodiments, at least one $R^{D1a}$ is 4-membered carbocyclyl. In certain embodiments, at least one $R^{D1a}$ is cyclobutyl. In certain embodiments, at least one $R^{D1a}$ is 5-membered carbocyclyl. In certain embodiments, at least one $R^{D1a}$ is cyclopentyl. In certain embodiments, at least one $R^{D1a}$ is 6-membered carbocyclyl. In certain embodiments, at least one $R^{D1a}$ is cyclohexyl. In certain embodiments, at least one $R^{D1a}$ is 7-membered carbocyclyl. In certain embodiments, at least one $R^{D1a}$ is cycloheptyl. In certain embodiments, at least one $R^{D1a}$ is 8-membered carbocyclyl. In certain embodiments, at least one $R^{D1a}$ is cyclooctyl. In certain embodiments, at least one $R^{D1a}$ is bicyclic carbocyclyl. In certain embodiments, at least one $R^{D1a}$ is tricyclic carbocyclyl.

In certain embodiments, at least one $R^{D1a}$ is optionally substituted heterocyclyl. In certain embodiments, at least one $R^{D1a}$ is heterocyclyl. In certain embodiments, at least one $R^{D1a}$ is saturated heterocyclyl. In certain embodiments, at least one $R^{D1a}$ is unsaturated heterocyclyl. In certain embodiments, at least one $R^{D1a}$ is monocyclic heterocyclyl. In certain embodiments, at least one $R^{D1a}$ is 3-membered heterocyclyl. In certain embodiments, at least one $R^{D1a}$ is 4-membered heterocyclyl. In certain embodiments, at least one $R^{D1a}$ is 5-membered heterocyclyl. In certain embodiments, at least one $R^{D1a}$ is 6-membered heterocyclyl. In certain embodiments, at least one $R^{D1a}$ is 7-membered heterocyclyl. In certain embodiments, at least one $R^{D1a}$ is 8-membered heterocyclyl. In certain embodiments, at least one $R^{D1a}$ is bicyclic heterocyclyl. In certain embodiments, at least one $R^{D1a}$ is tricyclic heterocyclyl.

In certain embodiments, at least one $R^{D1a}$ is optionally substituted aryl. In certain embodiments, at least one $R^{D1a}$ is aryl. In certain embodiments, at least one $R^{D1a}$ is optionally substituted monocyclic aryl. In certain embodiments, at least one $R^{D1a}$ is substituted phenyl. In certain embodiments, at least one $R^{D1a}$ is unsubstituted phenyl. In certain embodiments, at least one $R^{D1a}$ is optionally substituted aryl fused with one or more optionally substituted carbocyclic, heterocyclic, aryl, or heteroaryl groups. In certain embodiments, at least one $R^{D1a}$ is optionally substituted bicyclic aryl. In certain embodiments, at least one $R^{D1a}$ is optionally substituted naphthyl. In certain embodiments, at least one $R^{D1a}$ is an optionally substituted tricyclic aryl ring. In certain embodiments, at least one $R^{D1a}$ is optionally substituted anthracenyl.

In certain embodiments, at least one $R^{D1a}$ is optionally substituted heteroaryl. In certain embodiments, at least one $R^{D1a}$ is optionally substituted monocyclic heteroaryl. In certain embodiments, at least one $R^{D1a}$ is optionally substituted 5-membered heteroaryl. In certain embodiments, at least one $R^{D1a}$ is optionally substituted pyrrolyl, optionally substituted furanyl, optionally substituted thienyl, optionally substituted imidazolyl, optionally substituted pyrazolyl, optionally substituted oxazolyl, optionally substituted isoxazolyl, optionally substituted thiazolyl, optionally substituted isothiazolyl, optionally substituted triazolyl, optionally substituted furazanyl, optionally substituted oxadiazolyl, optionally substituted thiadiazolyl, or optionally substituted tetrazolyl. In certain embodiments, at least one $R^{D1a}$ is optionally substituted 6-membered heteroaryl. In certain embodiments, at least one $R^{D1a}$ is substituted pyridyl. In certain embodiments, at least one $R^{D1a}$ is unsubstituted pyridyl. In certain embodiments, at least one $R^{D1a}$ is optionally substituted heteroaryl fused with one or more optionally substituted carbocyclic, heterocyclic, aryl, or heteroaryl groups. In certain embodiments, at least one $R^{D1a}$ is optionally substituted bicyclic heteroaryl. In certain embodiments, at least one $R^{D1a}$ is optionally substituted tricyclic heteroaryl. In certain embodiments, at least one $R^{D1a}$ is optionally substituted heteroaryl fused with optionally substituted phenyl. In certain embodiments, at least one $R^{D1a}$ is optionally substituted indolyl. In certain embodiments, at least one $R^{D1a}$ is optionally substituted isoindolyl, optionally substituted indazolyl, optionally substituted benzothienyl, optionally substituted isobenzothienyl, optionally substituted benzofuranyl, optionally substituted benzoisofuranyl, optionally substituted benzimidazolyl, optionally substituted benzoxazolyl, optionally substituted benzisoxazolyl, optionally substituted benzothiazolyl, optionally substituted benzisothiazolyl, optionally substituted benzotriazolyl, optionally substituted benzoxadiazolyl, optionally substituted quinolinyl, optionally substituted isoquinolinyl, optionally substituted cinnolinyl, optionally substituted quinoxalinyl, optionally substituted phthalazinyl, or optionally substituted quinazolinyl.

In certain embodiments, at least one $R^{D1a}$ is a nitrogen protecting group when attached to a nitrogen atom. In certain embodiments, at least one $R^{D1a}$ is Boc, Fmoc, Cbz, Bz, Bn, Ts, acetyl, p-methoxybenzyl carbonyl, p-methoxyphenyl, or nosyl. In certain embodiments, at least one $R^{D1a}$ is an oxygen protecting group when attached to an oxygen atom. In certain embodiments, at least one $R^{D1a}$ is silyl when attached to an oxygen atom. In certain embodiments, at least one $R^{D1a}$ is TBDPS, TBDMS, TIPS, TES, or TMS, when attached to an oxygen atom. In certain embodiments, at least one $R^{D1a}$ is MOM, THP, t-Bu, Bn, allyl, acetyl, pivaloyl, or Bz, when attached to an oxygen atom. In certain embodiments, at least one $R^{D1a}$ is a sulfur protecting group when attached to a sulfur atom. In certain embodiments, at least one $R^{D1a}$ is t-Bu, trityl, acetamidomethyl, acetylaminomethyl, acetyl, Bn, Bz, THP, t-butoxycarbonyl, 2,4-dinitrophenyl, 4-pyridylmethyl, carboxymethyl, isobutoxymethyl, or —S(t-Bu), when attached to a sulfur atom.

In certain embodiments, two $R^{D1a}$ groups are joined to form an optionally substituted heterocyclic ring. In certain embodiments, two $R^{D1a}$ groups are joined to form a heterocyclic ring. In certain embodiments, two $R^{D1a}$ groups are joined to form an optionally substituted saturated heterocyclic ring. In certain embodiments, two $R^{D1a}$ groups are joined to form an optionally substituted unsaturated heterocyclic ring. In certain embodiments, two $R^{D1a}$ groups are joined to form an optionally substituted monocyclic heterocyclic ring. In certain embodiments, two $R^{D1a}$ groups are joined to form an optionally substituted 3-membered heterocyclic ring. In certain embodiments, two $R^{D1a}$ groups are joined to form an optionally substituted 4-membered heterocyclic ring. In certain embodiments, two $R^{D1a}$ groups are joined to form an optionally substituted 5-membered heterocyclic ring. In certain embodiments, two $R^{D1a}$ groups are joined to form an optionally substituted 6-membered heterocyclic ring. In certain embodiments, two $R^{D1a}$ groups are joined to form an optionally substituted 7-membered heterocyclic ring. In certain embodiments, two $R^{D1a}$ groups are joined to form an optionally substituted 8-membered heterocyclic ring. In certain embodiments, two $R^{D1a}$ groups are joined to form an optionally substituted bicyclic heterocyclic ring. In certain embodiments, two $R^{D1a}$ groups are joined to form an optionally substituted tricyclic heterocyclic ring.

Ring A of Formula (I) may be substituted with one or more $R^A$ group(s). $R^A$ may be a group as described herein. In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted acyl. In certain embodiments, at least one $R^A$ is unsubstituted acyl. In certain embodiments, at least one $R^A$ is acetyl. In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl. In certain embodiments, at least one $R^A$ is ethyl. In certain embodiments, at least one $R^A$ is propyl. In certain embodiments, at least one $R^A$ is butyl. In certain embodiments, at least one $R^A$ is substituted alkenyl. In certain embodiments, at least one $R^A$ is unsubstituted alkenyl. In certain embodiments, at least one $R^A$ is substituted alkynyl. In certain embodiments, at least one $R^A$ is unsubstituted alkynyl. In certain embodiments, at least one $R^A$ is substituted carbocyclyl. In certain embodiments, at least one $R^A$ is unsubstituted carbocyclyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted heteroaryl. In certain embodiments, at least one $R^A$ is unsubstituted heteroaryl. In certain embodiments, at least one $R^A$ is substituted pyridyl. In certain embodiments, at least one $R^A$ is unsubstituted pyridyl. In certain embodiments, at least one $R^A$ is —$OR^{A1}$. In certain embodiments, at least one $R^A$ is —$N(R^{A1})_2$. In certain embodiments, at least one $R^A$ is —$SR^{A1}$. In certain embodiments, at least one $R^A$ is —OH. In certain embodiments, at least one $R^A$ is —OMe. In certain embodiments, at least one $R^A$ is —$NH_2$. In certain embodiments, at least one $R^A$ is —$NMe_2$. In certain embodiments, at least one $R^A$ is —SH. In certain embodiments, at least one $R^A$ is —SMe.

In certain embodiments, when $R^A$ is —$OR^{A1}$, —$N(R^A)_2$, or —$SR^{A1}$, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is substituted alkenyl. In certain embodiments, at least one $R^{A1}$ is unsubstituted alkenyl. In certain embodiments, at least one $R^{A1}$ is substituted alkynyl. In certain embodiments, at least one $R^{A1}$ is unsubstituted alkynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is an oxygen protecting group when attached to an oxygen atom. In certain embodiments, at least one $R^{A1}$ is a sulfur protecting group when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring.

In certain embodiments, $R^A$ is substituted $C_{1-6}$ alkyl; and j is 1. In certain embodiments, $R^A$ is unsubstituted $C_{1-6}$ alkyl; and j is 1. In certain embodiments, $R^A$ is methyl; and j is 1. In certain embodiments, $R^A$ is ethyl; and j is 1. In certain embodiments, $R^A$ is propyl; and j is 1. In certain embodiments, $R^A$ is butyl; and j is 1.

In certain embodiments, $R^A$ is halogen; and j is 1. In certain embodiments, $R^A$ is F; and j is 1. In certain embodiments, $R^A$ is Cl; and j is 1. In certain embodiments, $R^A$ is Br; and j is 1. In certain embodiments, $R^A$ is I (iodine); and j is 1.

Ring B of Formula (I) may be substituted with one or more $R^B$ group(s). $R^B$ may be a group as described herein. In certain embodiments, at least one $R^B$ is H. In certain embodiments, at least one $R^B$ is halogen. In certain embodiments, at least one $R^B$ is F. In certain embodiments, at least one $R^B$ is Cl. In certain embodiments, at least one $R^B$ is Br. In certain embodiments, at least one $R^B$ is I (iodine). In certain embodiments, at least one $R^B$ is substituted acyl. In certain embodiments, at least one $R^B$ is unsubstituted acyl. In certain embodiments, at least one $R^B$ is acetyl. In certain embodiments, at least one $R^B$ is substituted alkyl. In certain embodiments, at least one $R^B$ is unsubstituted alkyl. In certain embodiments, at least one $R^B$ is $C_{1-6}$ alkyl. In certain embodiments, at least one $R^B$ is methyl. In certain embodiments, at least one $R^B$ is ethyl. In certain embodiments, at least one $R^B$ is propyl. In certain embodiments, at least one $R^B$ is butyl. In certain embodiments, at least one $R^B$ is substituted alkenyl. In certain embodiments, at least one $R^B$ is unsubstituted alkenyl. In certain embodiments, at least one $R^B$ is substituted alkynyl. In certain embodiments, at least one $R^B$ is unsubstituted alkynyl. In certain embodiments, at least one $R^B$ is substituted carbocyclyl. In certain embodiments, at least one $R^B$ is unsubstituted carbocyclyl. In certain embodiments, at least one $R^B$ is substituted heterocyclyl. In certain embodiments, at least one $R^B$ is unsubstituted heterocyclyl. In certain embodiments, at least one $R^B$ is substituted aryl. In certain embodiments, at least one $R^B$ is unsubstituted aryl. In certain embodiments, at least one $R^B$ is substituted phenyl. In certain embodiments, at least one $R^B$ is unsubstituted phenyl. In certain embodiments, at least one $R^B$ is substituted heteroaryl. In certain embodiments, at least one $R^B$ is unsubstituted heteroaryl. In certain embodiments, at least one $R^B$ is substituted pyridyl. In certain embodiments, at least one $R^B$ is unsubstituted pyridyl. In certain embodiments, at least one $R^B$ is —$OR^B$. In certain embodiments, at least one $R^B$ is —$N(R^B)_2$. In certain embodiments, at least one R is —SR. In certain embodiments, at least one $R^B$ is —OH. In certain embodiments, at least one $R^B$ is —OMe. In certain embodiments, at least one $R^B$ is —$NH_2$. In certain embodiments, at least one $R^B$ is —$NMe_2$. In certain embodiments, at least one $R^B$ is —SH. In certain embodiments, at least one $R^B$ is —SMe.

In certain embodiments, when $R^B$ is —$OR^{B1}$, —$N(R^{B1})_2$, or —$SR^{B1}$, at least one $R^{B1}$ is H. In certain embodiments, at least one $R^{B1}$ is substituted acyl. In certain embodiments, at least one $R^{B1}$ is unsubstituted acyl. In certain embodiments, at least one $R^{B1}$ is acetyl. In certain embodiments, at least one $R^{B1}$ is substituted alkyl. In certain embodiments, at least one $R^{B1}$ is unsubstituted alkyl. In certain embodiments, at least one $R^{B1}$ is $C_{1-6}$ alkyl. In certain embodiments, at least one $R^{B1}$ is methyl. In certain embodiments, at least one $R^{B1}$ is ethyl. In certain embodiments, at least one $R^{B1}$ is propyl. In certain embodiments, at least one $R^{B1}$ is butyl. In certain embodiments, at least one $R^{B1}$ is substituted alkenyl. In certain embodiments, at least one $R^{B1}$ is unsubstituted alkenyl. In certain embodiments, at least one $R^{B1}$ is substituted alkynyl. In certain embodiments, at least one $R^{B1}$ is unsubstituted alkynyl. In certain embodiments, at least one $R^{B1}$ is substituted carbocyclyl. In certain embodiments, at least one $R^{B1}$ is unsubstituted carbocyclyl. In certain embodiments, at least one $R^{B1}$ is substituted heterocyclyl. In certain embodiments, at least one $R^{B1}$ is unsubstituted heterocyclyl. In certain embodiments, at least one $R^{B1}$ is substituted aryl. In certain embodiments, at least one $R^{B1}$ is unsubstituted aryl. In certain embodiments, at least one $R^{B1}$ is substituted phenyl. In certain embodiments, at least one $R^{B1}$ is unsubstituted phenyl. In certain embodiments, at least one $R^{B1}$ is substituted heteroaryl. In certain embodiments, at least one $R^{B1}$ is unsubstituted heteroaryl. In certain embodiments, at least one $R^{B1}$ is substituted pyridyl. In certain embodiments, at least one $R^{B1}$ is unsubstituted pyridyl. In certain embodiments, at least one $R^{B1}$ is a nitrogen protecting group when attached to a nitrogen atom. In certain embodiments, at least one $R^{B1}$ is an oxygen protecting group when attached to an oxygen atom. In certain embodiments, at least one $R^{B1}$ is a sulfur protecting group when attached to a sulfur atom. In certain embodiments, two $R^{B1}$ groups are joined to form a substituted heterocyclic ring. In certain embodiments, two $R^{B1}$ groups are joined to form an unsubstituted heterocyclic ring.

In certain embodiments, $R^B$ is substituted $C_{1-6}$ alkyl; and k is 1. In certain embodiments, $R^B$ is unsubstituted $C_{1-6}$ alkyl; and k is 1. In certain embodiments, $R^B$ is methyl; and k is 1. In certain embodiments, $R^B$ is ethyl; and k is 1. In certain embodiments, $R^B$ is propyl; and k is 1. In certain embodiments, $R^B$ is butyl; and k is 1.

In certain embodiments, $R^B$ is halogen; and k is 1. In certain embodiments, $R^B$ is F; and k is 1. In certain embodiments, $R^B$ is Cl; and k is 1. In certain embodiments, $R^B$ is Br; and k is 1. In certain embodiments, $R^B$ is I (iodine); and k is 1.

Ring C of Formula (I) may be substituted with one or more $R^C$ group(s). $R^C$ may be a group as described herein. In certain embodiments, at least one $R^C$ is H. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^C$ is substituted acyl. In certain embodiments, at least one $R^C$ is unsubstituted acyl. In certain embodiments, at least one $R^C$ is acetyl. In certain embodiments, at least one $R^C$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is butyl. In certain embodiments, at least one $R^C$ is substituted alkenyl. In certain embodiments, at least one $R^C$ is unsubstituted alkenyl. In certain embodiments, at least one $R^C$ is substituted alkynyl. In certain embodiments, at least one $R^C$ is unsubstituted alkynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, at least one $R^C$ is substituted pyridyl. In certain embodiments, at least one $R^C$ is unsubstituted pyridyl. In certain embodiments, at least one $R^C$ is —$OR^{C1}$. In certain embodiments, at least one $R^C$ is —$N(R^{C1})_2$. In certain embodiments, at least one $R^C$ is —$SR^{C1}$. In certain embodiments, at least one $R^C$ is —OH. In certain embodiments, at least one $R^C$ is —OMe. In certain embodiments, at least one $R^C$ is —$NH_2$. In certain embodiments, at least one $R^C$ is —$NMe_2$. In certain embodiments, at least one $R^C$ is —SH. In certain embodiments, at least one $R^C$ is —SMe.

In certain embodiments, when $R^C$ is —$OR^{C1}$, —$N(R^{C1})_2$, or —$SR^{C1}$, at least one $R^{C1}$ is H. In certain embodiments, at least one $R^{C1}$ is substituted acyl. In certain embodiments, at least one $R^{C1}$ is unsubstituted acyl. In certain embodiments, at least one $R^{C1}$ is acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is substituted alkenyl. In certain embodiments, at least one $R^{C1}$ is unsubstituted alkenyl. In certain embodiments, at least one $R^{C1}$ is substituted alkynyl. In certain embodiments, at least one $R^{C1}$ is unsubstituted alkynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is an oxygen protecting group when attached to an oxygen atom. In certain embodiments, at least one $R^{C1}$ is a sulfur protecting group when attached to a sulfur atom. In certain embodiments, two $R^{C1}$ groups are joined to form a substituted heterocyclic ring. In certain embodiments, two $R^{C1}$ groups are joined to form an unsubstituted heterocyclic ring.

In certain embodiments, $R^C$ is substituted $C_{1-6}$ alkyl; and m is 1. In certain embodiments, $R^C$ is unsubstituted $C_{1-6}$ alkyl; and m is 1. In certain embodiments, $R^C$ is methyl; and m is 1. In certain embodiments, $R^C$ is ethyl; and m is 1. In certain embodiments, $R^C$ is propyl; and m is 1. In certain embodiments, $R^C$ is butyl; and m is 1.

In certain embodiments, $R^C$ is halogen; and m is 1. In certain embodiments, $R^C$ is F; and m is 1. In certain embodiments, $R^C$ is Cl; and m is 1. In certain embodiments, $R^C$ is Br; and m is 1. In certain embodiments, $R^C$ is I (iodine); and m is 1.

In compounds of Formula (I), j is an integer from 0 to 4, inclusive. In certain embodiments, j is 0. In certain embodiments, j is 1. In certain embodiments, j is 2. In certain embodiments, j is 3. In certain embodiments, j is 4.

In compounds of Formula (I), k is an integer from 0 to 5, inclusive. In certain embodiments, k is 0. In certain embodiments, k is 1. In certain embodiments, k is 2. In certain embodiments, k is 3. In certain embodiments, k is 4. In certain embodiments, k is 5.

In compounds of Formula (I), m is an integer from 0 to 5, inclusive. In certain embodiments, m is 0. In certain embodiments, m is 1. In certain embodiments, m is 2. In certain embodiments, m is 3. In certain embodiments, m is 4. In certain embodiments, m is 5.

In certain embodiments, j and k are each 0. In certain embodiments, j and k are each 1. In certain embodiments, j is 0; and k is 1. In certain embodiments, j is 1; and k is 0. In certain embodiments, j and m are each 0. In certain embodiments, j and m are each 1. In certain embodiments, j is 0; and m is 1. In certain embodiments, j is 1; and m is 0. In certain embodiments, k and m are each 0. In certain embodiments, k and m are each 1. In certain embodiments, k is 0; and m is 1. In certain embodiments, k is 1; and m is 0. In certain embodiments, j, k, and m are each 0. In certain embodiments, j, k, and m are each 1. In certain embodiments, j and k are each 0; and m is 1. In certain embodiments, j and k are each 1; and m is 0. In certain embodiments, j and m are each 0; and k is 1. In certain embodiments, j and m are each 1; and k is 0. In certain embodiments, k and m are each 0; and j is 1. In certain embodiments, k and m are each 1; and j is 0.

In certain embodiments, the compound of Formula (I) is of Formula (II-A-1):

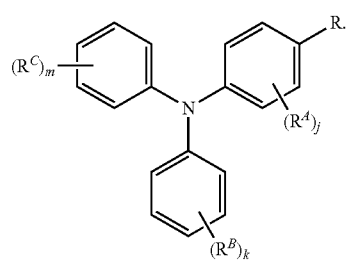

(II-A-1)

In certain embodiments, the compound of Formula (I) is of formula:

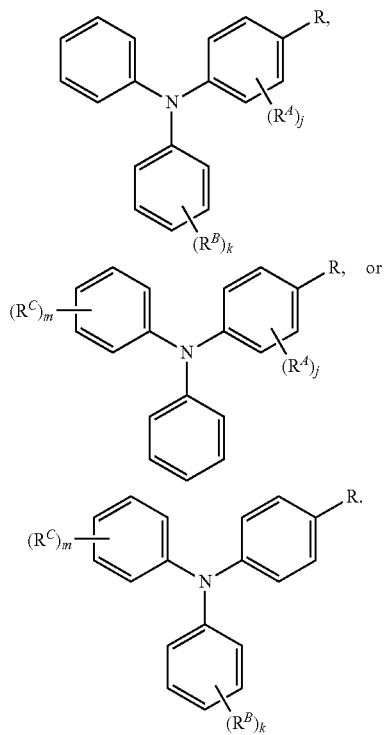

In certain embodiments, the compound of Formula (I) is of formula:

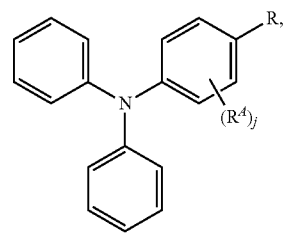

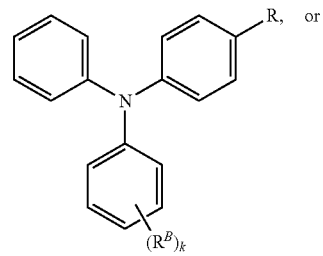

, or

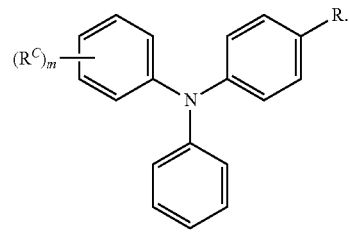

In certain embodiments, the compound of Formula (I) is of Formula (II-A-2):

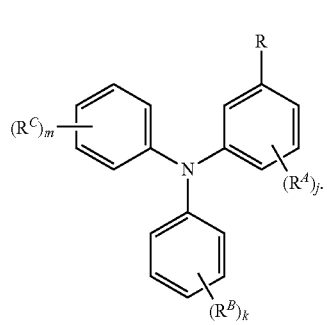

(II-A-2)

In certain embodiments, the compound of Formula (I) is of formula:

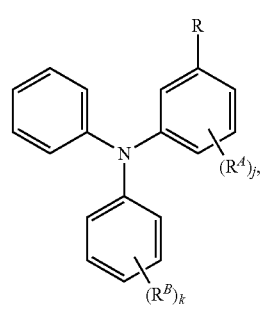

-continued
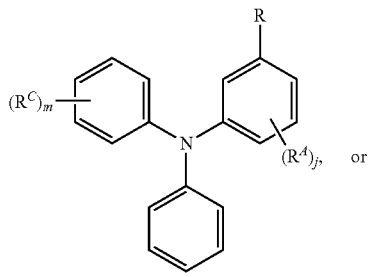
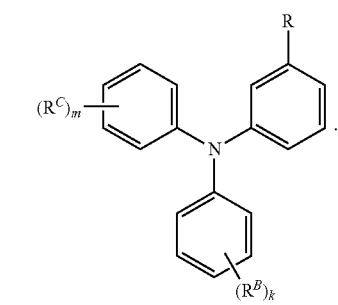
In certain embodiments, the compound of Formula (I) is of formula:
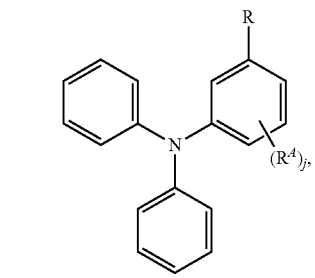
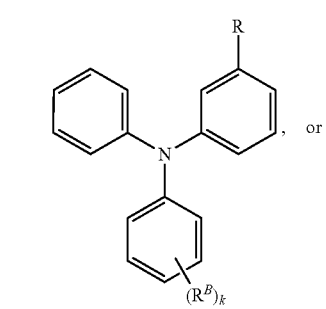
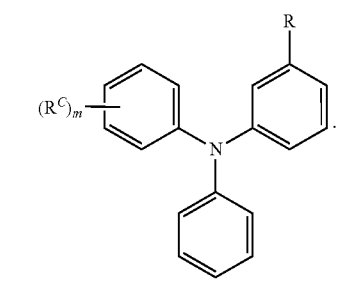
In certain embodiments, the compound of Formula (I) is of Formula (II-A-3):
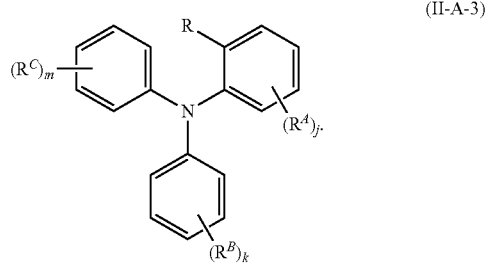
(II-A-3)
In certain embodiments, the compound of Formula (I) is of formula:
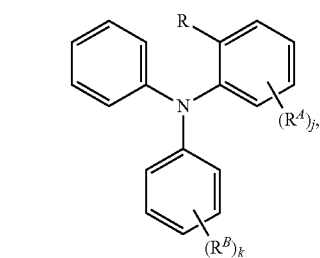
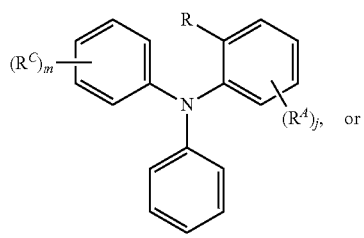
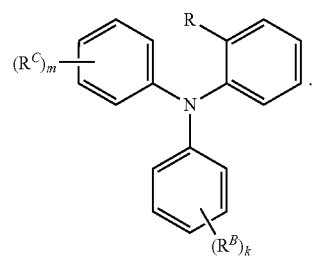
In certain embodiments, the compound of Formula (I) is of formula:
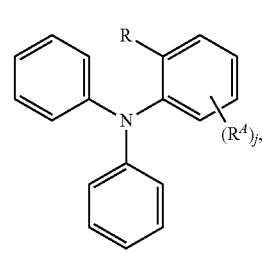

-continued

, or

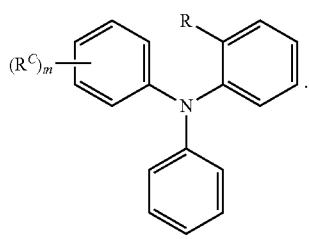

In certain embodiments, the compound of Formula (I) is of Formula (II-B-1):

(II-B-1)

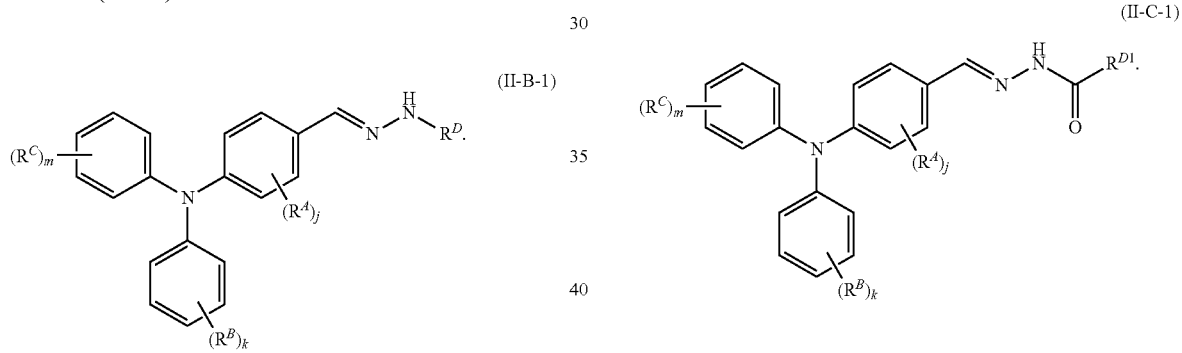

In certain embodiments, the compound of Formula (I) is of Formula (II-B-2):

(II-B-2)

In certain embodiments, the compound of Formula (I) is of Formula (II-B-3):

(II-B-3)

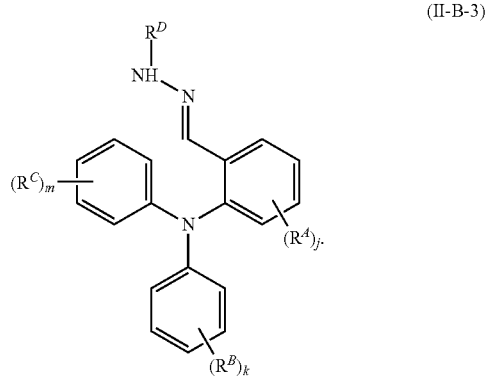

In certain embodiments, the compound of Formula (I) is of Formula (II-C-1):

(II-C-1)

In certain embodiments, the compound of Formula (I) is of Formula (II-C-2):

(II-C-2)

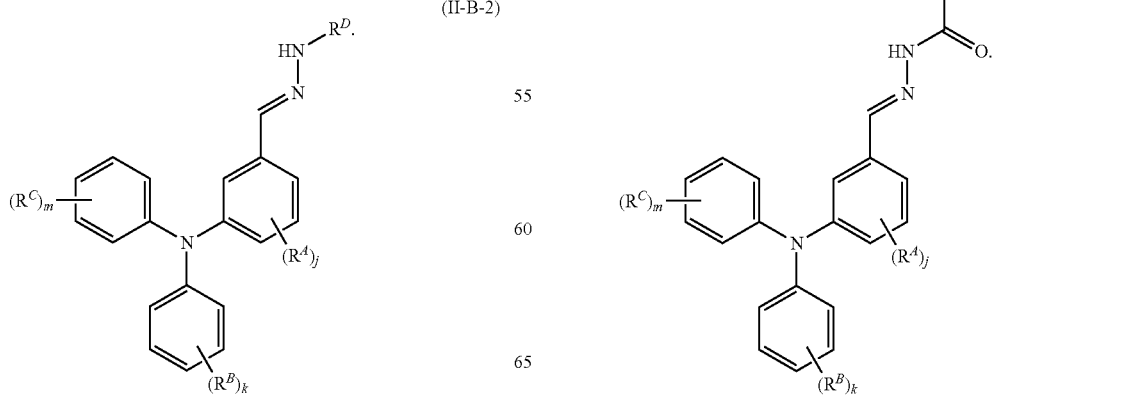

In certain embodiments, the compound of Formula (I) is of Formula (II-C-3):
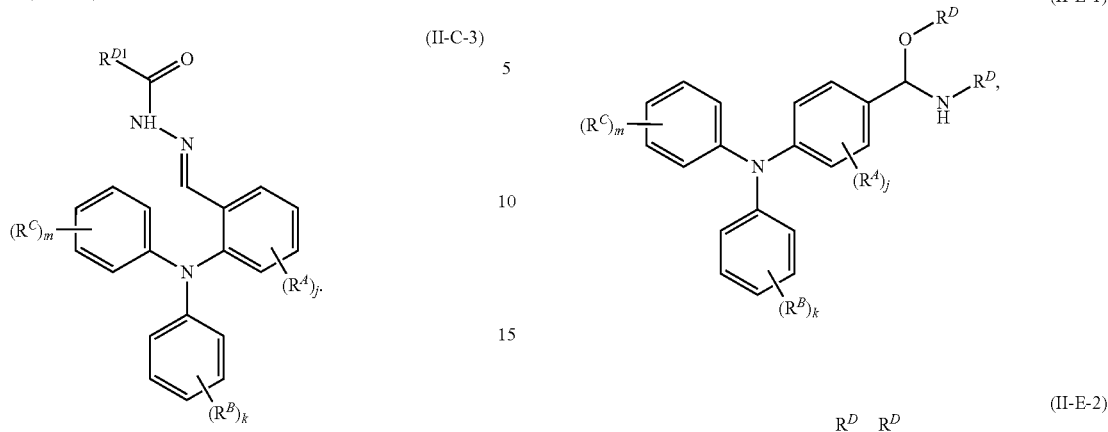
(II-C-3)
In certain embodiments, the compound of Formula (I) is of any one of Formulae (II-D-1)-(II-D-3):
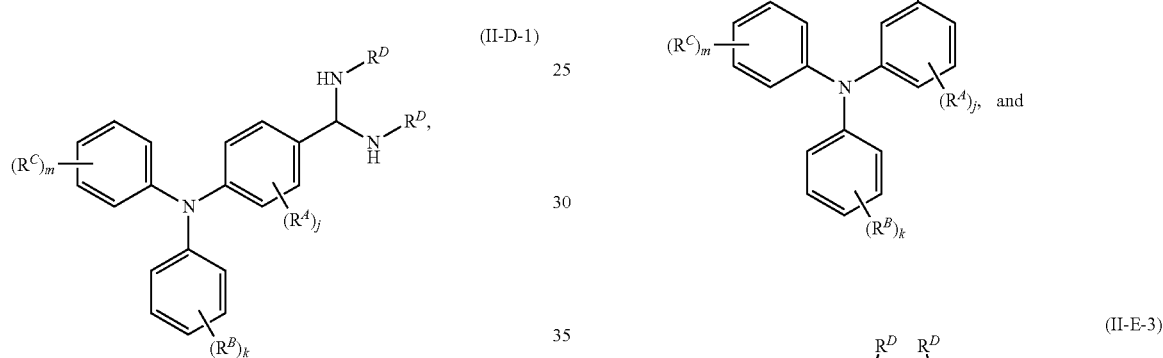
(II-D-1)
(II-D-2)
(II-D-3)
In certain embodiments, the compound of Formula (I) is of any one of Formulae (II-E-1)-(II-E-3):
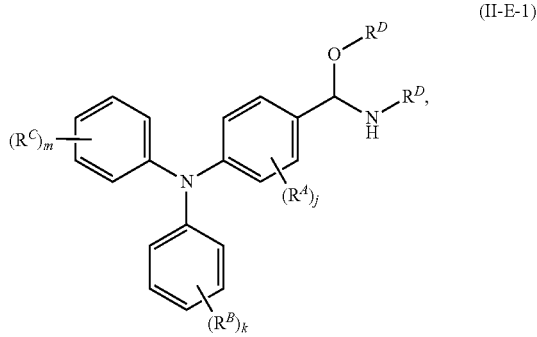
(II-E-1)
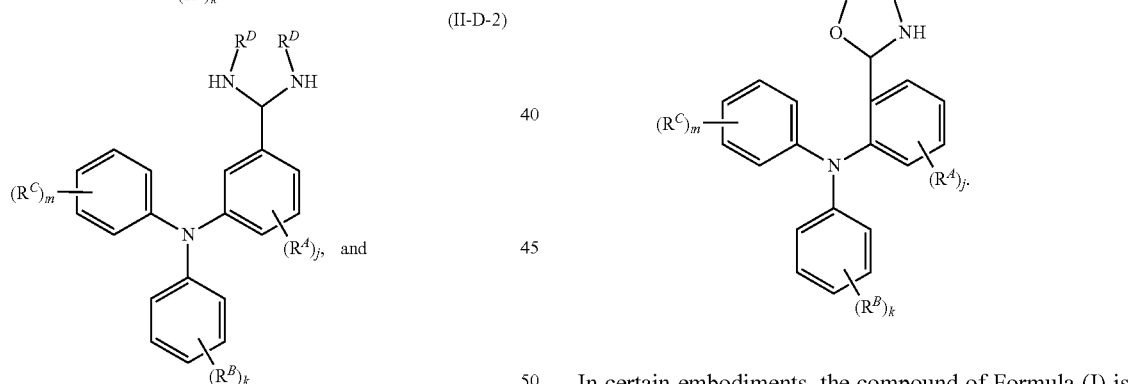
(II-E-2)
(II-E-3)
In certain embodiments, the compound of Formula (I) is of any one of Formulae (II-F-1)-(II-F-3):
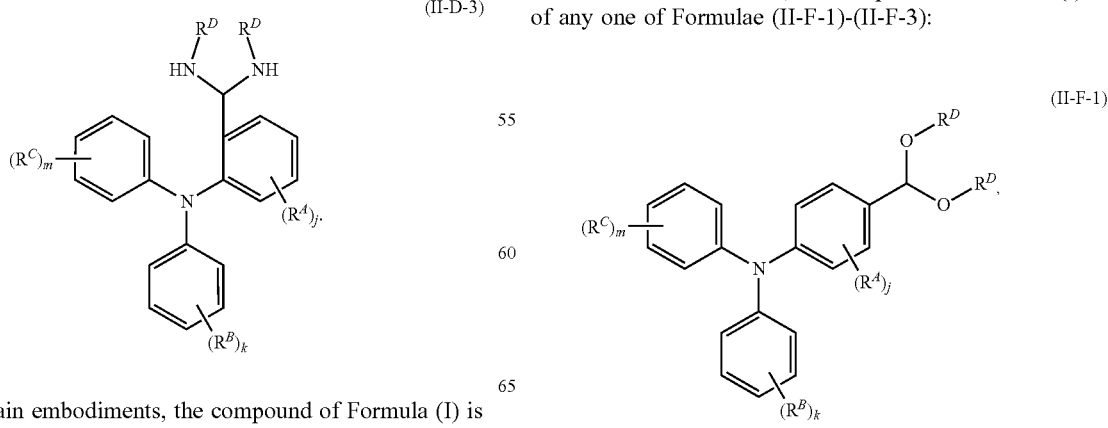
(II-F-1)

(II-F-2)
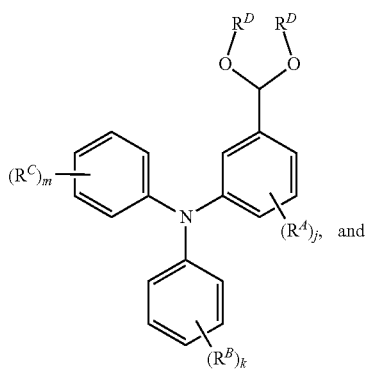
(II-F-3)
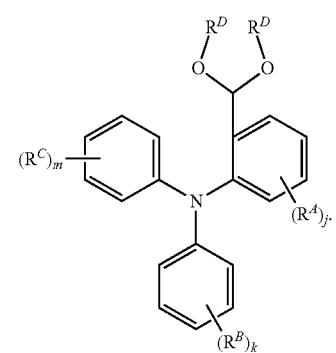
In certain embodiments, the compound of Formula (I) is of any one of Formulae (II-G-1)-(II-G-3):
(II-G-1)
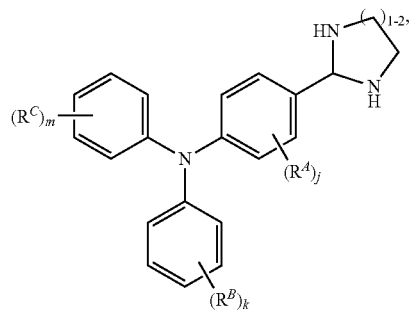
(II-G-2)
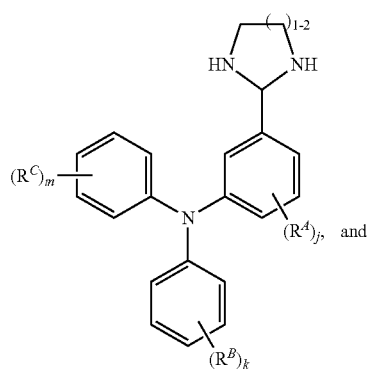
(II-G-3)
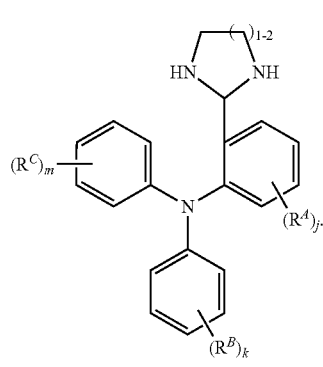
In certain embodiments, the compound of Formula (I) is of any one of Formulae (II-H-1)-(II-H-3):
(II-H-1)
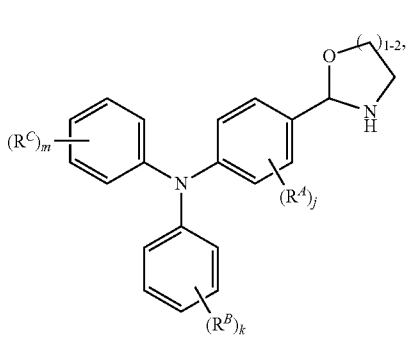
(II-H-2)
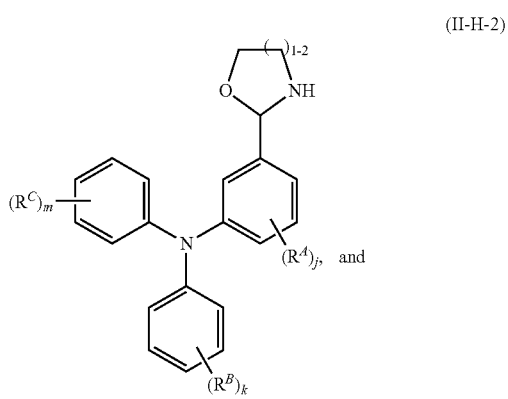
(II-H-3)
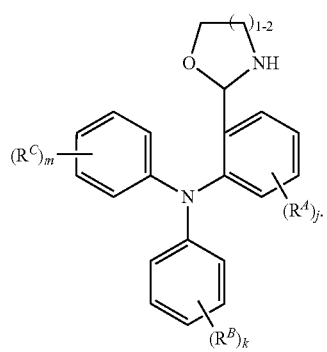
In certain embodiments, the compound of Formula (I) is of any one of Formulae (II-I-1)-(II-I-3):

(II-I-1)
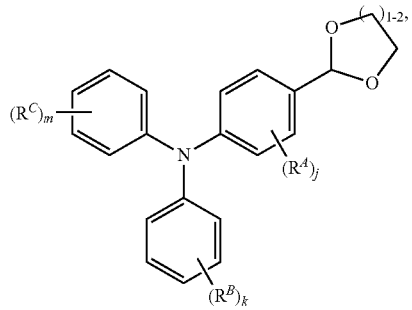
(II-I-2)
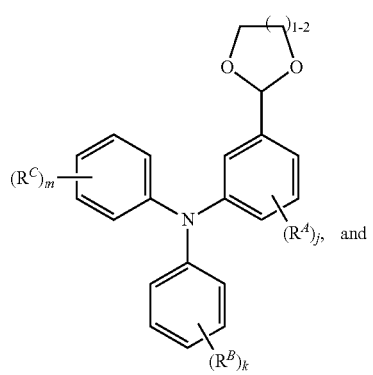
(II-I-3)
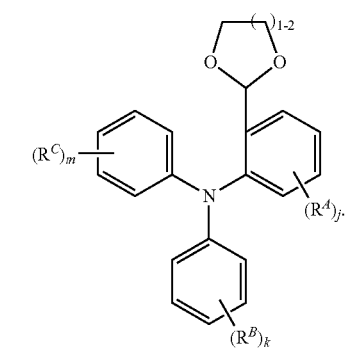
In certain embodiments, the compound of Formula (I) is of any one of Formulae (II-J-1)-(II-J-3):
(II-J-1)
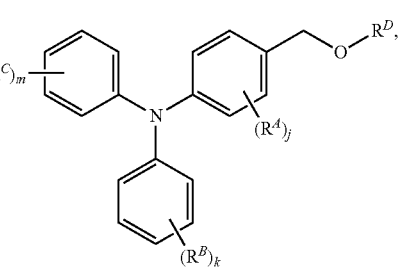
(II-J-2)
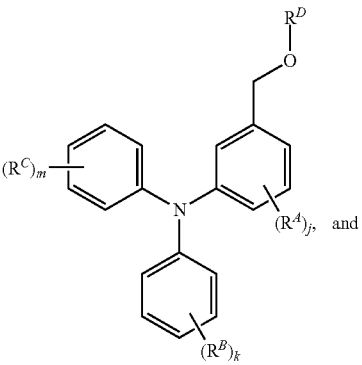
(II-J-3)
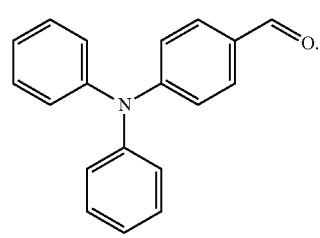
In certain embodiments, the compound of Formula (I) is of the Formula (III-A):
(III-A)
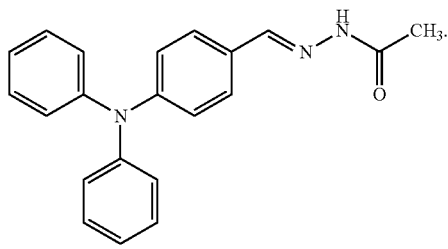
In certain embodiments, the compound of Formula (I) is of the Formula (III-B):
(III-B)
In certain embodiments, the compound of Formula (I) is of the Formula (III-C):

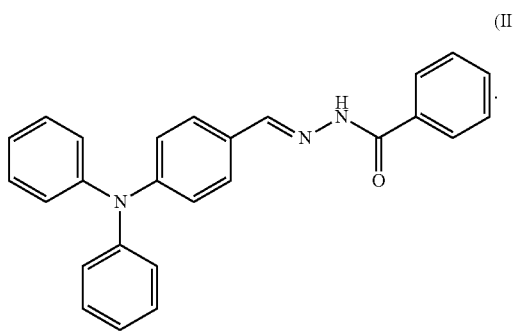
(III-C)

In certain embodiments, the compound of Formula (I) is of the Formula (III-D):

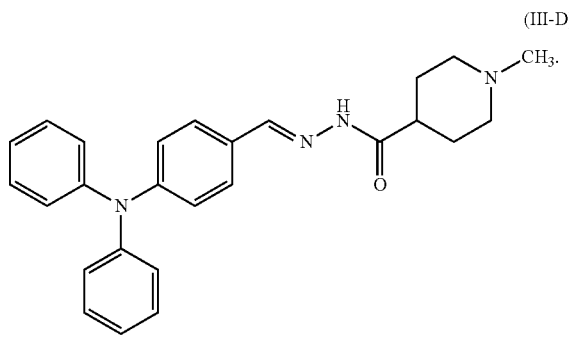
(III-D)

In certain embodiments, the compound of Formula (I) is of the Formula (III-E):

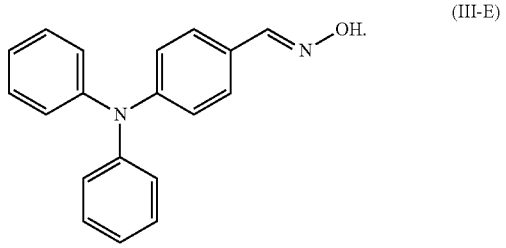 [SMILES: O/N=C/c1ccc(N(c2ccccc2)c2ccccc2)cc1]
(III-E)

In certain embodiments, the compound of Formula (I) is of the Formula (III-F):

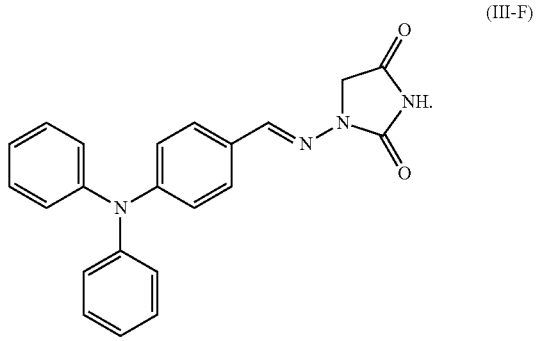 [SMILES: O=C1CN(/N=C/c2ccc(N(c3ccccc3)c3ccccc3)cc2)C(=O)N1]
(III-F)

In certain embodiments, the compound of Formula (I) is of the Formula (III-G):

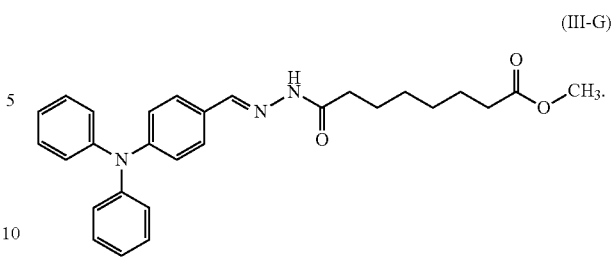
(III-G)

The compounds of the present invention, and pharmaceutically acceptable salts, tautomers, stereoisomers, solvates, hydrates, and polymorphs thereof, may be useful in the treatment of a proliferative disease in a subject.

Pharmaceutical Compositions, Kits, and Administration

The present invention provides pharmaceutical compositions comprising a compound of the invention, and pharmaceutically acceptable salts, tautomers, stereoisomers, solvates, hydrates, and polymorphs thereof, and optionally a pharmaceutically acceptable excipient. In certain embodiments, the compound of the present invention, or a pharmaceutically acceptable salt thereof, is provided in a therapeutically effective amount in the pharmaceutical composition. In certain embodiments, the pharmaceutical compositions of the invention are for use in treating a proliferative disease (e.g., cancer, benign neoplasm, angiogenesis, inflammatory disease, or autoimmune disease) in a subject.

Pharmaceutical compositions described herein can be prepared by any method known in the art of pharmacology. In general, such preparatory methods include the steps of bringing the compound of the present invention (the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

While it may be possible for the compounds disclosed herein, or pharmaceutically acceptable salts, tautomers, stereoisomers, solvates, hydrates, or polymorphs thereof, to be administered orally as they are, it is also possible to present them as a pharmaceutical formulation or dosage. Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in international PCT Application Publication No. WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and international PCT Application Publication Nos. WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi-liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active and/or inactive agents. The compounds or compositions can be administered in combination with additional therapeutically active agents that improve their bioavailability, potency, and/or efficacy, reduce and/or modify their metabolism, inhibit their excretion, decrease their toxicity, and/or modify their distribution within the body. It will also be appreciated that the therapy employed may achieve a desired effect for the same disorder, and/or it may achieve different effects. The combination is understood as "synergistic" when it shows one or more improved properties described above over the compound or composition described herein administered without the additional agents at the same dose as the combination and over the additional agents administered without the compound or composition described herein at the same dose as the combination. Compounds with different or the same mechanisms of action may be combined to achieve synergistic effects. One of the advantages of using synergistic combinations in the treatment of a disease (e.g., a proliferative disease) is that lower doses of the constituent compounds may be used. As a result, the therapeutic index may be increased, and toxic side effects may be reduced.

The compound or composition can be administered concurrently with, prior to, or subsequent to, one or more additional therapeutically active or inactive agents. In general, each agent will be administered at a dose and/or on a time schedule determined for that agent. In will further be appreciated that the additional therapeutically active or inactive agent utilized in this combination can be administered together in a single composition or administered separately in different compositions. The particular combination to employ in a regimen will take into account compatibility of the inventive compound with the additional therapeutically active or inactive agent and/or the desired therapeutic effect to be achieved. In general, it is expected that additional therapeutically active or inactive agents utilized in combination be utilized at levels that do not exceed the levels at which they are utilized individually. In some embodiments, the levels utilized in combination will be lower than those utilized individually.

Exemplary additional therapeutically active or inactive agents include, but are not limited to, anti-cancer agents, anti-diabetic agents, anti-inflammatory agents, immunosuppressant agents, and a pain-relieving agent Therapeutically active or inactive agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the pharmaceutical compositions of the invention include a proteasome inhibitor. In certain embodiments, the pharmaceutical compositions of the invention include bortezomib. In certain embodiments, the pharmaceutical compositions of the invention include, by way of non-limiting example, disulfiram, epigallocatechin-3-gallate, carfilzomib, ONX 0912, CEP-18770, MLN9708, MG-132, MLN2238, danoprevir, nafamostat mesylate, delanzomib, PR-171, NPI-0052 (salinosporamide A), omuralide, lactacystin, or NEOSH101. In certain embodiments, the pharmaceutical compositions of the invention include an Hsp90 inhibitor. In certain embodiments, the pharmaceutical compositions of the invention include 17-N-allylamino-17-demethoxygeldanamycin (17AAG). In certain embodiments, the pharmaceutical compositions of the invention include, for example, geldanamycin, radicicol, gamitrinib, NVP-AUY922, 17-DMAG, BIIB021, BIIB028, elesclomol, NVP-BEP800, SNX-2112, MPC-3100, AT13387, ganetespib, geldanamycin, KW-2478, PF-04929113, IPI-493, IPI-504, SNX-5422, STA-9090, XL-888, CU-0305, CNF1010, macbecin, CCT018159, CCT129397, or PU-H7.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in another aspect, provided are kits for treating a proliferative disease (e.g., cancer, benign neoplasm, angiogenesis, inflammatory disease, or autoimmune disease) in a subject. In certain embodiments, the kits include a first container comprising a compound of the present invention, or a pharmaceutically acceptable salt, tautomer, stereoisomer, solvate, hydrate, polymorph, or composition thereof; and an instruction for administering the compound, or a pharmaceutically acceptable salt, tautomer, stereoisomer, solvate, hydrate, polymorph, or composition thereof, to the subject to treat the proliferative disease. In certain embodiments, the kits of the present invention include one or more additional approved therapeutic agents for use as a combination therapy. In certain embodiments, the instruction includes a notice in the form prescribed by a governmental agency regulating the manufacture, use, or sale of pharmaceutical products, which notice reflects approval by the agency of manufacture, use, or sale for human administration.

Methods of Treatment and Uses

In one aspect, the present invention provides methods for the treatment of a proliferative disease in a subject.

In certain embodiments, the subject described herein is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent or non-human primate.

In certain embodiments, the proliferative disease described herein is cancer. All types of cancers disclosed herein or known in the art are contemplated as being within the scope of the invention. In certain embodiments, the proliferative disease is breast cancer. In certain embodiments, the proliferative disease is prostate cancer. In certain embodiments, the proliferative disease is lung cancer. In certain embodiments, the proliferative disease is ovarian cancer. In some embodiments, the proliferative disease is a benign neoplasm. All types of benign neoplasms disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

Without wishing to be bound by any particular theory, the inventive methods may be useful for treating a proliferative disease by inhibiting immune suppression and/or inducing apoptosis. In some embodiments, the proliferative disease described herein is associated with immune suppression in a subject. Immune suppression may be caused or mediated by immune suppressor myeloid cells (MDSCs). The compounds of the invention, or pharmaceutically acceptable salts, tautomers, stereoisomers, solvates, hydrates, or polymorph thereof, or pharmaceutical compositions thereof, may inhibit MDSCs in a subject. Treating a subject with a proliferative disease using the inventive methods may enhance anti-cancer immune response by inhibiting or eliminating MDSC-mediated immune suppression in the subject. The inventive methods can also be useful to prevent MDSC-promoted metastasis. Moreover, manipulation of immunosuppressive cells by the methods of the invention may be useful to modulate immune response in transplantation, benign neoplasm, and autoimmunity.

The proliferative disease described herein may also be associated with inhibition of apoptosis in a subject. Apoptosis is the process of programmed cell death. Inhibition of apoptosis may result in uncontrolled cell proliferation and, therefore, may cause proliferative diseases. Augmenting apoptosis may be achieved through a number of pathways. For example, enhancing aggresome formation may increase apoptosis, in which ubiquitinated-protein aggregates are processed through autophagy. Moreover, inhibition of proteasomal degradation may enhance aggresomal (autophagic) protein degradation, thereby preventing accumulation of unfolded/misfolded proteins. Apoptosis may also be promoted by inducing unfolded protein responses (UPRs). The UPR is a cellular stress response, which is activated in response to an accumulation of unfolded or misfolded proteins in the lumen of the endoplasmic reticulum. The UPR initially aims to restore normal function of the cells by halting protein translation and to activate the signaling pathways that lead to increasing the production of molecular chaperones involved in protein folding. If these objectives are not achieved, the UPR will then functions towards inducing apoptosis.

The proliferative disease described herein may also be associated with overexpression, overactivity, or up-regulation of one or more proteins (e.g., epidermal growth factor receptor (EGFR), human epidermal growth factor receptor 2 (HER2), estrogen receptor (ER), X-linked inhibitor of apoptosis protein (XIAP), and heat shock protein 90 (Hsp90)) in a subject. In certain embodiments, the proliferative disease is associated with an overexpression, overactivity, or up-regulation of epidermal growth factor receptor (EGFR). The EGFR is the cell-surface receptor for members of the epidermal growth factor family of extracellular protein ligands. EGFR exists on the cell surface and is activated by binding of its specific ligands, including epidermal growth factor and transforming growth factor α. Upon activation by its growth factor ligands, EGFR may undergo a transition from an inactive monomeric form to an active homodimer. EGFR dimerization stimulates its intrinsic intracellular protein-tyrosine kinase activity, initiates several signal transduction cascades, and leads to DNA synthesis and cell proliferation. EGFR overexpression, overactivity, or up-regulation has been associated with a number of proliferative diseases, such as cancers (e.g., lung cancer, anal cancer, breast cancer, prostate cancer, ovarian cancer, and brain cancer). The compounds of the invention, or pharmaceutically acceptable salts, tautomers, stereoisomers, solvates, hydrates, or polymorph thereof, or pharmaceutical compositions thereof, may inhibit and/or down-regulate EGFR.

In certain embodiments, the proliferative disease described herein is associated with an overexpression, overactivity, or up-regulation of human epidermal growth factor receptor 2 (HER2). HER2 is a member of the epidermal growth factor receptor family. HER2 may dimerize upon binding to a ligand, resulting in the autophosphorylation of tyrosine residues within the cytoplasmic domain of the receptors and initiating a variety of signaling pathways. The resulting signaling may promote cell proliferation, oppose apoptosis, and cause proliferative diseases, such as cancers (e.g., breast cancer, prostate cancer, lung cancer, ovarian cancer, stomach cancer, and uterine cancer). The compounds of the invention, or pharmaceutically acceptable salts, tautomers, stereoisomers, solvates, hydrates, or polymorph thereof, or pharmaceutical compositions thereof, may inhibit and/or down-regulate HER2.

In some embodiment, the proliferative disease described herein is associated with an overexpression, overactivity, or up-regulation of estrogen receptor (ER). ER is a receptor that is activated by the hormone estrogen (17β-estradiol) and includes two different forms ERα and ERβ. Once activated by estrogen, the ER is able to bind to DNAs and regulate the activity of various genes. An overexpression, overactivity, or up-regulation of ER may disrupt cell cycle, apoptosis, and DNA repair, and, therefore, may cause proliferative diseases (e.g., cancers, including, but not limited to, breast cancer, ovarian cancer, colon cancer, prostate cancer, lung cancer, and endometrial cancer). The pathogenesis is thought to involve the proliferation of mammary cells stimulated by the binding of estrogen to the ER and/or the genotoxic waste produced during estrogen metabolism. The compounds of the invention, or pharmaceutically acceptable salts, tautomers, stereoisomers, solvates, hydrates, or polymorph thereof, or pharmaceutical compositions thereof, may inhibit and/or down-regulate ER, including ERα and ERβ.

In certain embodiment, the proliferative disease described herein is associated with an overexpression, overactivity, or up-regulation of X-linked inhibitor of apoptosis protein (XIAP). XIAP is a member of a family of inhibitors of apoptosis proteins (IAPs). XIAP stops apoptotic cell death induced either by viral infection or by overproduction of caspases, the enzymes primarily responsible for cell death. Deregulation of XIAP can result in proliferative disease (e.g., cancer, inflammatory diseases, and autoimmune diseases). For example, in the development of lung cancer NCI-H460, the overexpression of XIAP not only inhibits caspase, but also stops the activity of cytochrome c. In developing prostate cancer, XIAP is one of four IAPs overexpressed in the prostatic epithelium, indicating that a molecule that inhibits all IAPs may be necessary for an effective treatment. XIAP has also been shown to mediate anti-apoptosis in breast cancer cells. The compounds of the invention, or pharmaceutically acceptable salts, tautomers, stereoisomers, solvates, hydrates, or polymorph thereof, or pharmaceutical compositions thereof, may inhibit and/or down-regulate XIAP. The cytotoxicity induced by the inventive compounds may be mediated through caspase-dependent apoptosis. In another embodiment, the proliferative disease described herein is associated with an overexpression, overactivity, or up-regulation of heat shock protein 90 (Hsp90). Hsp90 is a molecular chaperone. Hsp90 plays a Janus-like role in the cells, where it is essential for the creation, maintenance, and destruction of proteins. Its normal function is critical to maintaining the health of cells, whereas its dysregulation may contribute to proliferative diseases (e.g., cancer). Cancerous cells overexpress a number of proteins, including growth factor receptors and signal transduction proteins. Hsp90 may stabilize various growth factor receptors, signaling molecules, and mutant proteins that are associated with hyperproliferation and thus oncogenesis. Inhibition of Hsp90 may induce apoptosis and, therefore, inhibit tumor growth. The compounds of the invention, or pharmaceutically acceptable salts, tautomers, stereoisomers, solvates, hydrates, or polymorph thereof, or pharmaceutical compositions thereof, may inhibit and/or down-regulate Hsp90.

In another aspect, the present invention provides methods of inhibiting immune suppression in a subject.

Another aspect of the invention relates to methods of inducing apoptosis in a biological sample or a subject.

Yet another aspect of the invention relates to methods of inducing aggresome formation in a biological sample or a subject.

Still another aspect of the invention relates to methods of inducing unfolded protein responses in a biological sample or a subject.

Also provided in the present invention are methods of inhibiting MDSCs and methods of inhibiting and/or down-regulating proteins (e.g., EGFR, HER2, ER (e.g., ERα and ERβ), XIAP, and Hsp90) in a subject.

In another aspect, the present invention provides methods of treating or lessening the severity of a disease or condition associated with a proliferative disease in a subject Another aspect of the invention relates to methods of inhibiting the growth of multidrug resistant cells in a biological sample or a subject.

In certain embodiments, the methods described above include administering to a subject or a biological sample a therapeutically effective amount of a compound of the present invention, or a pharmaceutically acceptable salt, tautomer, stereoisomer, solvate, hydrate, or polymorph thereof, or a pharmaceutical composition thereof. In certain embodiments, the therapeutically effective amount is administered to a subject. In certain embodiments, the therapeutically effective amount is administered to a biological sample. In certain embodiments, the therapeutically effective amount is administered in combination with one or more additional therapeutic agents. The additional therapeutic agent may be a proteasome inhibitor. In certain embodiments, the therapeutic agent is bortezomib. In certain embodiments, the therapeutic agent is disulfiram, epigallocatechin-3-gallate, carfilzomib, ONX 0912, CEP-18770, MLN9708, MG-132, MLN2238, danoprevir, nafamostat mesylate, delanzomib, PR-171, NPI-0052 (salinosporamide A), omuralide, lactacystin, or NEOSH101. The additional therapeutic agent may also be an Hsp90 inhibitor. In certain embodiments, the therapeutic agent is 17AAG. In certain embodiments, the therapeutic agent is geldanamycin, radicicol, gamitrinib, NVP-AUY922, 17-DMAG, BIIB021, BIIB028, elesclomol, NVP-BEP800, SNX-2112, MPC-3100, AT13387, ganetespib, geldanamycin, KW-2478, PF-04929113, IPI-493, IPI-504, SNX-5422, STA-9090, XL-888, CU-0305, CNF1010, macbecin, CCT018159, CCT129397, or PU-H7. The inventive compounds or compositions may synergistically augment cytotoxicity and, therefore, apoptosis, induced by the additional therapeutic agent(s) in the subject. Thus, the combination of the inventive compounds or compositions and the additional therapeutic agent(s) may be useful in treating proliferative diseases resistant to a treatment using the additional therapeutic agent(s) without the inventive compounds or compositions. Such proliferative diseases include, but are not limited to, proliferative diseases (e.g., cancer (e.g., breast cancer)) resistant to bortezomib and/or 17AAG.

Another aspect of the invention relates to methods of screening a library of compounds to identify one or more compounds that are useful in the treatment of a proliferative disease. The methods of screening a library include providing at least two different compounds of the invention, or pharmaceutically acceptable salts, tautomers, stereoisomers, solvates, hydrates, polymorphs, and compositions thereof; and performing at least one assay using the different compounds of the invention, or pharmaceutically acceptable salts, tautomers, stereoisomers, solvates, hydrates, polymorphs, and compositions thereof, to detect one or more characteristics associated with the proliferative disease.

In yet another aspect, the present invention provides compounds of the present invention, and pharmaceutically acceptable salts, tautomers, stereoisomers, solvates, hydrates, polymorphs, and compositions thereof, for use in the treatment of a proliferative disease in a subject.

EXAMPLES

In order that the invention described herein may be more fully understood, the following examples are set forth. It should be understood that these examples are for illustrative purposes only and are not to be construed as limiting this invention in any manner.

Example 1. Synthesis of the Compounds

The compounds provided herein (see FIG. 1 for the chemical structures) can be prepared from readily available starting materials using the following general methods and procedures. Various intermediates useful for preparation of the compounds of the invention can be prepared in accordance with methods described in the art (Upasani et al., *J. Med. Chem.* (1997) 40:73-84; Hogenkamp et al., *J. Med. Chem.* (1997) 40:61-72) and using the appropriate reagents, starting materials, and purification methods known to those skilled in the art. The compounds of the invention can be prepared using these intermediates. For example, a general method for synthesizing the inventive compounds is demonstrated in Scheme 1 below:

Scheme 1. Exemplary synthesis of the compounds.

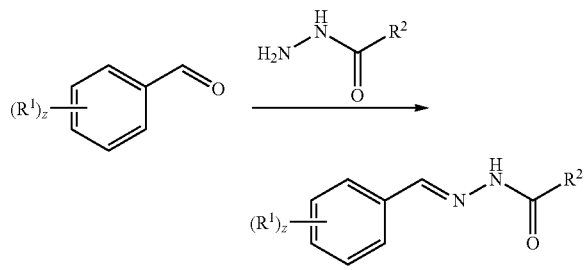

Compound III-B.

273 mg of 4-(diphenylamino)benzaldehyde (Sigma-Aldrich, St. Louis, Mo.) and 74 mg of acetohydrazide were dissolved in 5 mL of methanol followed by addition of one drop trifluoroacetic acid. The reaction mixture was heated at 60° C. overnight resulting in the formation of an orange precipitate, which was isolated by filtration and washed with cold methanol to yield the desired product as an orange semi-crystalline solid (320 mg). m/z (ES$^+$) 330.4 ([M+H]).

Compound III-C.

137 mg of 4-(diphenylamino)benzaldehyde and 272 mg of benzoylhydrazide were dissolved in 5 mL of methanol and heated at 60° C. for 1 hr. After cooling to room temperature, an orange solid precipitated, which was isolated by filtration and washed with cold methanol to yield the desired product as an orange-red crystalline solid. $^1$H NMR indicated the product as a mixture of rotamers. Major rotamer: $^1$H NMR (400 MHz, DMSO-d$_6$) δ 9.77 (s, 1H), 7.95-7.87 (m, 1H), 7.72 (d, J=8.9 Hz, 2H), 7.62-7.47 (m, 1H), 7.41 (dd, J=8.4, 7.4 Hz, 4H), 7.37-7.30 (m, 1H), 7.27-7.14 (m, 6H), 7.15-7.05 (m, 2H), 6.96 (d, J=8.6 Hz, 1H), 6.88 (d, J=8.7 Hz, 2H). m/z (ES$^-$) 390.3 ([M−H]).

Compound III-D.

1.36 g of 4-(diphenylamino)benzaldehyde were dissolved in 100 mL of methanol followed by addition of 785 mg of 1-methylpiperidine-4-carbohydrazide and 2 drops of trifluoroacetic acid. The reaction mixture was refluxed overnight. After removal of the solvent under reduced pressure, diethyl ether was added, and the reaction mixture was sonicated to induce the formation of an off-white powder, which was stirred for additional 2 hr, filtered, and washed with diethyl ether. The powder was dried under high-vacuum to yield the desired product in 55% yield.

Compound III-E.

273 mg of 4-(diphenylamino)benzaldehyde and 60 µL of hydroxylamine (50% in water) were dissolved in 5 mL of methanol and heated at 60° C. for 1 hr. After cooling to room temperature, an orange solid precipitated, which was isolated by filtration and washed with cold methanol to yield the desired product as an orange-red crystalline solid (227 mg). $^1$H NMR (400 MHz, DMSO-d$_6$) δ 11.04 (s, 1H), 8.04

(s, 1H), 7.47 (d, J=8.6 Hz, 2H), 7.31 (dd, J=8.6, 7.2 Hz, 4H), 7.12-7.00 (m, 6H), 6.92 (d, J=8.6 Hz, 2H). m/z (ES⁺) 289.2 ([M+H]).

Compound III-F.

273 mg (1 mmol) of 4-(diphenylamino)benzaldehyde and 157 mg (1.01 mmol) of 1-aminohydantoin hydrochloride were dissolved in 10 mL of methanol, followed by the addition of 20 µL of trifluoroacetic acid. After stirring at 60° C. overnight, the desired product precipitated out from solution without the need of further purification. ¹H NMR (400 MHz, DMSO-d₆) δ 7.72 (s, 1H), 7.56 (d, J=8.4 Hz, 1H), 7.32 (t, J=7.7 Hz, 2H), 7.17-7.02 (m, 3H), 6.95 (d, J=8.3 Hz, 1H), 4.33 (s, 1H). m/z (ES⁻) 369.0 ([M−H]).

Compound III-G.

273 mg (1 mmol) of 4-(diphenylamino)benzaldehyde and 205 mg (1.01 mmol) of methyl 8-hydrazinyl-8-oxooctanoate (prepared according to Vegas et al., *Angew. Chem. Int. Ed.* 2007, 46, 7960-7964.) were dissolved in 5 mL of methanol, followed by the addition of 20 µL of trifluoroacetic acid. After stirring at room temperature, the desired product precipitated out from solution without the need of further purification. m/z (ES⁻) 456.2 ([M−H]).

Compound IV-A.

This compound was synthesized as reported in Bradner et al., *Nat. Chem. Biol.* 2010, 6, 238-243 (illustrated in Scheme 2 below).

Scheme 2. Exemplary synthesis of compound IV-A.

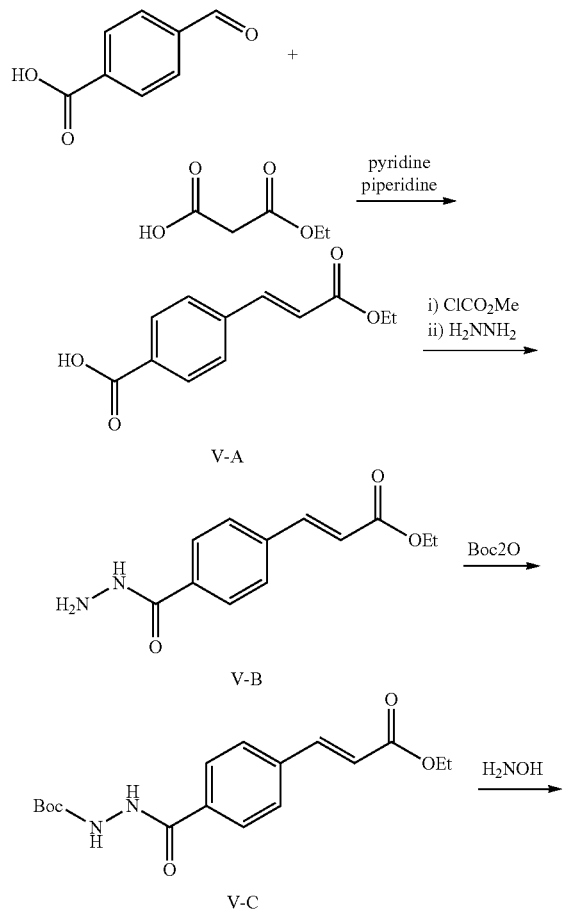

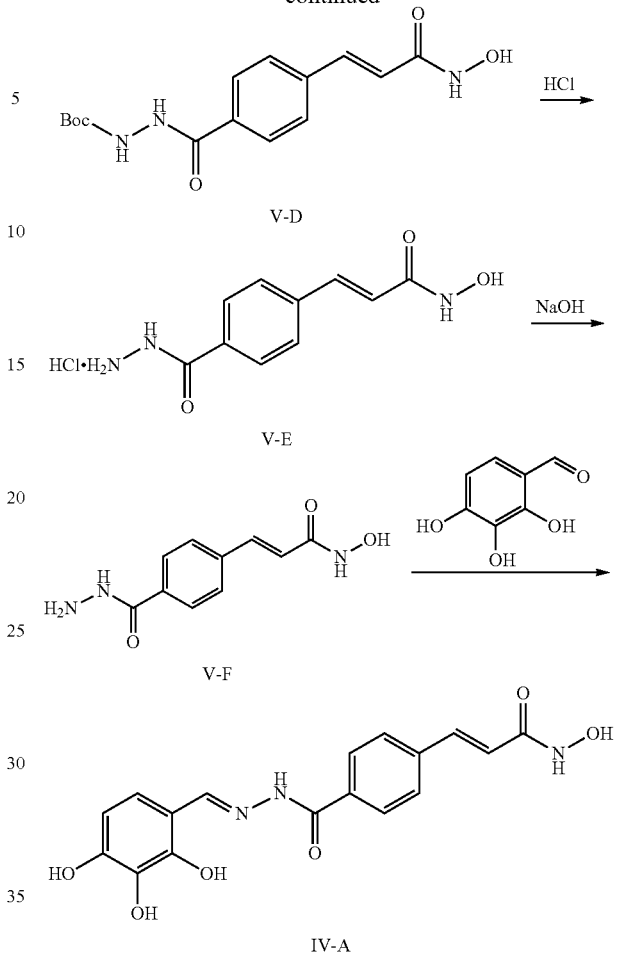

Compound V-A.

To a flask was added 4-formylbenzoic acid (1.5 g, 10 mmol), 3-ethoxy-3-oxopropanoic acid (2.0 g, 15 mmol), piperidine (0.08 mL, 0.81 mmol), and pyridine (4 mL) at room temperature. The reaction mixture was heated to 100° C. for 18 h under a steady flow of nitrogen gas, cooled to room temperature, and poured into 2 M aqueous HCl (100 mL). The resulting mixture was cooled to 0° C. and filtered. The filter cake was washed with acetonitrile (2×10 mL) and dried in vacuo. Cinnamyl ester V-A (1.63 g, 74%) was isolated as a white solid and carried on to hydrazide formation without further purification.

Compound V-B.

To a solution of V-A (0.44 g, 2.0 mmol) in dichloromethane (10 mL) was added triethylamine (0.36 mL, 2.0 mmol) and methyl chloroformate (0.19 mL, 2.0 mmol) at 0° C. The reaction mixture was stirred for 1 h at 0° C. before hydrazine (0.30 mL, 6.0 mmol) was added. The resulting solution was stirred for an additional 2 h at 0° C. Saturated aqueous NaHCO₃ (10 mL) was added to the reaction mixtures, and the resulting biphasic solution was stirred for 30 min at room temperature. The organic layer was separated, dried, and the solvent removed via rotary evaporation. The resulting residue was purified by flash chromatography on silica gel (eluting with EtOAc) to yield compound V-B (0.23 g, 49%) as a white solid.

Compound V-C.

To a solution of hydrazide V-B (6.00 g, 25.6 mmol) in dichloromethane (300 mL) was added Boc anhdyride (5.40 g, 26.2 mmol) and DMAP (12.5 g, 103 mmol). The mixture was stirred at room temperature for 3 h, concentrated, and loaded directly on to silica gel. Flash chromatography, eluting with 1:1 EtOAc/petroleum ether, yielded V-C (5.76 g, 67.3%).

Compound V-D.

To a solution of V-C (5.76 g, 17.2 mmol) in methanol (300 mL) was added a solution of hydroxylamine hydrochloride (11.9 g, 171 mmol) in NaOH/ethanol (1 M, 341 mL). The reaction mixture was stirred for 18 h and concentrated. The residue was dissolved in water to yield a colorless homogenous solution, which was neutralized to pH 7 by the addition of aqueous HCl (1 M). The resulting suspension was extracted with ethyl acetate. The combined organic extracts were dried and concentrated via rotary evaporation. Crude V-D was loaded on to silica gel and purified via flash chromatography, eluting with ethyl acetate, to yield V-D (3.80 g, 68.8%).

Compound V-E.

Boc protected hydrazide V-D (3.50 g, 10.9 mmol) was dissolved in HCl/methanol (6 M, 20 mL) and stirred at ambient temperature for 1 h, while a white precipitate formed. The reaction mixture was filtered to yield the title compound as a white solid (2.38 g, 84.9%).

Compound V-F.

A solution of aqueous NaOH (1 M) was added dropwise to a suspension of V-E (1.8 g, 7.0 mmol) in water (200 mL) until the pH reached 11. The colorless, homogeneous solution was neutralized with dilute aqueous HCl. The resulting precipitate was isolated via filtration and dried in vacuo to yield V-F (1.2 g, 78%) as a gray solid. $^1$H NMR (500 MHz, DMSO-$d_6$) δ 10.85 (s, 1H), 9.84 (s, 1H), 9.12 (s, 1H), 7.85 (d, J=7.8, 2H), 7.63 (d, J=7.8, 2H), 7.49 (d, J=15.8, 1H), 6.55 (d, J=15.8, 1H), 4.72 (s, 2H); $^{13}$C NMR (126 MHz, DMSO-$d_6$) δ 165.92, 163.13, 138.08, 138.03, 134.44, 128.22, 128.07, 121.36. HRMS (ESI$^+$) found: 222.0876 [M+H]; calculated: 222.0873 [M+H].

Compound IV-A.

Compound IV-A was resynthesized and purified to be re-subjected to the biochemical assay to confirm the results from the initial library screen. To a 4 dram vial charged with 2,3,4-trihydroxybenzaldehyde (25.9 mg, 0.168 mmol) was added 420 L of a 200 mM solution of hydrazide V-F (0.084 mmol) in DMSO. The solution was heated on a rotating heating block at 70° C. for 16 h. Reaction progress was monitored via LCMS. Following purification by reverse phase preparatory LCMS (44 mL/min, CH$_3$CN/H$_2$O with 1% formic acid, 5 min gradient), IV-A (7 mg) was isolated as a yellow powder (98% pure, by analytical LCMS). $^1$H NMR (300 MHz, DMSO-$d_6$) δ 12.01 (s, 1H), 11.51 (s, 1H), 10.84 (s, 1H), 9.49 (s, 1H), 9.13 (s, 1H), 8.54 (s, 1H), 8.48 (s, 1H), 7.96 (d, J=8.3, 2H), 7.73 (d, J=8.2, 2H), 7.53 (d, J=16.2, 1H), 6.80 (d, J=8.6, 1H), 6.59 (d, J=15.9, 1H), 6.40 (d, J=8.4, 1H); m/z (ES$^-$) 356 ([M–H]). $^{13}$C NMR (126 MHz, DMSO-$d_6$) δ 163.1, 162.6, 151.0, 149.5, 148.2, 138.8, 138.0, 134.0, 133.4, 128.9, 128.2, 121.9, 121.8, 111.5, 108.4. HRMS (ESI$^+$) found: 358.1033 [M+H]; calculated: 358.1034 [M+H].

Compound IV-B.

212 mg of benzaldehyde and 272 mg of benzoylhydrazide were dissolved in 5 mL of methanol. The desired product precipitated within 10 min. The reaction mixture was stirred for additional 2 hr after which the precipitate was isolated by filtration and washed with methanol to afford the desired product, after removal of solvent under reduced pressure, as white crystals (375 mg). $^1$H NMR (400 MHz, DMSO-$d_6$) δ 11.89 (s, 1H), 8.49 (s, 1H), 8.01-7.90 (m, 2H), 7.74 (dd, J=7.4, 2.0 Hz, 2H), 7.64-7.57 (m, 1H), 7.53 (dd, J=8.2, 6.5 Hz, 2H), 7.50-7.37 (m, 3H). m/z (ES$^-$) 223.3 ([M–H]).

Compound IV-C.

212 mg of benzaldehyde and 148 mg of acetohydrazide were dissolved in 5 mL of methanol followed by addition of one drop of trifluoroacetic acid. The reaction mixture was refluxed overnight followed by the addition of an equal amount of diethyl ether. The solvent was partially removed under reduced pressure to induce precipitation of the desired product, which was isolated as off-white crystals (160 mg). $^1$H NMR indicated the product as a mixture of rotamers. Major rotamer: $^1$H NMR (400 MHz, DMSO-$d_6$) δ 11.25 (s, 1H), 7.98 (s, 1H), 7.72-7.62 (m, 2H), 7.48-7.35 (m, 3H), 2.20 (s, 3H). Minor rotamer: $^1$H NMR (400 MHz, DMSO-$d_6$) δ 11.23 (s, 1H), 11.14 (s, 2H), 8.05 (s, 1H), 7.90 (s, 2H), 7.57-7.48 (m, 8H), 7.33 (ddd, J=8.5, 7.4, 2.4 Hz, 15H), 7.14-7.00 (m, 24H), 6.93 (dd, J=8.8, 2.1 Hz, 7H), 2.15 (s, 3H), 1.92 (s, 3H). m/z (ES$^+$) 163.2 ([M+H]).

Compound IV-D.

149 mg of 4-(dimethylamino)benzaldehyde and 90 mg of acetohydrazide were dissolved in 2 mL of methanol followed by addition of 2 μL of trifluoroacetic acid. The reaction mixture was stirred at room temperature overnight. The desired product precipitated from the reaction mixture, was isolated by filtration, and was washed with cold methanol to yield yellowish crystals (160 mg).

Figure 2A:
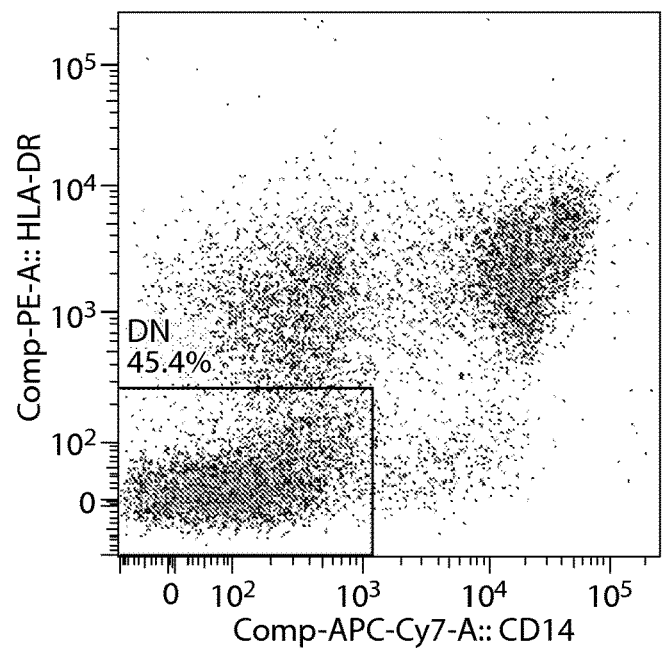
FIG. 2 illustrates that the number of CD11b$^+$CD14$^-$HLA-DR$^{-/low}$CD33$^+$CD15$^+$ myeloid derived suppressor cells (MDSCs) is increased in multiple myeloma (MM)-peripheral blood (FIGS. 2C-2D) or bone marrow (FIGS. 2E-2F), compared to that in healthy peripheral blood (FIGS. 2A-2B).
Figure 2B:
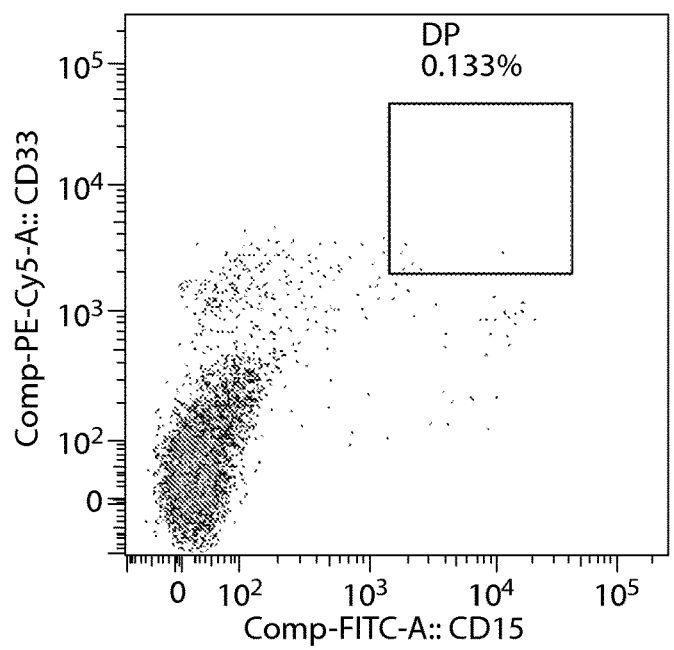
Figure 2C:
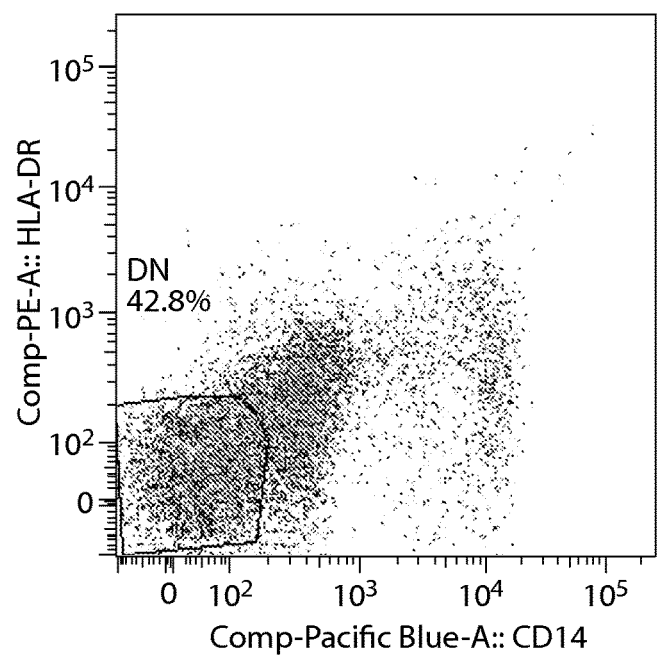
Figure 2D:
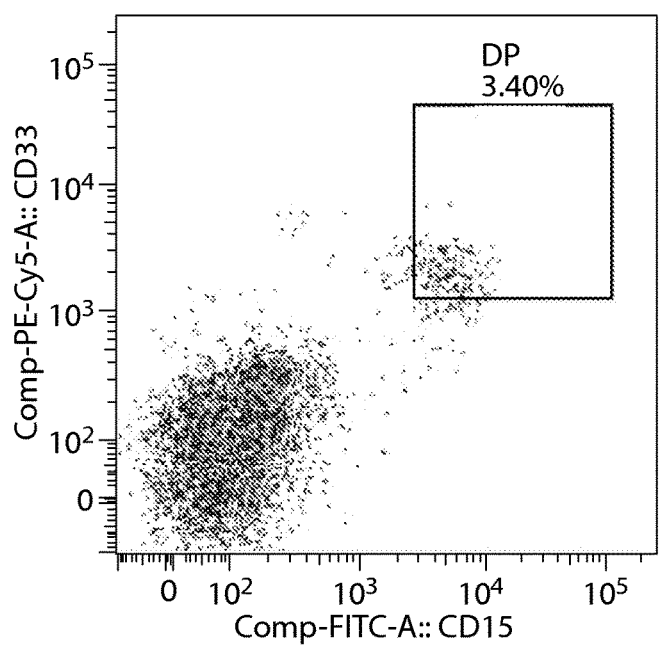
Figure 2E:
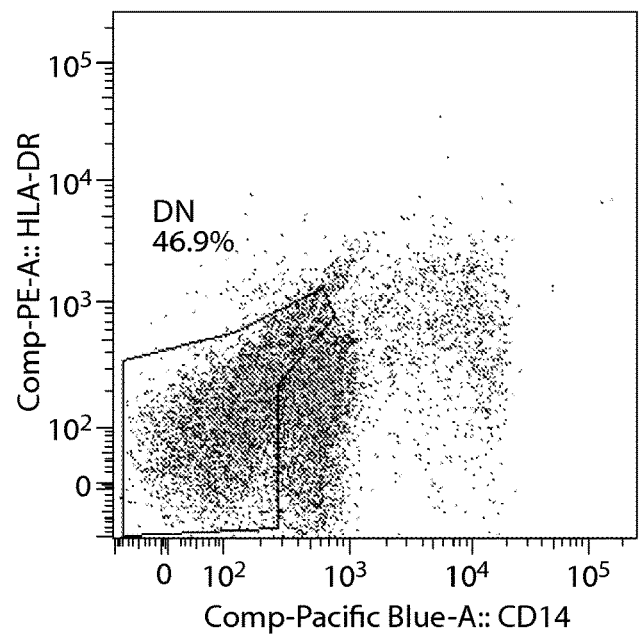
Figure 2F:
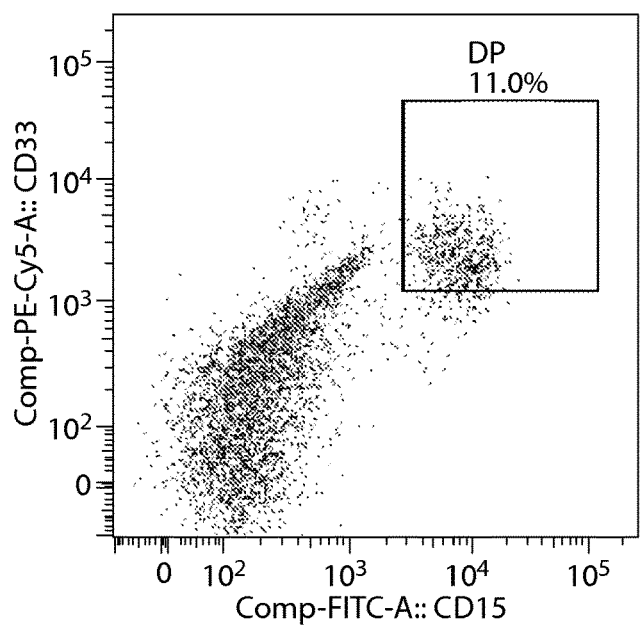

Example 2. MDSCs were Increased in Multiple Myeloma Bone Marrow and Peripheral Blood In order to determine whether myeloid derived suppressor cells (MDSCs) are present in subjects with multiple myeloma (MM), fresh or cultured peripheral blood mononuclear cells (PBMCs) and bone marrow mononuclear cells (BMMCs) from human subjects with MM have been analyzed using standard cell-surface multicolor flow cytometry staining methods (see, e.g., Herzenberg et al., Clin. Chem. (2002) 48:1819-27; and Perez et al., Nat. Biotechnol. (2002) 20:155-62). The number of CD11b$^+$CD14$^+$HLA-DR$^{-/low}$CD33$^+$CD15$^+$ MDSCs was significantly increased in both the peripheral blood (FIGS. 2C-2D) and bone marrow (FIGS. 2E-2F), compared to the number in peripheral blood from healthy subjects (FIGS. 2A-2B).

Figure 3A:
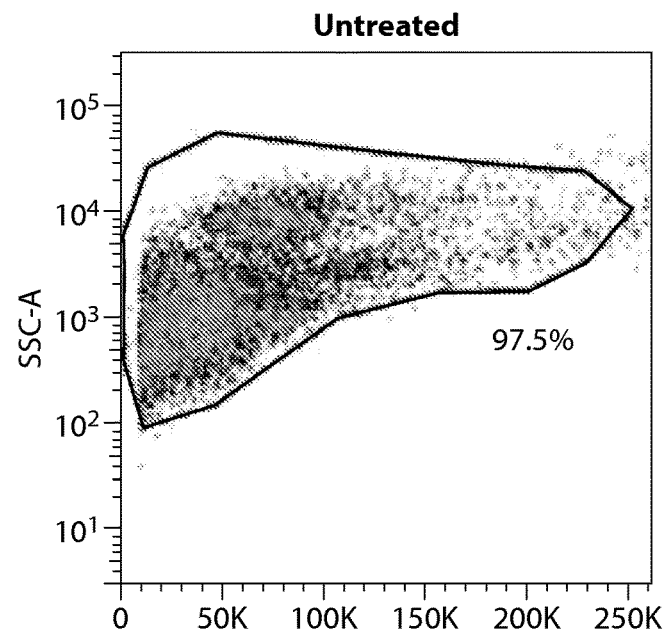
FIG. 3 shows that the number of MDSCs in MM peripheral blood treated with compound III-F is decreased (FIGS. 3E-3H), compared to that in untreated MM peripheral blood (FIGS. 3A-3D).
Figure 3B:
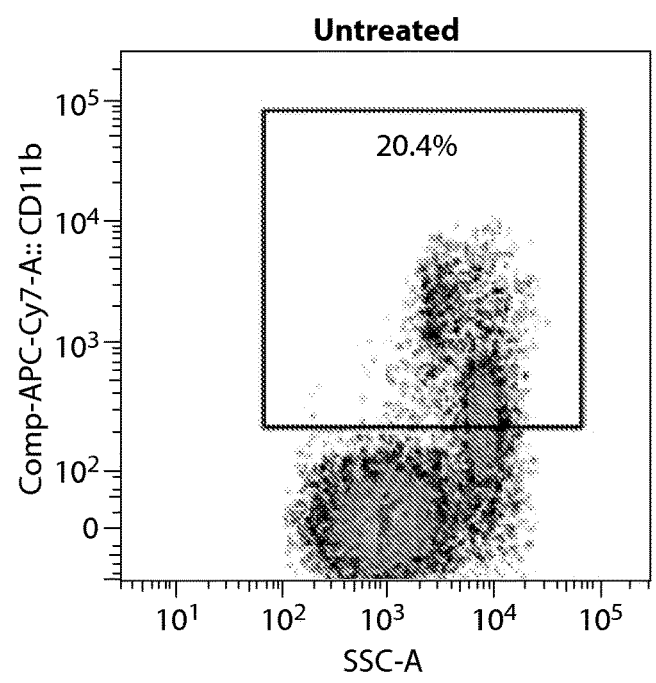
Figure 3C:
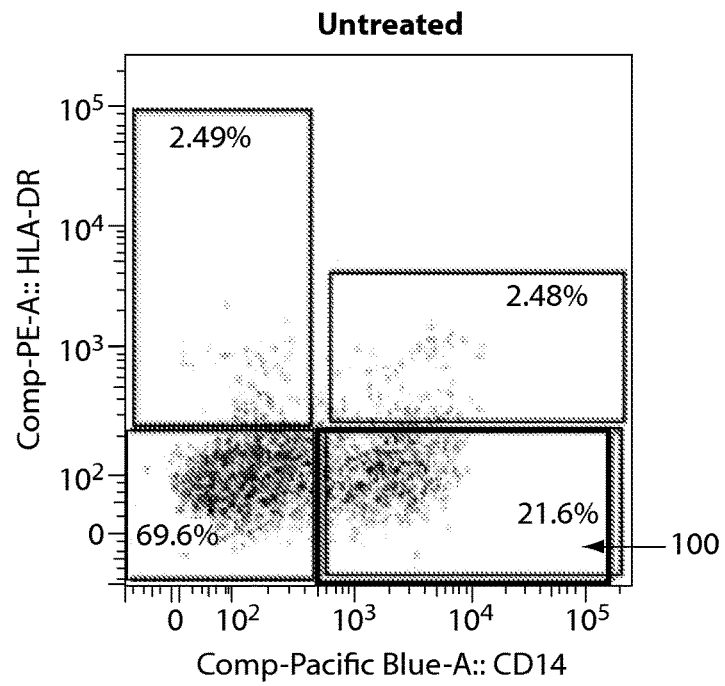
Figure 3D:
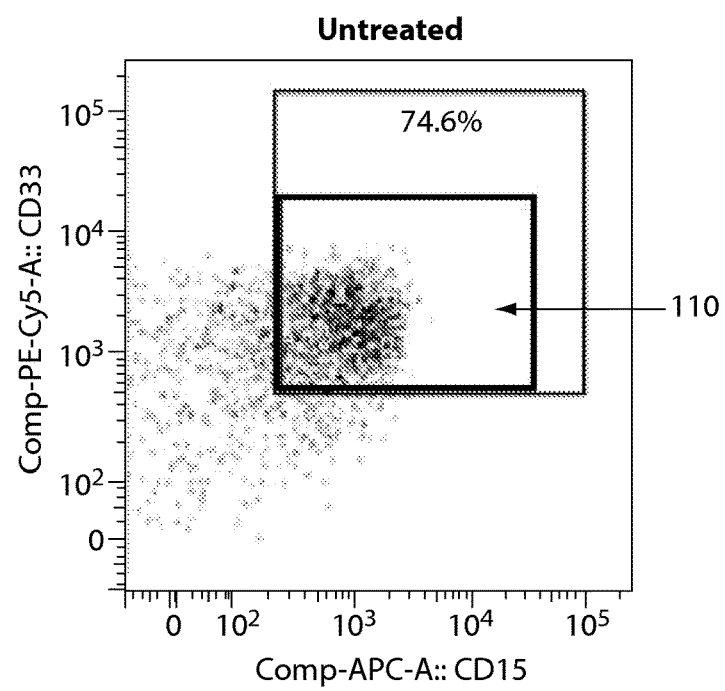
Figure 3E:
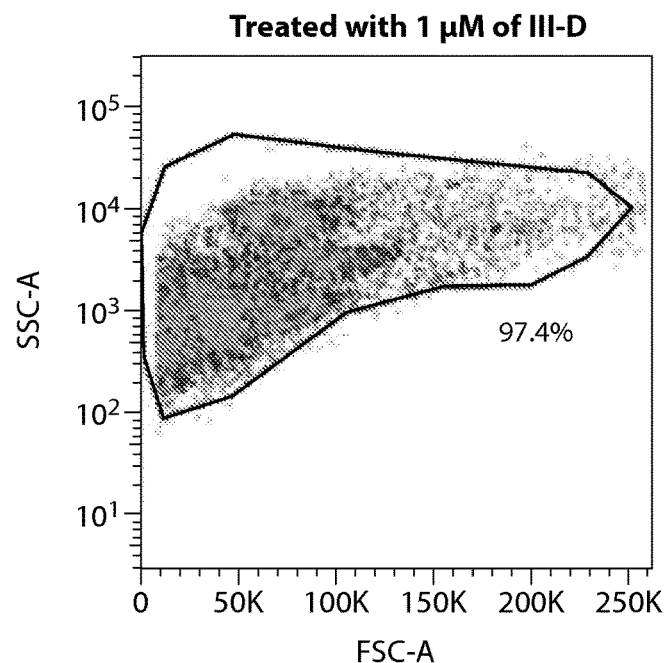
Figure 3F:
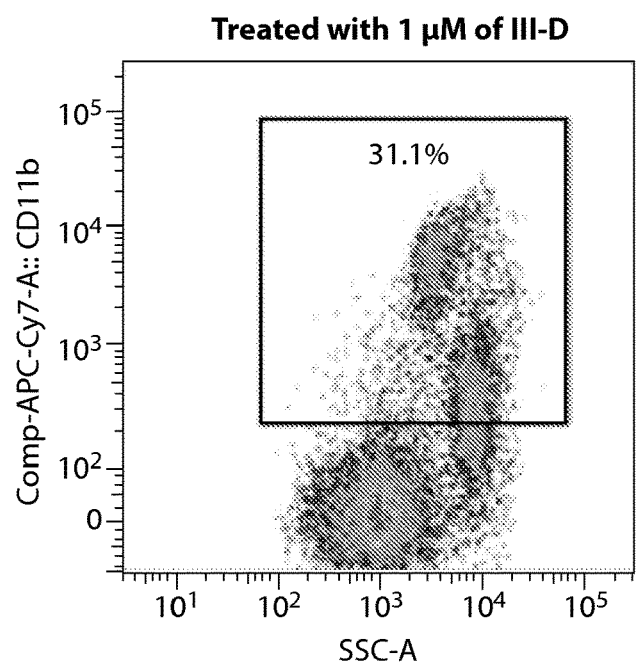

Example 3. Compound III-D Eradicated MDSCs in Multiple Myeloma Bone Marrow and Peripheral Blood Tumor Microenvironment and Regulated MDSC Maturation into CD4$^+$ and/or CD14$^+$HLA-DR$^+$ Antigen Presenting Cells Compound III-D induced significant decrease in the number of CD11b$^+$CD14$^-$ HLA-DR$^{-/low}$CD33$^+$CD15$^+$ MDSCs in MM-PBMC (FIG. 3D), compared to the number of the MDSCs in untreated MM-PBMC (FIG. 3H). MM-PBMCs were cultured overnight with (1 μM) or without compound III-D. MDSCs (CD11b$^+$CD14$^-$HLA-DR$^{-/low}$CD33$^+$CD15$^+$) were determined by flow cytometry analysis. Gates 110 and 130 indicate the MDSC population. Compound III-D induces maturation of MDSCs (CD11b$^+$CD14$^-$HLA-DR$^{-/low}$CD33$^+$CD15$^+$) into CD14$^+$ and/or CD14$^-$HLA-DR$^{-/low}$ (FIG. 3G) in MM peripheral blood compared to untreated MM-PBMC (FIG. 3C). MM-PBMCs were cultured overnight with (1 μM) or without compound III-D. CD14 and/or HLA-DR expressing MDSCs (CD11b$^+$CD14$^-$HLA-DR$^{-/low}$CD33$^+$CD15$^+$) were determined by flow cytometry analysis. Gates 100 and 120 indicate CD14$^+$ mature MDSC population. Gating strategy of MDSCs has been indicated as CD11b$^+$ cells (FIGS. 3A-3B and 3E-3F), CD11b$^+$CD14$^-$HLA-DR$^{-/low}$CD14$^-$ cells (FIGS. 3C and 3G) and MDSCs with a phenotype of CD11b$^+$/HLA-DR$^{-/low}$CD14$^-$/CD33$^+$CD15$^+$ cells (FIGS. 3D and 3H).

Figure 3G:
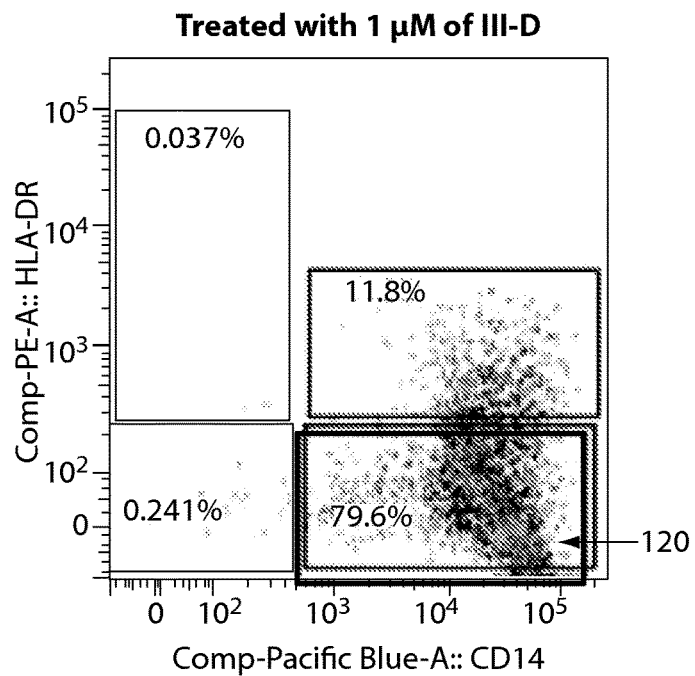
Figure 3H:
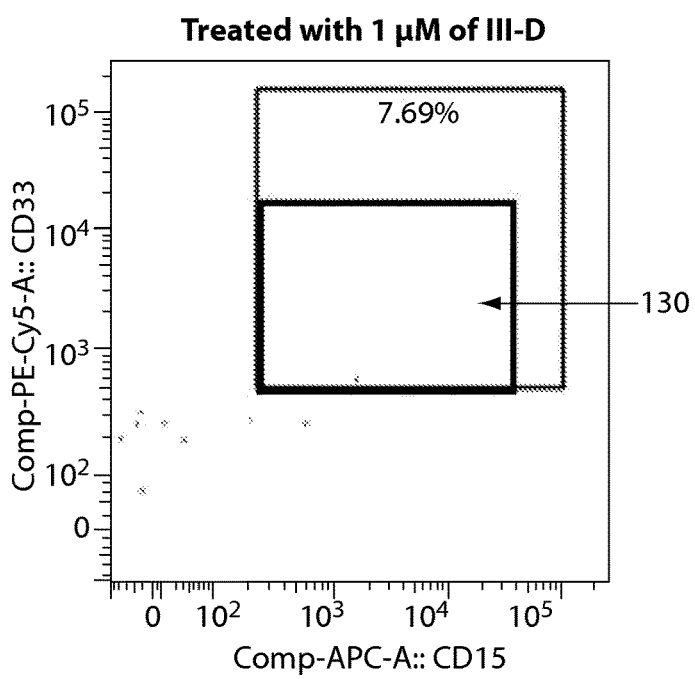

While eliminating immune suppressor MDSCs, compound III-D was found to have induced maturation of those immature MDSCs into CD14$^+$ monocytes and/or CD14$^+$ HLA-DR$^+$ antigen presenting cells (FIG. 3G).

Example 4. Compound III-D Reversed MDSC-Mediated T Cell Suppression

Figure 4:
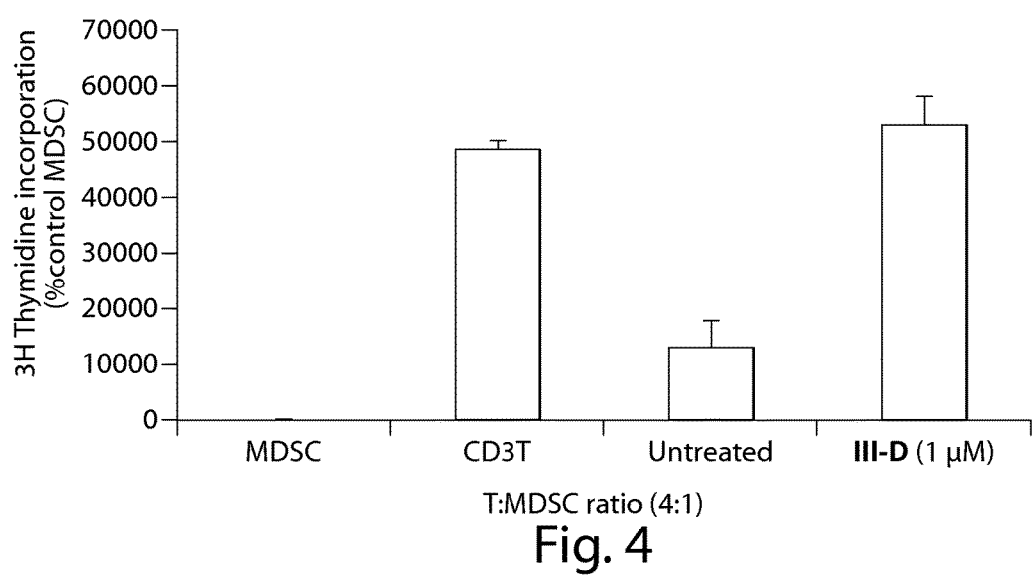
FIG. 4 is a bar graph showing compound III-F reverses MDSC-mediated T cell suppression in MM.
Figure 5A:
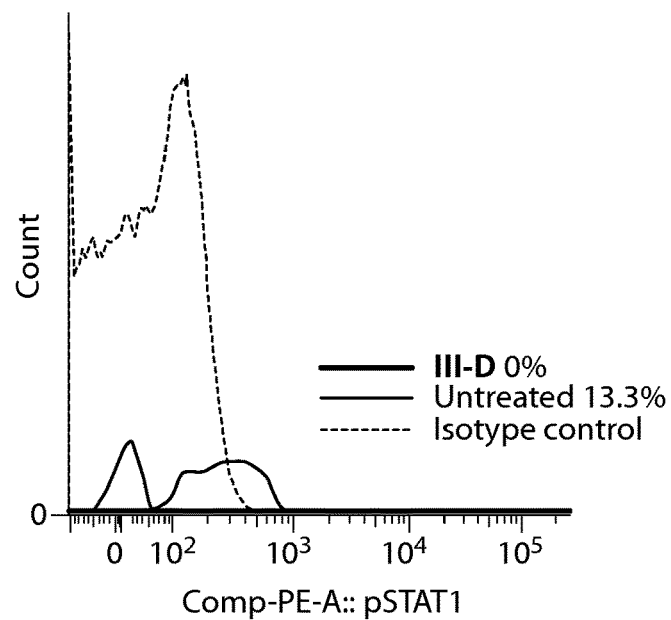
FIG. 5 shows that compound III-F decreases phosphorylations pY701 of STAT1 (FIG. 5B), pY705 of STAT3 (FIG. 5D), and pY694 of STAT5 (FIG. 5F), in MM-PBMC (peripheral blood mononuclear cells) MDSCs. Shown in FIGS. 5A, 5C, and 5E are the corresponding phosphorylations in MM-PBMC MDSCs that are not treated with compound III-F.
Figure 5B:
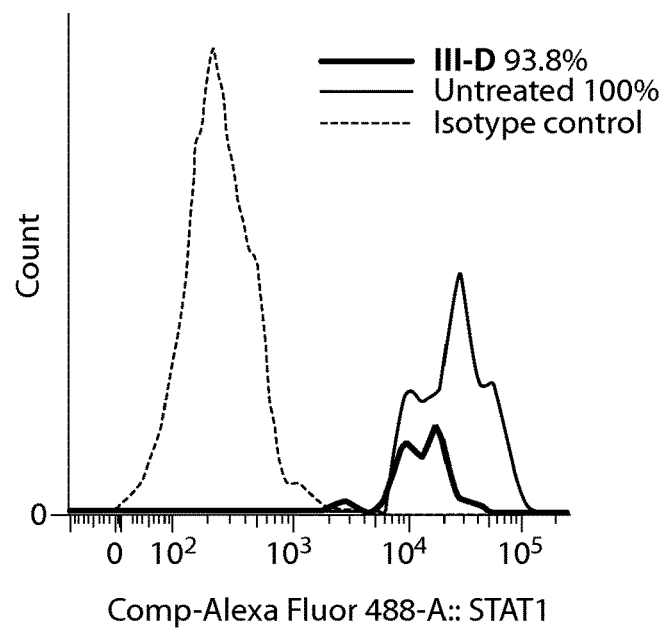
Figure 5C:
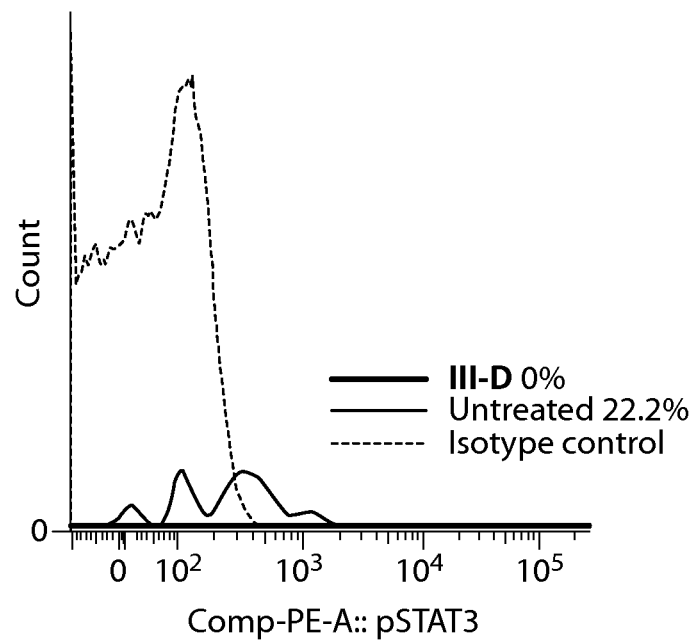
Figure 5D:
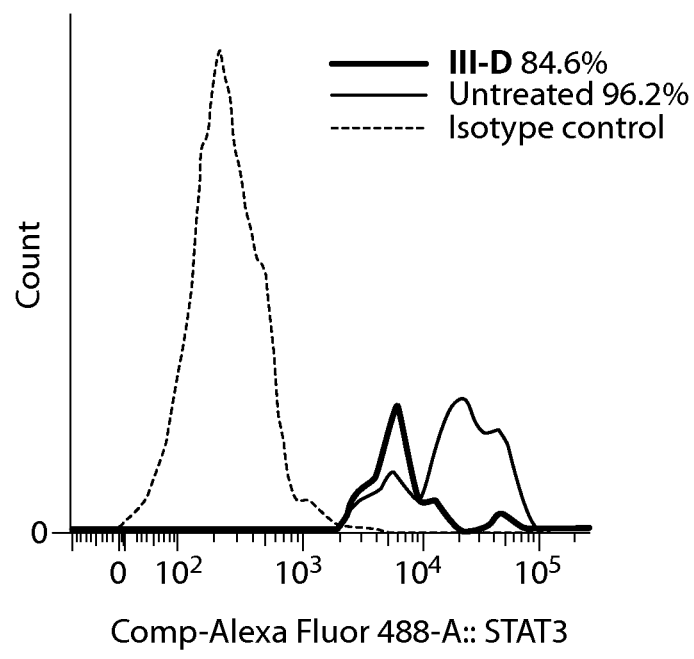
Figure 5E:
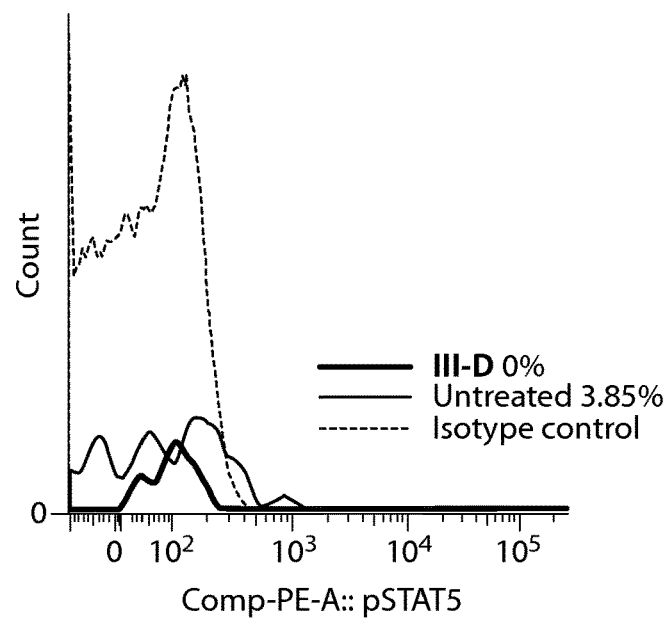
Figure 5F:
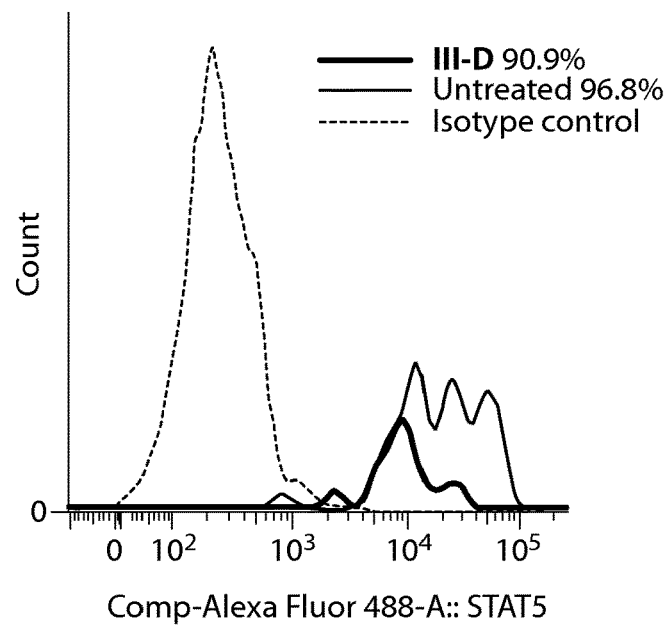

As shown in FIG. 4, CD11b$^+$CD14$^-$HLA-DR$^{-/low}$CD33$^+$CD15$^+$ MDSCs were able to suppress T cell proliferation in the presence of CD3/CD28 and IL-2 stimulation.

CD11b$^+$CD14$^-$HLA-DR$^{-/low}$CD33$^+$ MDSCs and CD3T cells were isolated from peripheral blood of MM patients. The cells were stimulated with antiCD3/CD28 Abs and 2 ng/ml rhIL-2 and cocultured (ratio of T:MDSCs was 4:1) for 5 days in the absence or presence (1 µM) of compound III-D. The cell proliferation was measured by $^3$H-Thymidin incorporation assay.

Example 5. Compound III-D Down-Regulated STAT1, STAT3, and STAT5 Phosphorylation in MDSCs from MM Peripheral Blood STAT-mediated signaling plays an important role in MDSC activation and function. As shown in FIG. 5, Compound III-D significantly reduced the phosphorylation of STAT1, STAT3, and STAT5 in MDSCs determined by standard intracellular flow cytometry staining methods.

MM-PBMCs were cultured overnight with (1 µM) or without compound III-D. Cells were induced with phytohemagglutinin (PHA, 2 ng/ml) for 10 min. Intracellular expression of pY701 STAT1, pY705 STAT3, pY694 STAT5, STAT1, STAT3, and STAT5 in MDSCs (CD11b$^+$CD14$^-$HLA-DR$^{-/low}$CD33$^+$CD15$^+$), was determined by flow cytometry analysis.

Example 6. Compound III-B Inhibits the Growth of MCF7 Cells

Figure 6:
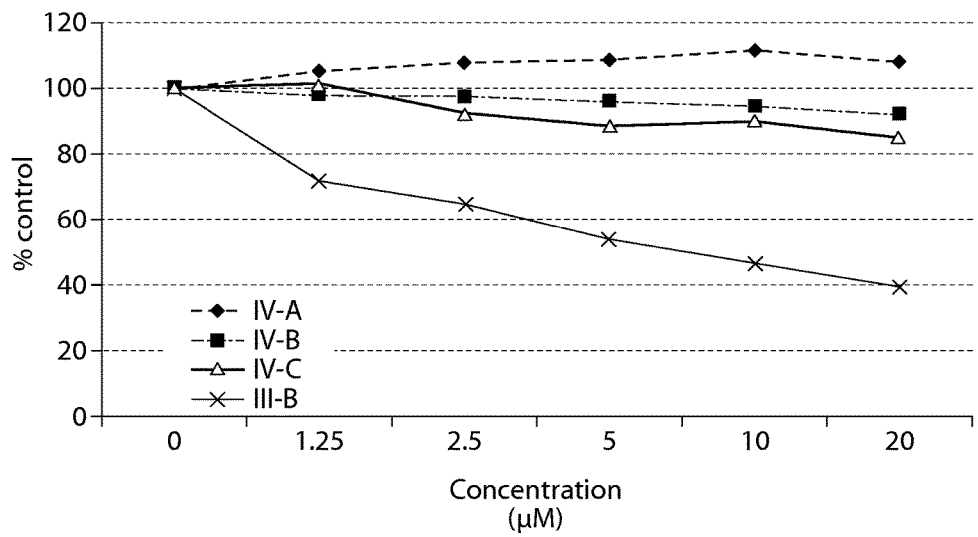
FIG. 6 shows that compound III-B inhibits the growth of MCF7 cells.

MCF7 human breast cancer cell lines were obtained from the American Type Culture Collection (Manassas, Va.). The cells were cultured in DMEM (Mediatech Inc., Manassas, Va.) or RPMI1640 (Mediatech Inc., Manassas, Va.) supplemented with FBS (10%), penicillin, streptomycin, and glutamine (Invitrogen, Auckland, New Zealand). The MCF7 cells were cultured for 72 hr in the presence of compounds IV-A, IV-B, IV-C, and III-B. Cell growth was assessed by measuring 3-(4,5-dimethylthiazol-2-yl)-2,5-diphenyl tetrazolium bromide (MTT) dye absorbance as described in Hideshima et al. ("A proto-oncogene BCL6 is up-regulated in the bone marrow microenvironment in multiple myeloma cells." *Blood* (2010) 115:3772-3775). The MCF7 cells were harvested using 0.05% trypsin-EDTA (Invitrogen) and distributed into 96-well plates (10,000-20,000 cells/well) 24 hr prior to the treatment. All experiments were performed three times in quadruplicate. As shown in FIG. 6, compound III-B inhibits MCF7 cell growth, and compounds IV-A, IV-B, and IV-C do not.

Example 7. Compound III-B Inhibits the Growth of LnCaP Cells

Figure 7:
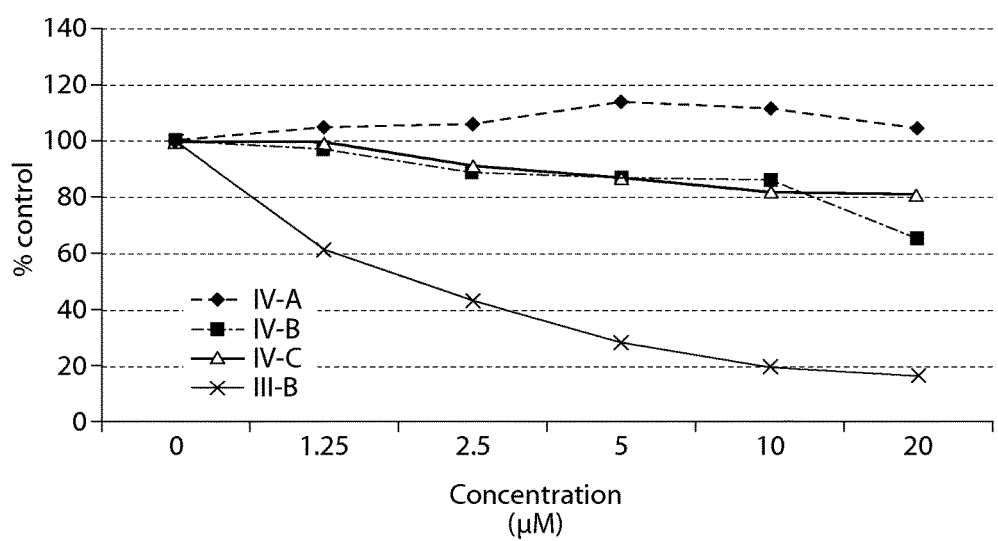
FIG. 7 shows that compound III-B inhibits the growth of LnCaP cells.

LnCaP human prostate cancer cells were obtained, cultured, and assayed in the same manner as in Example 6. As shown in FIG. 7, compound III-B inhibits LnCaP cell growth, and compounds IV-A, IV-B, and IV-C do not.

Figure 8:
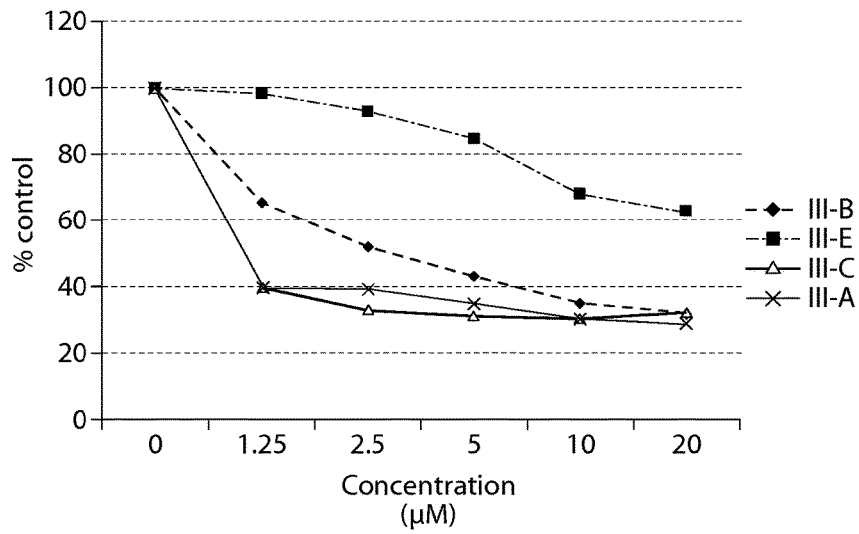
FIG. 8 shows that compounds III-A, III-B, III-C, and III-E inhibit the growth of MCF7 cells.

Example 8. Compounds III-A, III-B, III-C, and III-E Inhibit the Growth of MCF7 Cells MCF7 cells were obtained, cultured (in the presence of compounds III-A, III-B, III-C, or III-E), and assayed in a similar manner as in Example 6. As shown in FIG. 8, all compounds III-A, III-B, III-C, and III-E inhibit MCF7 cell growth.

Figure 9:
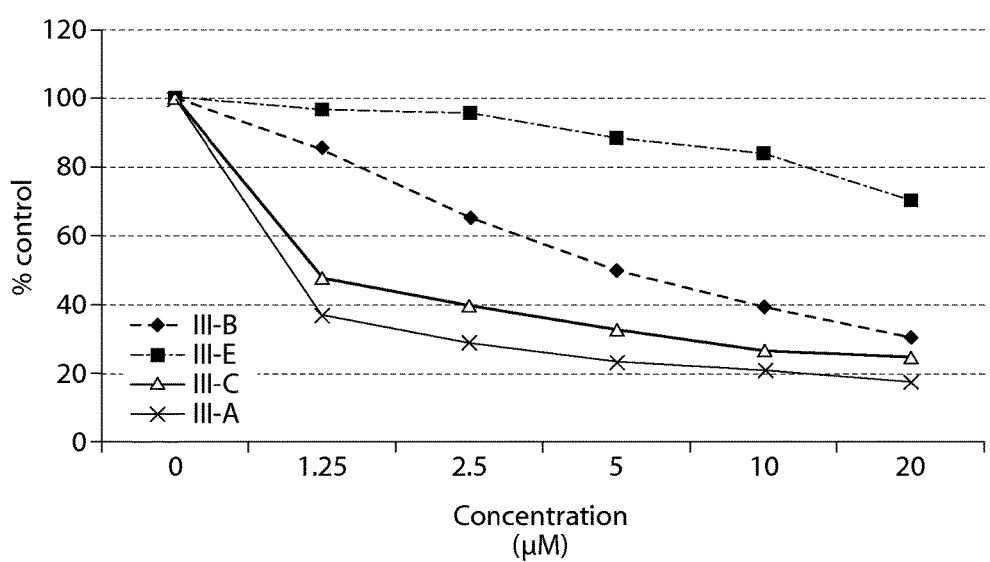
FIG. 9 shows that compounds III-A, III-B, III-C, and III-E inhibit the growth of T47D cells.

Example 9. Compounds III-A, III-B, III-C, and II-E Inhibit the Growth of T47D Cells T47D human breast cancer cells were obtained, cultured (in the presence of compounds III-A, III-B, III-C, or III-E), and assayed in a similar manner as in Example 6. As shown in FIG. 9, all compounds III-A, III-B, III-C, and III-E inhibit T47D cell growth.

Figure 10:
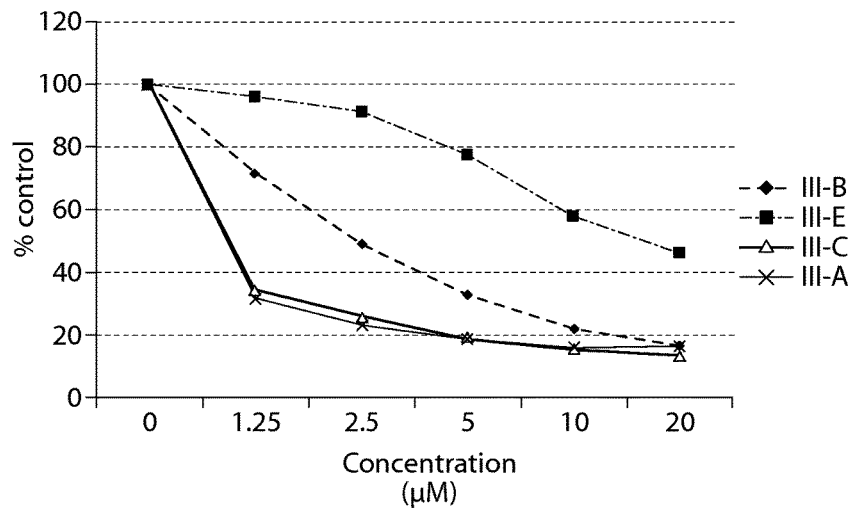
FIG. 10 shows that compounds III-A, III-B, III-C, and III-E inhibit the growth of LnCaP cells.

Example 10. Compounds III-A, III-B, III-C, and II-E Inhibit the Growth of LnCaP Cells LnCaP cells were obtained, cultured (in the presence of compounds III-A, III-B, III-C, or III-E), and assayed in a similar manner as in Example 6. As shown in FIG. 10, all compounds III-A, III-B, III-C, and III-E inhibit LnCaP cell growth.

Example 11. Compounds III-D and III-F Inhibit the Growth of MCF7 Cells

Figure 11:
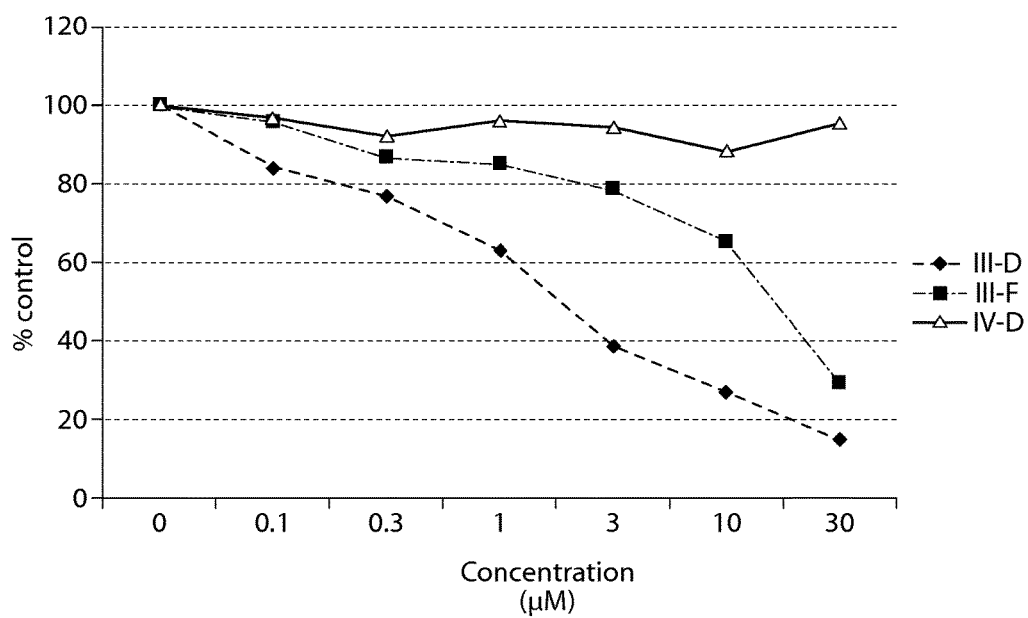
FIG. 11 shows that compounds III-D and III-F inhibit the growth of MCF7 cells.

MCF7 cells were obtained, cultured (in the presence of compounds III-D, III-F, and IV-D), and assayed in a similar manner as in Example 6. As shown in FIG. 11, both compounds III-D and III-F inhibit MCF7 cell growth, and compound IV-D does not.

Figure 12A:
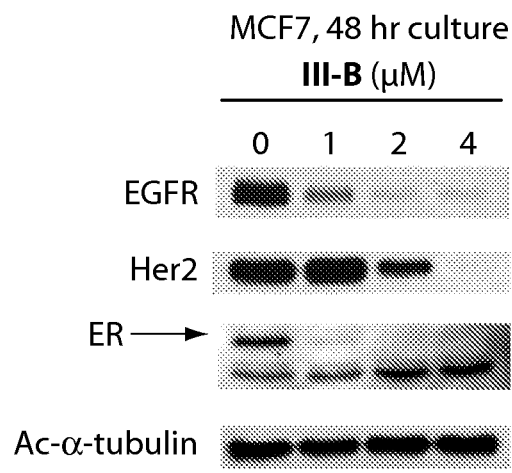
FIG. 12 shows that compound III-B down-regulates epidermal growth factor receptor (EGFR), human epidermal growth factor receptor 2 (HER2), and estrogen receptor (ER), in MCF7 cells without affecting histone acetylation.
Figure 12B:
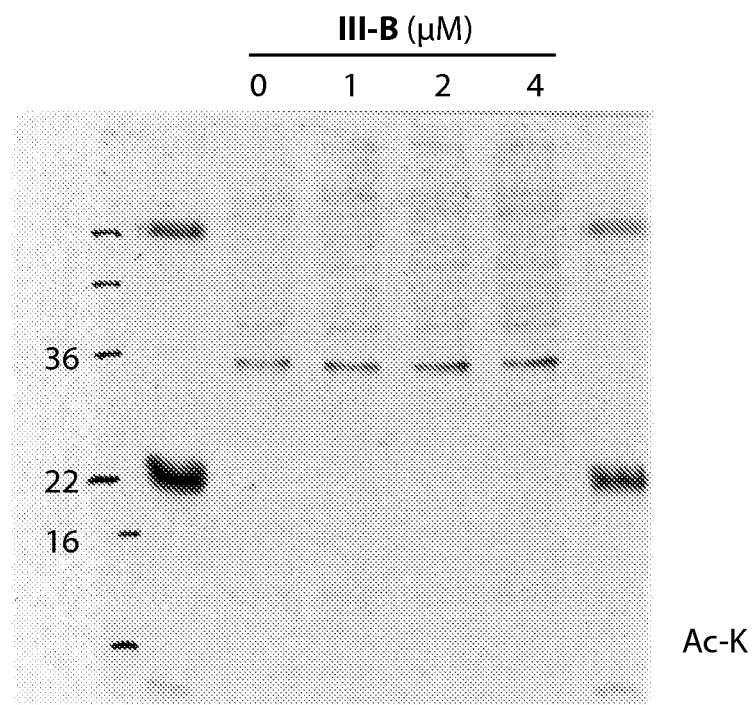

Example 12. Compound III-B Down-Regulates Epidermal Growth Factor Receptor (EGFR), Human Epidermal Growth Factor Receptor 2 (HER2), and Estrogen Receptor (ER) in MCF7 Cells without Affecting Histone Acetylation MCF7 cells were obtained and cultured (in the presence of compound III-B for 48 hr) in a similar manner as in Example 6. The cultured MCF7 cells were harvested, washed, and lysed using a lysis buffer (50 mM Tris-HCl (pH 7.4), 150 mM NaCl, 1% NP-40, 5 mM EDTA, 5 mM NaF, 1 mM Na$_3$VO$_4$, 1 mM PMSF, 5 µg/ml leupeptine, and 5 µg/ml aprotinin). The whole cell lysates were subjected to SDS-PAGE, transferred to nitrocellulose membrane (Bio-Rad Laboratories, Hercules, Calif.), and immunoblotted with specific antibodies as described in Hideshima et al. ("A proto-oncogene BCL6 is up-regulated in the bone marrow microenvironment in multiple myeloma cells." *Blood* (2010) 115:3772-3775). The antibodies used were polyclonal anti-acetylated lysine (Ac—K; Cell Signaling Technology, Danvers, Mass.) and antibodies directed against EGFR, HER2, ER, and acetylated-α-tubulin (Ac-α-tubulin). As shown in FIG. 12, compound III-B down-regulates EGFR, HER2, and ER in MCF7 cells (FIG. 12A). In contrast, the expression of Ac—K in MCF7 cells was not affected by compound III-B (FIG. 12B). These results suggest that compound III-B-triggered down-regulation of EGFR, HER2, and ER in breast cancer cells is due to a post-transcriptional event that is independent to histone acetylation.

Figure 13A:
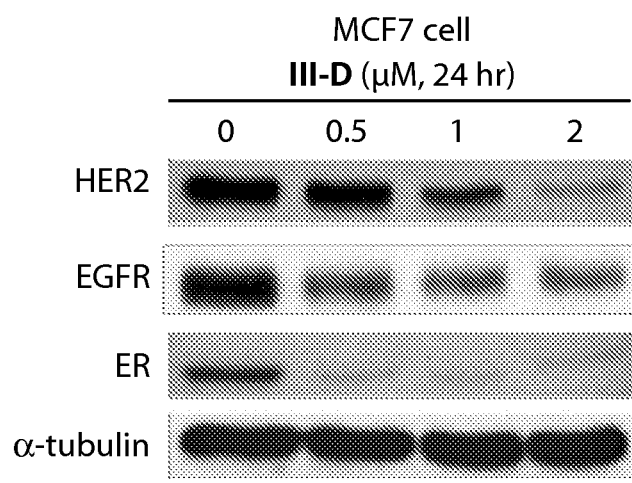
FIG. 13 shows that compound III-D down-regulates dose-dependently EGFR, HER2, and ER, in MCF7 or T47D cells.
Figure 13B:
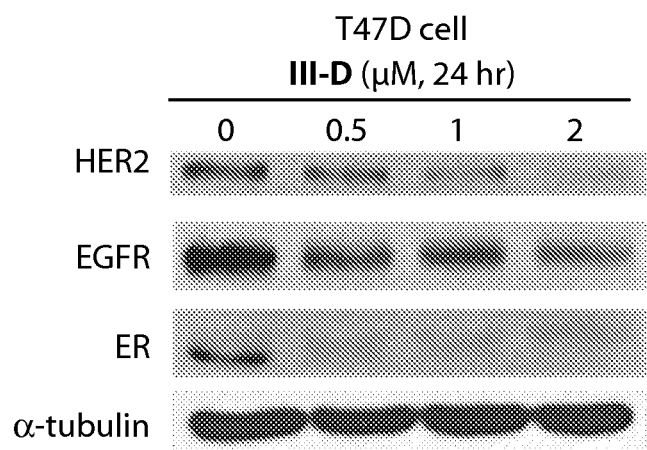

Example 13. Compound III-D Down-Regulates Dose-Dependently EGFR, HER2, and ER in MCF7 or T47D Cells MCF7 and T47D cells were obtained and cultured (in the presence of compound III-D (0, 0.5, 1, or 2 µM), for 24 hr), using methods similar to the ones described in Example 6. The whole cell lysates were immunoblotted with antibodies against EGFR, HER2, ER, and α-tubulin using methods similar to the ones described in Example 12. As shown in FIG. 13, compound III-D down-regulates, in a dose-dependent manner, EGFR, HER2, and ER in MCF7 or T47D cells (FIG. 13A). In contrast, the expression of α-tubulin in MCF7 or T47D cells was not affected by compound III-D (FIG. 13B).

Figure 14:
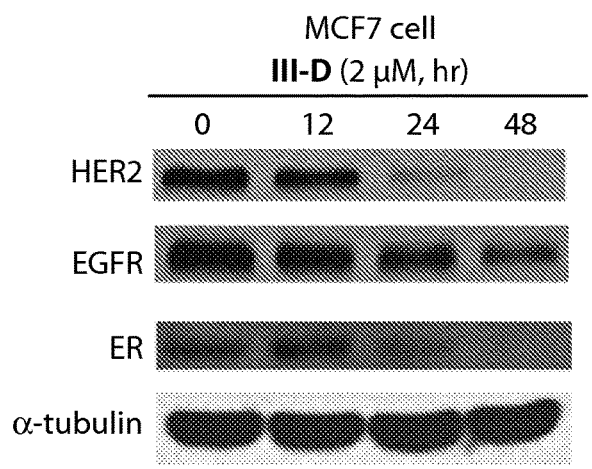
FIG. 14 shows that compound III-D down-regulates time-dependently EGFR, HER2, and ER, in MCF7 cells.

Example 14. Compound III-D Down-Regulates Time-Dependently EGFR, HER2, and ER in MCF7 Cells MCF7 cells were obtained and cultured (in the presence of 2 µM of compound III-D, for 0, 12, 24, or 48 hr) using methods similar to the ones described in Example 6. The whole cell lysates were immunoblotted with antibodies against EGFR, HER2, ER, and α-tubulin using methods similar to the ones described in Example 12. As shown in FIG. 14, compound III-D down-regulates, in a time-dependent manner, EGFR, HER2, and ER in MCF7 cells. In contrast, the expression of α-tubulin in MCF7 cells was not affected by compound III-D.

Figure 15:
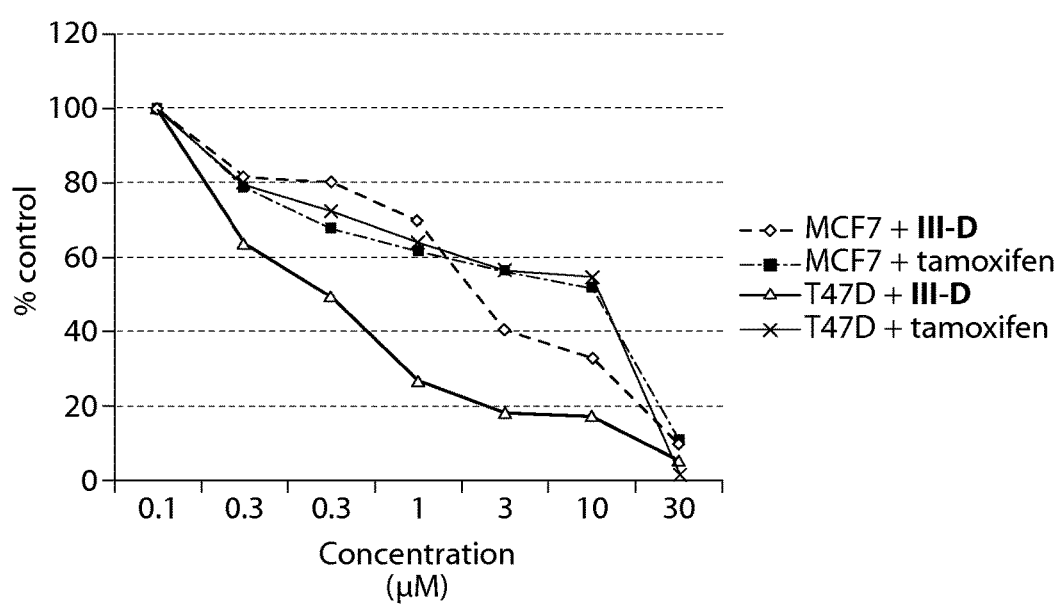
FIG. 15 shows that compound III-D is more potent than tamoxifen in inhibiting MCF7 or T47D cells.

Example 15. Compound III-D is More Potent than Tamoxifen in Inhibiting MCF7 or T47D Cells MCF7 and T47D cells were obtained, cultured (in the presence of compound III-D or tamoxifen), and assayed using methods similar to the ones described in Example 6. As shown in FIG. 15, compound III-D is more potent than tamoxifen in inhibiting T47D cells. Compound III-D is also more potent than tamoxifen in inhibiting MCF7 cells at least when the concentration of compound III-D and tamoxifen is 3-10 µM (FIG. 15).

Example 16. Compound III-D Enhances Bortezomib-Induced Cytotoxicity in MCF7 Cells MCF7 cells were obtained, cultured (in the presence of bortezomib (0, 10, 20, or 40 nM) and III-D (0, 0.3, 1, or 3 µM), for 48 hr), and assayed using methods similar to the ones described in Example 6. The statistical significance of the differences observed between the control cultures and the cultures treated with bortezomib and compound III-D was determined using the Wilcoxon signed-ranks test. The minimal level of significance was p<0.05. The interaction between compound III-D and bortezomib was analyzed by isobologram analysis using the CalcuSyn software program (Biosoft, Ferguson, Mo.) to determine whether the combination was additive or synergistic. A combination index (CI)<1.0 indicates a synergistic cell growth inhibitory effect.

Figure 16A:
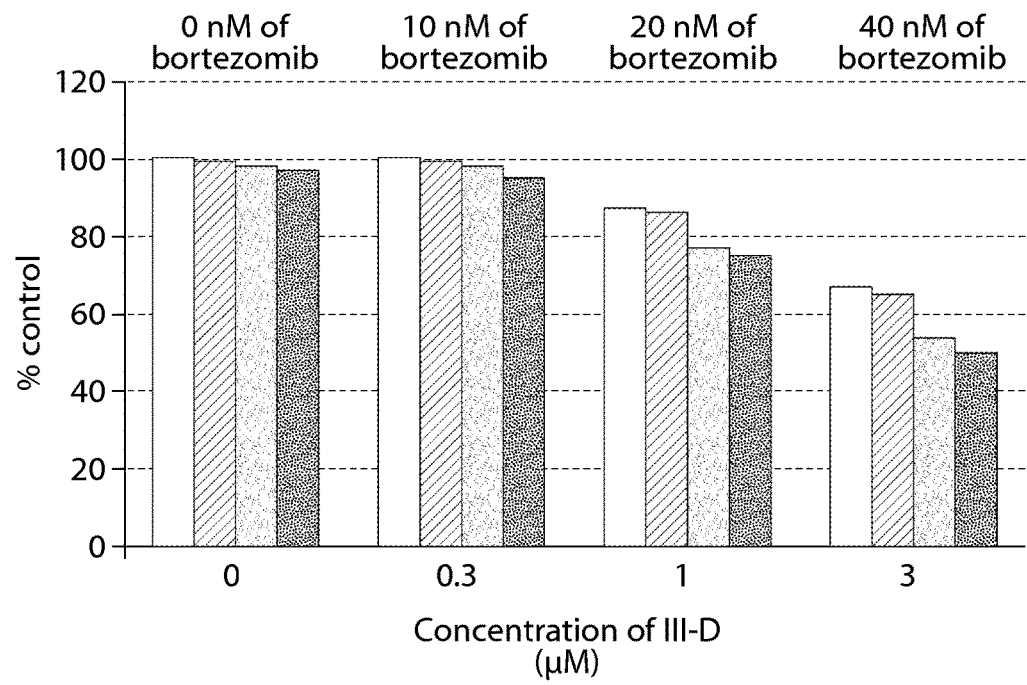
FIG. 16 shows that compound III-D enhances bortezomib-induced cytotoxicity in MCF7 cells.
Figure 16B:
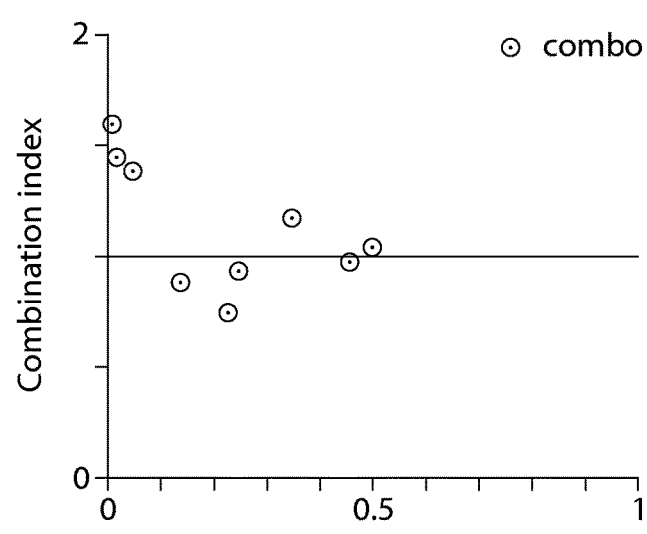

Bortezomib (FIG. 1) demonstrates remarkable clinical activity in MM. However, bortezomib's activity as a single agent in breast cancer is limited. Moreover, compared to MM cell line RPMI8226, breast cancer cells are relatively resistant to bortezomib treatment. Specifically, MCF7 cells are resistant to treatment with bortezomib (FIG. 16A). As shown in FIG. 16B and Table 1, compound III-D synergistically (CI<1) enhances bortezomib-induced MCF7 cytotoxicity, at least at certain concentrations.

TABLE 1

Combination indicia (CI) of a combination of compound III-D and bortezomib in inducing cytotoxicity in MCF7 cells

|  |  | Concentration of bortezomib (nM) | | |
| --- | --- | --- | --- | --- |
|  |  | 10 | 20 | 40 |
| Concentration of III-D (µM) | 0.3 | 1.58 | 1.29 | 0.83 |
|  | 1 | 0.66 | 0.53 | 0.53 |
|  | 3 | 1.22 | 1.03 | 0.98 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

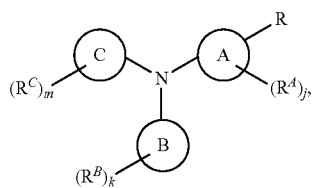

or a pharmaceutically acceptable salt, tautomer, stereoisomer, solvate, hydrate, or polymorph thereof, wherein:
each one of Rings A, B, and C is a phenyl ring;
R is a group of formula:

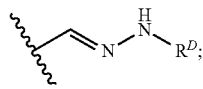

each occurrence of $R^A$ is independently halogen, unsubstituted $C_{1-8}$ alkyl, $C_{1-8}$ alkyl substituted with one or more instances of halogen, $-OR^{A1}$, $-SR^{A1}$, $-CN$, or $-NO_2$, wherein each occurrence of $R^{A1}$ is independently hydrogen, unsubstituted $C_{1-8}$ alkyl, or $C_{1-8}$ alkyl substituted with one or more instances of halogen;
each occurrence of $R^B$ is independently halogen, unsubstituted $C_{1-8}$ alkyl, $C_{1-8}$ alkyl substituted with one or more instances of halogen, $-OR^{B1}$, $-SR^{B1}$, $-CN$, or $-NO_2$, wherein each occurrence of $R^{B1}$ is independently hydrogen, unsubstituted $C_{1-8}$ alkyl, or $C_{1-8}$ alkyl substituted with one or more instances of halogen;
each occurrence of $R^C$ is independently halogen, unsubstituted $C_{1-8}$ alkyl, $C_{1-8}$ alkyl substituted with one or more instances of halogen, $-OR^{C1}$, $-SR^{C1}$, $-CN$, or $-NO_2$, wherein each occurrence of $R^{C1}$ is independently hydrogen, unsubstituted $C_{1-8}$ alkyl, or $C_{1-8}$ alkyl substituted with one or more instances of halogen;
$R^D$ is $-C(=O)R^{D1}$, wherein $R^{D1}$ is optionally substituted, fully saturated, 5- or 6-membered, monocyclic heterocyclyl that is not fused with an optionally substituted aryl ring or optionally substituted heteroaryl ring;
j is 0, 1, 2, 3, or 4;
k is 0, 1, 2, 3, 4, or 5; and
m is 0, 1, 2, 3, 4, or 5.

2. The compound of claim 1, or a pharmaceutically acceptable salt, tautomer, stereoisomer, solvate, hydrate, or polymorph thereof, wherein j, k, and m are each 0.

3. The compound of claim 1, wherein the compound is of the formula:

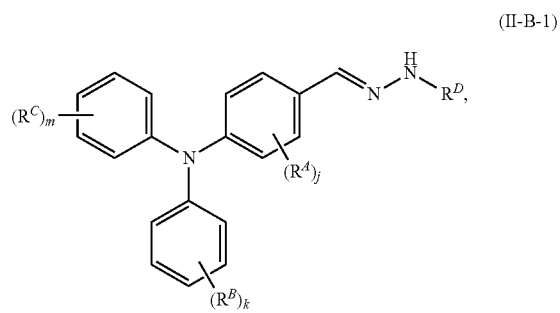

or a pharmaceutically acceptable salt, tautomer, stereoisomer, solvate, hydrate, or polymorph thereof.

4. The compound of claim 1, wherein the compound is of the formula:

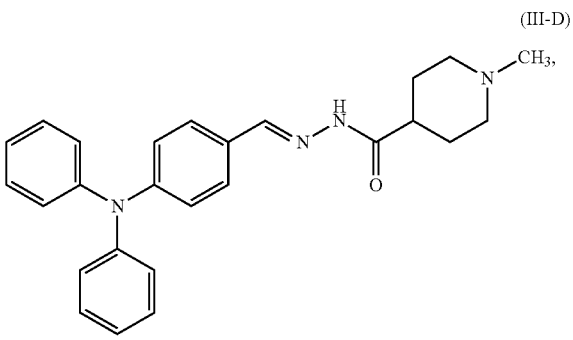 [SMILES: CN1CCC(C(=O)N/N=C/c2ccc(N(c3ccccc3)c3ccccc3)cc2)CC1]

or a pharmaceutically acceptable salt, tautomer, stereoisomer, solvate, hydrate, or polymorph thereof.

5. A pharmaceutical composition comprising a compound of claim 1, or a pharmaceutically acceptable salt, tautomer, stereoisomer, solvate, hydrate, or polymorph thereof, and optionally a pharmaceutically acceptable excipient.

6. The compound of claim 1, or a pharmaceutically acceptable salt, tautomer, stereoisomer, solvate, hydrate, or polymorph thereof, wherein $R^{D1}$ is optionally substituted, fully saturated, 5-membered, monocyclic heterocyclyl that is not fused with an optionally substituted aryl ring or optionally substituted heteroaryl ring.

7. The compound of claim 1, or a pharmaceutically acceptable salt, tautomer, stereoisomer, solvate, hydrate, or polymorph thereof, wherein R is

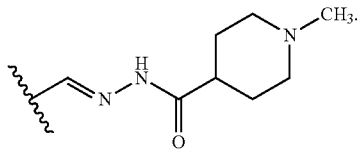 [SMILES: */C=N/NC(=O)C1CCN(C)CC1]

8. The compound of claim 1, wherein the compound is of the formula:

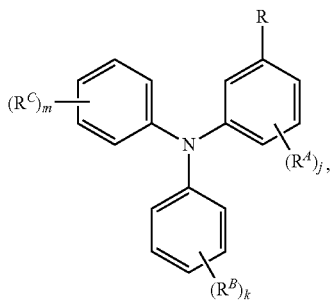

(II-A-2)

or a pharmaceutically acceptable salt, tautomer, stereoisomer, solvate, hydrate, or polymorph thereof.

9. The compound of claim 1, wherein the compound is of the formula:

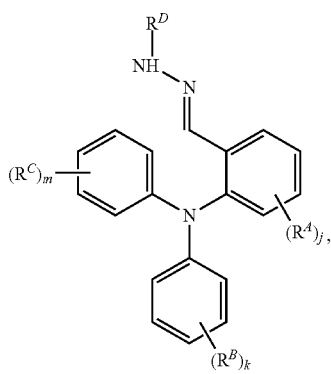

(II-B-3)

or a pharmaceutically acceptable salt, tautomer, stereoisomer, solvate, hydrate, or polymorph thereof.

10. The compound of claim 1, or a pharmaceutically acceptable salt thereof.

11. The compound of claim 1, or a pharmaceutically acceptable salt, tautomer, stereoisomer, solvate, hydrate, or polymorph thereof, wherein $R^{D1}$ is optionally substituted, fully saturated, 6-membered, monocyclic heterocyclyl that is not fused with an optionally substituted aryl ring or optionally substituted heteroaryl ring.

12. The compound of claim 1, wherein the compound is of the formula:

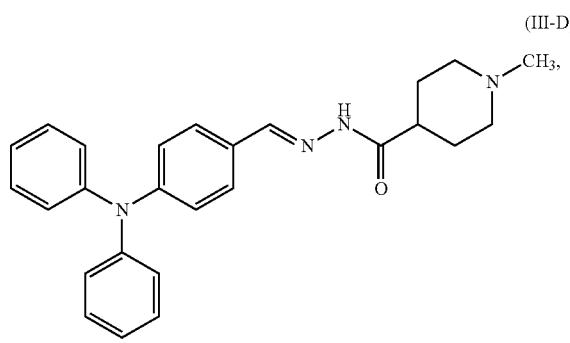

(III-D)

or a pharmaceutically acceptable salt thereof.

13. The compound of claim 1, wherein the compound is of the formula:

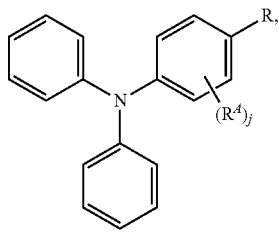

or a pharmaceutically acceptable salt, tautomer, stereoisomer, solvate, hydrate, or polymorph thereof.

14. The compound of claim 1, wherein the compound is of the formula:

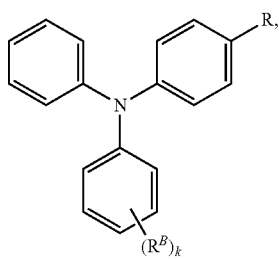

or a pharmaceutically acceptable salt, tautomer, stereoisomer, solvate, hydrate, or polymorph thereof.

15. The compound of claim 1, or a pharmaceutically acceptable salt, tautomer, stereoisomer, solvate, hydrate, or polymorph thereof, wherein $R^{D1}$ is optionally substituted piperidinyl that is not fused with an optionally substituted aryl ring or optionally substituted heteroaryl ring.

16. The compound of claim 1, or a pharmaceutically acceptable salt, tautomer, stereoisomer, solvate, hydrate, or polymorph thereof, wherein $R^{D1}$ is fully saturated, 5- or 6-membered, monocyclic heterocyclyl that is not fused with an optionally substituted aryl ring or optionally substituted heteroaryl ring and is optionally substituted with one or more substituents independently selected from the group consisting of alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and acyloxy.

17. The pharmaceutical composition of claim 5, wherein the compound is of the formula:

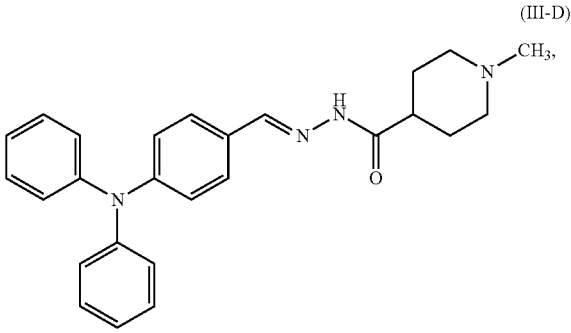 [SMILES: CN1CCC(C(=O)N/N=C/c2ccc(N(c3ccccc3)c3ccccc3)cc2)CC1]

(III-D)

or a pharmaceutically acceptable salt, tautomer, stereoisomer, solvate, hydrate, or polymorph thereof.

18. The pharmaceutical composition of claim 5, wherein the compound is of the formula:
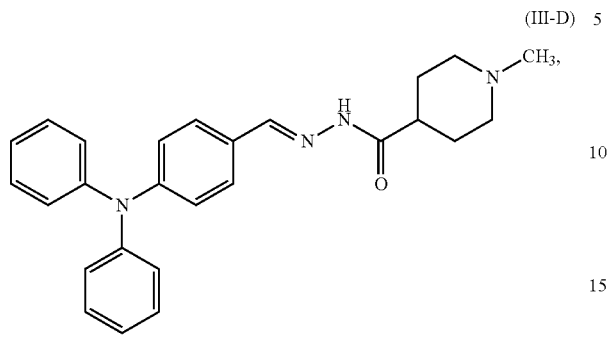
(III-D)
or a pharmaceutically acceptable salt thereof.
19. The pharmaceutical composition of claim 5 further comprising an additional therapeutic agent.
20. The pharmaceutical composition of claim 5 further comprising a proteasome inhibitor or a heat shock protein 90 (Hsp90) inhibitor.
* * * * *